US009394549B2

(12) United States Patent
Nukui et al.

(10) Patent No.: US 9,394,549 B2
(45) Date of Patent: Jul. 19, 2016

(54) METHOD FOR PRODUCING USEFUL CHEMICAL SUBSTANCE FROM TEREPHTHALIC ACID POTASSIUM SALT

(71) Applicant: GENARIS, INC., Yokohama-shi, Kanagawa (JP)

(72) Inventors: Noriyuki Nukui, Yokohama (JP); Maki Komaki, Yokohama (JP); Akito Nishizawa, Yokohama (JP); Tatsunari Nishi, Tokyo (JP)

(73) Assignee: GENARIS, INC., Yokohama-Shi (JP)

( * ) Notice: Subject to any disclaimer, the term of this patent is extended or adjusted under 35 U.S.C. 154(b) by 221 days.

(21) Appl. No.: 14/143,912

(22) Filed: Dec. 30, 2013

(65) Prior Publication Data

US 2014/0120593 A1 May 1, 2014

Related U.S. Application Data

(63) Continuation-in-part of application No. PCT/JP2012/051854, filed on Jan. 27, 2012.

(51) Int. Cl.
*C12P 7/44* (2006.01)
*C12P 7/42* (2006.01)

(52) U.S. Cl.
CPC .... *C12P 7/44* (2013.01); *C12P 7/42* (2013.01)

(58) Field of Classification Search
CPC ............ C08J 11/16; C12N 15/09; C12P 7/42; C12P 7/44
See application file for complete search history.

(56) References Cited

U.S. PATENT DOCUMENTS

| 3,544,622 | A | 12/1970 | England |
| 4,542,239 | A | 9/1985 | Lamparter et al. |
| 5,068,414 | A | 11/1991 | Ruppen et al. |
| 5,124,479 | A | 6/1992 | Ruppen et al. |
| 7,893,122 | B2 | 2/2011 | Fregoso-Infante et al. |
| 2007/0219339 | A1 | 9/2007 | Fregoso-Infante et al. |

FOREIGN PATENT DOCUMENTS

| JP | 11021374 | A | 1/1999 |
| JP | 2000169623 | A | 6/2000 |
| JP | 2002060542 | A | 2/2002 |
| JP | 3715812 | B2 | 9/2005 |
| JP | 2007104942 | A | 4/2007 |
| JP | 2008278823 | A | 11/2008 |
| JP | 2009065839 | A | 4/2009 |
| JP | 2009213392 | A | 9/2009 |
| JP | 2010207094 | A | 9/2010 |
| WO | 2005082826 | A1 | 9/2005 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Sadowski et al., Current Opinion in Structural Biology 19:357-362, 2009.*
Schlafli et al., Journal of Bacteriology 176(21):6644-6652, 1994.*
Sasoh et al., GenBank accession No. BAE47077, Mar. 8, 2006.*
Sasoh et al., GenBank accession No. BAE47078, Mar. 8, 2006.*
Wang et al., Environmental Health Perspectives 103(Suppl 5):9-12, 1995.*
Wang et al., GenBank accession No. AY923836, Mar. 5, 2005.*
Supplementary European Search Report, mailed Feb. 3, 2015, in European Application EP 12 86 6812.
Database WPI, AN 2009-N94120, Thomson Scientific, London, Great Britain, Week 200965, Sep. 24, 2009.
M. Sasoh et al., "Characterization of the Terephthalate Degradation Genes of *Comamonas* sp. Strain E6," Applied and Environmental Microbiology, American Society for Microbiology, vol. 72, No. 3, Mar. 1, 2006, pp. 1825-1832.
K.Y. Choi et al., "Molecular and biochemical analysis of phthalate and terephthalate degradation by *Rhodococcus* sp. strain DK17," FEMS Microbiology Letters, Wiley-Blackwell Publishing Ltd, Great Britain, vol. 252, No. 2, Nov. 15, 2005, pp. 207-213.
M. P. McLeod et al., "The complete genome of *Rhodococcus* sp. RHA1 provides insights into a catabolic powerhouse," Proc. Natl. Acad. Sci. USA, 2006, vol. 103, pp. 15582-15587.
S.R., Shukla et al., "Glycolysis of Polyethylene Terephthalate Waste Fibers," Journal of Applied Polymer Science, 2005, vol. 97, pp. 513-517.
International Preliminary Report on Patentability issued Jul. 29, 2014 in International Application No. PCT/JP2012/051854, (mailing date of transmittal Aug. 7, 2014).
A. Boronat et al., "Experimental Evolution of a Metabolic Pathway for Ethylene Glycol Utilization by *Escherichia coli*," Journal of Bacteriology, Jan. 1983, vol. 153, No. 1, pp. 134-139.
Y-M. Chen et al., "Constitutive activation of the fucAO operon and silencing of the divergently transcribed fucPIK operon by an IS5 element in *Escherichia coli* mutants selected for growth on L-1,2-propanediol," Journal of Bacteriology, 1989, vol. 171, No. 11, p. 6097.
A. Goje et al., "Chemical Recycling, Kinetics, and Thermodynamics of Hydrolysis of Poly(Ethylene Terephthalate) Waste with Nonaqueous Potassium Hydroxide Solution," Polymer-Plastics Technology and Engineering, 2004, vol. 43, No. 2, pp. 369-388.
Z. Lu et al., "Protein Chemistry and Structure: Evolution of an *Escherichia coli* Protein with Increased Resistance to Oxidative Stress," Journal of Biological Chemistry, 1998, vol. 273, pp. 8308-8316.
T. Nishi, "Development of Phenolic-Compounds Producing Technologies using Microorganisms," Bio Industry, 2011, vol. 28, No. 11, pp. 4.44-4.49 (with English translation).

* cited by examiner

*Primary Examiner* — Delia Ramirez
(74) *Attorney, Agent, or Firm* — Kenyon & Kenyon LLP

(57) ABSTRACT

TPA-DHD can be produced by using, as a raw material, terephthalic acid salt that contains 0.5 times or more and twice or less the amount of potassium based on all of the terephthalic acids contained in the terephthalic acid salt in terms of moles and by using a microorganism expressing terephthalate 1,2-dioxygenase. Further, TPA-DHD can be converted into protocatechuic acid by TPA-DHD dehydrogenase and protocatechuic acid can be converted into gallic acid by para-hydroxybenzoate hydroxylase. In addition, by subjecting waste polyesters to heat treatment in an ethylene glycol solvent or 1-butanol solvent containing potassium hydroxide, such polyesters can be efficiently depolymerized, and potassium terephthalate suitable to chemical production by the microorganism can be prepared.

12 Claims, 2 Drawing Sheets

SEQUENCE LISTING

```
<160> NUMBER OF SEQ ID NOS: 43

<210> SEQ ID NO 1
<211> LENGTH: 1242
<212> TYPE: DNA
<213> ORGANISM: Comamonas testosteroni
<220> FEATURE:
<221> NAME/KEY: CDS
<222> LOCATION: (1)..(1242)

<400> SEQUENCE: 1 atg caa gaa tcc att atc cag tgg cat ggg gcc act aat aca cgc gtg      48
Met Gln Glu Ser Ile Ile Gln Trp His Gly Ala Thr Asn Thr Arg Val
1               5                   10                  15 cct ttc ggt atc tac act gac aca gcc aat gct gat caa gaa cag cag      96
Pro Phe Gly Ile Tyr Thr Asp Thr Ala Asn Ala Asp Gln Glu Gln Gln
                20                  25                  30 cgc atc tat cgc ggc gag gtc tgg aac tac ctg tgc ctg gaa tct gaa     144
Arg Ile Tyr Arg Gly Glu Val Trp Asn Tyr Leu Cys Leu Glu Ser Glu
            35                  40                  45 atc ccc gag gct ggt gat ttc cgt act acc ttt gcc ggt gaa aca ccg     192
Ile Pro Glu Ala Gly Asp Phe Arg Thr Thr Phe Ala Gly Glu Thr Pro
        50                  55                  60 ata gtt gtc gta cgg gat gcc gac cag gaa atc tac gcc ttc gag aac     240
Ile Val Val Val Arg Asp Ala Asp Gln Glu Ile Tyr Ala Phe Glu Asn
65                  70                  75                  80 cgc tgc gcg cat cgc ggc gct ctc atc gct ctg gag aaa tcg gga cgt     288
Arg Cys Ala His Arg Gly Ala Leu Ile Ala Leu Glu Lys Ser Gly Arg
                85                  90                  95 acg gat agt ttc cag tgc gtc tat cac gcc tgg agc tac aac cga cag     336
Thr Asp Ser Phe Gln Cys Val Tyr His Ala Trp Ser Tyr Asn Arg Gln
                100                 105                 110 gga gat ctg acc ggc gtt gcc ttc gag aaa ggt gtc aag ggc cag ggt     384
Gly Asp Leu Thr Gly Val Ala Phe Glu Lys Gly Val Lys Gly Gln Gly
            115                 120                 125 ggc atg ccg gcc tca ttc tgc aaa gaa gag cat ggc ccg cgc aag ctc     432
Gly Met Pro Ala Ser Phe Cys Lys Glu Glu His Gly Pro Arg Lys Leu
        130                 135                 140 cgc gtg gct gtc ttt tgc ggt ttg gtc ttt ggc agt ttt tcc gag gac     480
Arg Val Ala Val Phe Cys Gly Leu Val Phe Gly Ser Phe Ser Glu Asp
145                 150                 155                 160 gta ccc agc att gag gat tac ctt ggc cct gag att tgc gag cgc ata     528
Val Pro Ser Ile Glu Asp Tyr Leu Gly Pro Glu Ile Cys Glu Arg Ile
                165                 170                 175 gag cgc gtg ctg cac aag ccc gta gaa gtc atc ggt cgc ttc acg caa     576
Glu Arg Val Leu His Lys Pro Val Glu Val Ile Gly Arg Phe Thr Gln
                180                 185                 190 aag ctg cct aac aac tgg aag ctc tac ttc gag aac gtg aag gac agc     624
Lys Leu Pro Asn Asn Trp Lys Leu Tyr Phe Glu Asn Val Lys Asp Ser
            195                 200                 205
```

| | | |
|---|---|---|
| tat cac gcc agc ctc ctg cat atg ttc ttc acc acc ttc gag ctg aat<br>Tyr His Ala Ser Leu Leu His Met Phe Phe Thr Thr Phe Glu Leu Asn<br>210                             215                    220 | | 672 |
| cgc ctc tca caa aaa ggc gga gtc atc gtc gac gag tcg ggt ggc cac<br>Arg Leu Ser Gln Lys Gly Gly Val Ile Val Asp Glu Ser Gly Gly His<br>225                         230                     235                 240 | | 720 |
| cat gtg agc tat tcc atg att gat cgt agc gcc aaa gac gac tcg tac<br>His Val Ser Tyr Ser Met Ile Asp Arg Ser Ala Lys Asp Asp Ser Tyr<br>                      245                     250                     255 | | 768 |
| aag gac cag gcc atc cgc tcc gac aac gag cgt tac cgg ctc aaa gat<br>Lys Asp Gln Ala Ile Arg Ser Asp Asn Glu Arg Tyr Arg Leu Lys Asp<br>                260                     265                    270 | | 816 |
| ccc agc ctt cta gag ggc ttc gag gag ttc gag gac ggc gtg acc ctg<br>Pro Ser Leu Leu Glu Gly Phe Glu Glu Phe Glu Asp Gly Val Thr Leu<br>                      275                     280                    285 | | 864 |
| cag atc ctt tct gtg ttc cct ggc ttt gtg ctg cag cag att cag aac<br>Gln Ile Leu Ser Val Phe Pro Gly Phe Val Leu Gln Gln Ile Gln Asn<br>290                             295                    300 | | 912 |
| agc atc gcc gtg cgt cag ttg ttg ccc aag agc atc tcc agc tcg gaa<br>Ser Ile Ala Val Arg Gln Leu Leu Pro Lys Ser Ile Ser Ser Ser Glu<br>305                         310                     315                 320 | | 960 |
| ctc aac tgg acc tat ctt ggc tat gca gat gac agt gca gag cag cgc<br>Leu Asn Trp Thr Tyr Leu Gly Tyr Ala Asp Asp Ser Ala Glu Gln Arg<br>                      325                     330                    335 | | 1008 |
| aag gtc aga ctc aaa cag gcc aac ctc atc ggc cct gca gga ttt att<br>Lys Val Arg Leu Lys Gln Ala Asn Leu Ile Gly Pro Ala Gly Phe Ile<br>                340                     345                    350 | | 1056 |
| tcc atg gag gac gga gct gtc ggt gga ttc gtg cag cgt ggc atc gca<br>Ser Met Glu Asp Gly Ala Val Gly Gly Phe Val Gln Arg Gly Ile Ala<br>355                         360                     365 | | 1104 |
| ggc gct gcc aac ctt gat gcg gtc atc gag atg ggc gga gac cac gaa<br>Gly Ala Ala Asn Leu Asp Ala Val Ile Glu Met Gly Gly Asp His Glu<br>370                         375                    380 | | 1152 |
| ggc tct agc gag ggc cgc gcc aca gaa acc tcg gta cgc ggc ttt tgg<br>Gly Ser Ser Glu Gly Arg Ala Thr Glu Thr Ser Val Arg Gly Phe Trp<br>385                         390                     395                 400 | | 1200 |
| aag gcc tac cgc aag cat atg gga cag gag atg caa gca tga<br>Lys Ala Tyr Arg Lys His Met Gly Gln Glu Met Gln Ala<br>                      405                     410 | | 1242 |

<210> SEQ ID NO 2
<211> LENGTH: 413
<212> TYPE: PRT
<213> ORGANISM: Comamonas testosteroni

<400> SEQUENCE: 2

Met Gln Glu Ser Ile Ile Gln Trp His Gly Ala Thr Asn Thr Arg Val
1                 5                    10                  15

Pro Phe Gly Ile Tyr Thr Asp Thr Ala Asn Ala Asp Gln Glu Gln Gln
                 20                    25                  30

Arg Ile Tyr Arg Gly Glu Val Trp Asn Tyr Leu Cys Leu Glu Ser Glu
        35                    40                  45

Ile Pro Glu Ala Gly Asp Phe Arg Thr Thr Phe Ala Gly Glu Thr Pro
50                    55                    60

Ile Val Val Arg Asp Ala Asp Gln Glu Ile Tyr Ala Phe Glu Asn
65                 70                    75                  80

Arg Cys Ala His Arg Gly Ala Leu Ile Ala Leu Glu Lys Ser Gly Arg
                 85                    90                  95

```
Thr Asp Ser Phe Gln Cys Val Tyr His Ala Trp Ser Tyr Asn Arg Gln
            100                 105                 110

Gly Asp Leu Thr Gly Val Ala Phe Glu Lys Gly Val Lys Gly Gln Gly
        115                 120                 125

Gly Met Pro Ala Ser Phe Cys Lys Glu Glu His Gly Pro Arg Lys Leu
    130                 135                 140

Arg Val Ala Val Phe Cys Gly Leu Val Phe Gly Ser Phe Ser Glu Asp
145                 150                 155                 160

Val Pro Ser Ile Glu Asp Tyr Leu Gly Pro Glu Ile Cys Glu Arg Ile
                165                 170                 175

Glu Arg Val Leu His Lys Pro Val Glu Val Ile Gly Arg Phe Thr Gln
            180                 185                 190

Lys Leu Pro Asn Asn Trp Lys Leu Tyr Phe Glu Asn Val Lys Asp Ser
        195                 200                 205

Tyr His Ala Ser Leu Leu His Met Phe Phe Thr Thr Phe Glu Leu Asn
    210                 215                 220

Arg Leu Ser Gln Lys Gly Gly Val Ile Val Asp Glu Ser Gly Gly His
225                 230                 235                 240

His Val Ser Tyr Ser Met Ile Asp Arg Ser Ala Lys Asp Ser Tyr
                245                 250                 255

Lys Asp Gln Ala Ile Arg Ser Asp Asn Glu Arg Tyr Arg Leu Lys Asp
            260                 265                 270

Pro Ser Leu Leu Glu Gly Phe Glu Phe Glu Asp Gly Val Thr Leu
        275                 280                 285

Gln Ile Leu Ser Val Phe Pro Gly Phe Val Leu Gln Gln Ile Gln Asn
    290                 295                 300

Ser Ile Ala Val Arg Gln Leu Leu Pro Lys Ser Ile Ser Ser Glu
305                 310                 315                 320

Leu Asn Trp Thr Tyr Leu Gly Tyr Ala Asp Asp Ser Ala Glu Gln Arg
                325                 330                 335

Lys Val Arg Leu Lys Gln Ala Asn Leu Ile Gly Pro Ala Gly Phe Ile
            340                 345                 350

Ser Met Glu Asp Gly Ala Val Gly Gly Phe Val Gln Arg Gly Ile Ala
        355                 360                 365

Gly Ala Ala Asn Leu Asp Ala Val Ile Glu Met Gly Gly Asp His Glu
    370                 375                 380

Gly Ser Ser Glu Gly Arg Ala Thr Glu Thr Ser Val Arg Gly Phe Trp
385                 390                 395                 400

Lys Ala Tyr Arg Lys His Met Gly Gln Glu Met Gln Ala
                405                 410

<210> SEQ ID NO 3
<211> LENGTH: 465
<212> TYPE: DNA
<213> ORGANISM: Comamonas testosteroni
<220> FEATURE:
<221> NAME/KEY: CDS
<222> LOCATION: (1)..(465)

<400> SEQUENCE: 3 atg atc cat gaa att caa atc gcg gcc ttc aat gcc gct tac gcg aag    48
Met Ile His Glu Ile Gln Ile Ala Ala Phe Asn Ala Ala Tyr Ala Lys
1               5                   10                  15 acc ata gac agt gac gtt atg gag caa tgg cca acc ttc ttc acg aag    96
Thr Ile Asp Ser Asp Val Met Glu Gln Trp Pro Thr Phe Phe Thr Lys
            20                  25                  30
```

```
gat tgc cat tat cgc gtc acc aat gtc gac aac cat gct gaa gga ctt      144
Asp Cys His Tyr Arg Val Thr Asn Val Asp Asn His Ala Glu Gly Leu
         35                  40                  45 gct gct ggc att gtc tgg gca gat tcg cag gac atg ctc acc gac cga      192
Ala Ala Gly Ile Val Trp Ala Asp Ser Gln Asp Met Leu Thr Asp Arg
 50                  55                  60 att tct gcg ctg cgc gaa gcc aat atc tac gag cgc cac cgc tat cgc      240
Ile Ser Ala Leu Arg Glu Ala Asn Ile Tyr Glu Arg His Arg Tyr Arg
 65                  70                  75                  80 cat atc ctg ggt ctg cct tcg atc cag tca gcc gat gca aca cag gcc      288
His Ile Leu Gly Leu Pro Ser Ile Gln Ser Ala Asp Ala Thr Gln Ala
                 85                  90                  95 agt gct tcc acg cca ttc ctg gtg ctg cgc atc atg cat acc ggg gaa      336
Ser Ala Ser Thr Pro Phe Leu Val Leu Arg Ile Met His Thr Gly Glu
             100                 105                 110 aca gag gtc ttt gcc agc ggt gag tac cac gac aaa ttc acc acg atc      384
Thr Glu Val Phe Ala Ser Gly Glu Tyr His Asp Lys Phe Thr Thr Ile
         115                 120                 125 gat gga aag tta cgt ctg caa gag cgc gtc gcg gtt tgc gac agc acg      432
Asp Gly Lys Leu Arg Leu Gln Glu Arg Val Ala Val Cys Asp Ser Thr
130                 135                 140 gtg acg gac acg ctg atg tca ttg ccg cta tga                          465
Val Thr Asp Thr Leu Met Ser Leu Pro Leu
145                 150

<210> SEQ ID NO 4
<211> LENGTH: 154
<212> TYPE: PRT
<213> ORGANISM: Comamonas testosteroni

<400> SEQUENCE: 4

Met Ile His Glu Ile Gln Ile Ala Ala Phe Asn Ala Ala Tyr Ala Lys
 1               5                  10                  15

Thr Ile Asp Ser Asp Val Met Glu Gln Trp Pro Thr Phe Phe Thr Lys
             20                  25                  30

Asp Cys His Tyr Arg Val Thr Asn Val Asp Asn His Ala Glu Gly Leu
         35                  40                  45

Ala Ala Gly Ile Val Trp Ala Asp Ser Gln Asp Met Leu Thr Asp Arg
 50                  55                  60

Ile Ser Ala Leu Arg Glu Ala Asn Ile Tyr Glu Arg His Arg Tyr Arg
 65                  70                  75                  80

His Ile Leu Gly Leu Pro Ser Ile Gln Ser Ala Asp Ala Thr Gln Ala
                 85                  90                  95

Ser Ala Ser Thr Pro Phe Leu Val Leu Arg Ile Met His Thr Gly Glu
             100                 105                 110

Thr Glu Val Phe Ala Ser Gly Glu Tyr His Asp Lys Phe Thr Thr Ile
         115                 120                 125

Asp Gly Lys Leu Arg Leu Gln Glu Arg Val Ala Val Cys Asp Ser Thr
130                 135                 140

Val Thr Asp Thr Leu Met Ser Leu Pro Leu
145                 150

<210> SEQ ID NO 5
<211> LENGTH: 1011
<212> TYPE: DNA
<213> ORGANISM: Comamonas testosteroni
<220> FEATURE:
<221> NAME/KEY: CDS
<222> LOCATION: (1)..(1011)
```

```
<400> SEQUENCE: 5 atg aac cac cag atc cat atc cac gac tct gat atc gcg ttc ccc tgc      48
Met Asn His Gln Ile His Ile His Asp Ser Asp Ile Ala Phe Pro Cys
1               5                   10                  15 gcg cct ggg caa tcc gta ctg gat gca gcc ctg cag gcc ggc atc gag      96
Ala Pro Gly Gln Ser Val Leu Asp Ala Ala Leu Gln Ala Gly Ile Glu
            20                  25                  30 ctg ccc tat tcc tgc cgc aaa ggt agc tgt ggc aac tgt gcg agt acg     144
Leu Pro Tyr Ser Cys Arg Lys Gly Ser Cys Gly Asn Cys Ala Ser Thr
        35                  40                  45 ctg ctc gac gga aat att act tcc ttc aat ggc atg gcc gtg cgc agc     192
Leu Leu Asp Gly Asn Ile Thr Ser Phe Asn Gly Met Ala Val Arg Ser
    50                  55                  60 gaa ctc tgc acc tcg gag cag gta ttg ctg tgc ggc tgc acc gcc gcc     240
Glu Leu Cys Thr Ser Glu Gln Val Leu Leu Cys Gly Cys Thr Ala Ala
65                  70                  75                  80 agc gat ata cgt atc cag ccg agc tcc ttt cgc cgt ctc gac ccg gaa     288
Ser Asp Ile Arg Ile Gln Pro Ser Ser Phe Arg Arg Leu Asp Pro Glu
                85                  90                  95 gcc cgc aaa cgt ttt acg gcc aag gtg tac agc aat aca ctg gcg gca     336
Ala Arg Lys Arg Phe Thr Ala Lys Val Tyr Ser Asn Thr Leu Ala Ala
            100                 105                 110 ccc gat gtc tcg cta ctg cgc ctg cgc ctg cct gtg ggc aag cgc gcc     384
Pro Asp Val Ser Leu Leu Arg Leu Arg Leu Pro Val Gly Lys Arg Ala
        115                 120                 125 aaa ttt gaa gcc ggc caa tac ctg ctg att cac ctc gac ggc ggg gaa     432
Lys Phe Glu Ala Gly Gln Tyr Leu Leu Ile His Leu Asp Gly Gly Glu
    130                 135                 140 agc cgc agc tac tct atg gcc aac cca ccc cat gag agc gat ggc atc     480
Ser Arg Ser Tyr Ser Met Ala Asn Pro Pro His Glu Ser Asp Gly Ile
145                 150                 155                 160 aca ttg cat atc agg cat gta ccg ggt ggt cgc ttc agc act atc gtt     528
Thr Leu His Ile Arg His Val Pro Gly Gly Arg Phe Ser Thr Ile Val
                165                 170                 175 cag cag ttg aag tct ggt gac aca ttg gat atc gaa ctg cca ttc ggc     576
Gln Gln Leu Lys Ser Gly Asp Thr Leu Asp Ile Glu Leu Pro Phe Gly
            180                 185                 190 agc atc gcg ttg aag cct gac gac agc aga ccc cta gtt tgc gtt gca     624
Ser Ile Ala Leu Lys Pro Asp Asp Ser Arg Pro Leu Val Cys Val Ala
        195                 200                 205 gga ggc acc gga ttt gca ccc atc aag tcc gtt ctg gat gac ctg gcc     672
Gly Gly Thr Gly Phe Ala Pro Ile Lys Ser Val Leu Asp Asp Leu Ala
    210                 215                 220 aaa cgc aag gta cag cgc gac atc acg ctg att tgg ggt gct cgc aac     720
Lys Arg Lys Val Gln Arg Asp Ile Thr Leu Ile Trp Gly Ala Arg Asn
225                 230                 235                 240 ccc tct ggc ctg tat ctt cct agc gcc atc gac aag tgg cgc aaa gct     768
Pro Ser Gly Leu Tyr Leu Pro Ser Ala Ile Asp Lys Trp Arg Lys Ala
                245                 250                 255 tgg ccg cag ttt cgc tac att gca gcc atc act gac cta agc aac gtg     816
Trp Pro Gln Phe Arg Tyr Ile Ala Ala Ile Thr Asp Leu Ser Asn Val
            260                 265                 270 cct gcg gat gct cac gcc ggt cgg gtg gat gac gcg cta cgc atg cac     864
Pro Ala Asp Ala His Ala Gly Arg Val Asp Asp Ala Leu Arg Met His
        275                 280                 285 ttt gac aac cta cac gat cat gtt gtc cac tgc tgt ggc tca cca gcc     912
Phe Asp Asn Leu His Asp His Val Val His Cys Cys Gly Ser Pro Ala
    290                 295                 300
```

-continued

```
ctc gtt caa tct gtg cgc aca gca gcc tcc aat atg ggc ctg cta gca    960
Leu Val Gln Ser Val Arg Thr Ala Ala Ser Asn Met Gly Leu Leu Ala
305                 310                 315                 320 caa gac ttt cat gcg gat gtg ttc gct aca gac ccg act ggc cac cac   1008
Gln Asp Phe His Ala Asp Val Phe Ala Thr Asp Pro Thr Gly His His
                325                 330                 335 taa                                                                1011
```

<210> SEQ ID NO 6
<211> LENGTH: 336
<212> TYPE: PRT
<213> ORGANISM: Comamonas testosteroni

<400> SEQUENCE: 6

Met Asn His Gln Ile His Ile His Asp Ser Asp Ile Ala Phe Pro Cys
1               5                   10                  15

Ala Pro Gly Gln Ser Val Leu Asp Ala Ala Leu Gln Ala Gly Ile Glu
            20                  25                  30

Leu Pro Tyr Ser Cys Arg Lys Gly Ser Cys Gly Asn Cys Ala Ser Thr
        35                  40                  45

Leu Leu Asp Gly Asn Ile Thr Ser Phe Asn Gly Met Ala Val Arg Ser
    50                  55                  60

Glu Leu Cys Thr Ser Glu Gln Val Leu Leu Cys Gly Cys Thr Ala Ala
65                  70                  75                  80

Ser Asp Ile Arg Ile Gln Pro Ser Ser Phe Arg Arg Leu Asp Pro Glu
                85                  90                  95

Ala Arg Lys Arg Phe Thr Ala Lys Val Tyr Ser Asn Thr Leu Ala Ala
            100                 105                 110

Pro Asp Val Ser Leu Leu Arg Leu Arg Leu Pro Val Gly Lys Arg Ala
        115                 120                 125

Lys Phe Glu Ala Gly Gln Tyr Leu Leu Ile His Leu Asp Gly Gly Glu
    130                 135                 140

Ser Arg Ser Tyr Ser Met Ala Asn Pro Pro His Glu Ser Asp Gly Ile
145                 150                 155                 160

Thr Leu His Ile Arg His Val Pro Gly Gly Arg Phe Ser Thr Ile Val
                165                 170                 175

Gln Gln Leu Lys Ser Gly Asp Thr Leu Asp Ile Glu Leu Pro Phe Gly
            180                 185                 190

Ser Ile Ala Leu Lys Pro Asp Asp Ser Arg Pro Leu Val Cys Val Ala
        195                 200                 205

Gly Gly Thr Gly Phe Ala Pro Ile Lys Ser Val Leu Asp Asp Leu Ala
    210                 215                 220

Lys Arg Lys Val Gln Arg Asp Ile Thr Leu Ile Trp Gly Ala Arg Asn
225                 230                 235                 240

Pro Ser Gly Leu Tyr Leu Pro Ser Ala Ile Asp Lys Trp Arg Lys Ala
                245                 250                 255

Trp Pro Gln Phe Arg Tyr Ile Ala Ala Ile Thr Asp Leu Ser Asn Val
            260                 265                 270

Pro Ala Asp Ala His Ala Gly Arg Val Asp Asp Ala Leu Arg Met His
        275                 280                 285

Phe Asp Asn Leu His Asp His Val Val His Cys Cys Gly Ser Pro Ala
    290                 295                 300

Leu Val Gln Ser Val Arg Thr Ala Ala Ser Asn Met Gly Leu Leu Ala
305                 310                 315                 320

```
Gln Asp Phe His Ala Asp Val Phe Ala Thr Asp Pro Thr Gly His His
                325                 330                 335
```

<210> SEQ ID NO 7
<211> LENGTH: 1380
<212> TYPE: DNA
<213> ORGANISM: Rhodococcus jostii
<220> FEATURE:
<221> NAME/KEY: CDS
<222> LOCATION: (1)..(1380)

<400> SEQUENCE: 7

```
atg tcc tta gca cca tcg cgc gtg aca ctg ccg gat ttc atc gat tcg        48
Met Ser Leu Ala Pro Ser Arg Val Thr Leu Pro Asp Phe Ile Asp Ser
1               5                   10                  15 cgg cca gtg agt cga tac cag tac atc gtg atc gcc ctg tgt ggg gtg        96
Arg Pro Val Ser Arg Tyr Gln Tyr Ile Val Ile Ala Leu Cys Gly Val
            20                  25                  30 gtc atg ttc atc gac ggc ttc gac acc cag agc atc agc tac atg gcg       144
Val Met Phe Ile Asp Gly Phe Asp Thr Gln Ser Ile Ser Tyr Met Ala
        35                  40                  45 ccc cac atc gcc gag gag tgg ggc ctg tcg aaa cag gtg ctc ggg ccc       192
Pro His Ile Ala Glu Glu Trp Gly Leu Ser Lys Gln Val Leu Gly Pro
    50                  55                  60 atc ttc tcc gcc gct ctc gcc ggt ctc atg gtc ggc tat ctg gcg ctc       240
Ile Phe Ser Ala Ala Leu Ala Gly Leu Met Val Gly Tyr Leu Ala Leu
65                  70                  75                  80 tcg ccg ctg tcc gag cgg ttc ggc cac cgc cgg atg atc ctc acg agc       288
Ser Pro Leu Ser Glu Arg Phe Gly His Arg Arg Met Ile Leu Thr Ser
                85                  90                  95 acg gtc atc ttc gcg ctc ggc acg ttg gcg gcg gcc tgg tca cag aac       336
Thr Val Ile Phe Ala Leu Gly Thr Leu Ala Ala Ala Trp Ser Gln Asn
            100                 105                 110 gtc acc gaa ctg atg gcg ttg cgc ttc atc acc gga atg ggg ctc ggt       384
Val Thr Glu Leu Met Ala Leu Arg Phe Ile Thr Gly Met Gly Leu Gly
        115                 120                 125 gcc gcc gcg ccg agt gcc atc gca ctg acg ggc gaa ttc agc ccc aag       432
Ala Ala Ala Pro Ser Ala Ile Ala Leu Thr Gly Glu Phe Ser Pro Lys
    130                 135                 140 cgt ctt cga gca acc ttc gtc ctg gtg atc tat tgc ggc ttc tcc ctc       480
Arg Leu Arg Ala Thr Phe Val Leu Val Ile Tyr Cys Gly Phe Ser Leu
145                 150                 155                 160 gga ttc gtc gcg gca ggg ctg gtc tcc ggt tgg ctg atc ccg atc ctc       528
Gly Phe Val Ala Ala Gly Leu Val Ser Gly Trp Leu Ile Pro Ile Leu
                165                 170                 175 ggc tgg cgg tcg gta ctc gtc gtc ggc gca gta gca ccg ctc ctc ctg       576
Gly Trp Arg Ser Val Leu Val Val Gly Ala Val Ala Pro Leu Leu Leu
            180                 185                 190 ctc ccg gcg ttg ctg cgc tac ctg ccg gac tca ctc acc tca atg atc       624
Leu Pro Ala Leu Leu Arg Tyr Leu Pro Asp Ser Leu Thr Ser Met Ile
        195                 200                 205 aac cga ggc gcg gag ccc aac aga atc cag gcg atc ttc cgc aaa atg       672
Asn Arg Gly Ala Glu Pro Asn Arg Ile Gln Ala Ile Phe Arg Lys Met
    210                 215                 220 gat ccc gcc ctc gcc gtc ggc ccc gac atc acc tac gag gcc gag aag       720
Asp Pro Ala Leu Ala Val Gly Pro Asp Ile Thr Tyr Glu Ala Glu Lys
225                 230                 235                 240 cgg acc gac gga caa cgc act gca ctg agg agc ctg ttc acc cgt gac       768
Arg Thr Asp Gly Gln Arg Thr Ala Leu Arg Ser Leu Phe Thr Arg Asp
                245                 250                 255
```

| | | | | | | | | | | | | | | | |
|---|---|---|---|---|---|---|---|---|---|---|---|---|---|---|---|
| cgg | gtc | ttg | gga | acc | ctg | ctg | ctg | tgg | ctg | gtc | ttc | gtc | atc | aac | ctc | 816 |
| Arg | Val | Leu | Gly | Thr | Leu | Leu | Leu | Trp | Leu | Val | Phe | Val | Ile | Asn | Leu | |
| | | | 260 | | | | | 265 | | | | | 270 | | | |

| ggc | gag | ttt | tac | gcg | ctg | cag | agc | tgg | cta | ccg | tcg | atc | atg | acg | agc | 864 |
|---|---|---|---|---|---|---|---|---|---|---|---|---|---|---|---|---|
| Gly | Glu | Phe | Tyr | Ala | Leu | Gln | Ser | Trp | Leu | Pro | Ser | Ile | Met | Thr | Ser | |
| | | 275 | | | | | 280 | | | | | 285 | | | | |

| ctg | gac | tac | gac | atg | ggt | acg | gtg | gtc | acc | gcc | acc | acc | ctc | acg | act | 912 |
|---|---|---|---|---|---|---|---|---|---|---|---|---|---|---|---|---|
| Leu | Asp | Tyr | Asp | Met | Gly | Thr | Val | Val | Thr | Ala | Thr | Thr | Leu | Thr | Thr | |
| | 290 | | | | | 295 | | | | | 300 | | | | | |

| gtc | ggc | ggc | atc | gcc | gct | gca | ttt | gtc | acc | ggg | ccc | tgt | atg | gac | cga | 960 |
|---|---|---|---|---|---|---|---|---|---|---|---|---|---|---|---|---|
| Val | Gly | Gly | Ile | Ala | Ala | Ala | Phe | Val | Thr | Gly | Pro | Cys | Met | Asp | Arg | |
| 305 | | | | | 310 | | | | | 315 | | | | | 320 | |

| ctc | ggc | gcg | tac | gtc | acc | ctc | gga | acc | gtt | tat | gtc | gtc | gga | ttc | gca | 1008 |
|---|---|---|---|---|---|---|---|---|---|---|---|---|---|---|---|---|
| Leu | Gly | Ala | Tyr | Val | Thr | Leu | Gly | Thr | Val | Tyr | Val | Val | Gly | Phe | Ala | |
| | | | 325 | | | | | 330 | | | | | 335 | | | |

| ttc | gtt | gcg | ctg | acc | ggt | gtc | gcc | ttt | acg | gcg | ccg | ttg | tgg | gtc | cta | 1056 |
|---|---|---|---|---|---|---|---|---|---|---|---|---|---|---|---|---|
| Phe | Val | Ala | Leu | Thr | Gly | Val | Ala | Phe | Thr | Ala | Pro | Leu | Trp | Val | Leu | |
| | | | 340 | | | | | 345 | | | | | 350 | | | |

| ttg | acg | gcc | aat | ttt | ttt | gcg | ggg | gtc | tgc | atc | agc | ggt | gga | cag | aag | 1104 |
|---|---|---|---|---|---|---|---|---|---|---|---|---|---|---|---|---|
| Leu | Thr | Ala | Asn | Phe | Phe | Ala | Gly | Val | Cys | Ile | Ser | Gly | Gly | Gln | Lys | |
| | | 355 | | | | | 360 | | | | | 365 | | | | |

| agc | ctc | atc | gcg | ctg | tcc | gcg | gtg | ttc | tat | ccg | aca | ccg | atg | cgg | tcc | 1152 |
|---|---|---|---|---|---|---|---|---|---|---|---|---|---|---|---|---|
| Ser | Leu | Ile | Ala | Leu | Ser | Ala | Val | Phe | Tyr | Pro | Thr | Pro | Met | Arg | Ser | |
| 370 | | | | | 375 | | | | | 380 | | | | | | |

| acc | ggg | gtt | gga | tgg | gcg | ttg | ggt | gtt | ggc | cgc | ctc | ggc | ggc | atc | gtc | 1200 |
|---|---|---|---|---|---|---|---|---|---|---|---|---|---|---|---|---|
| Thr | Gly | Val | Gly | Trp | Ala | Leu | Gly | Val | Gly | Arg | Leu | Gly | Gly | Ile | Val | |
| 385 | | | | 390 | | | | | 395 | | | | | 400 | | |

| ggg | ccg | atc | gcg | gtc | gga | gcg | gca | ctc | ggc | atg | ggc | tgg | tcc | gcc | agt | 1248 |
|---|---|---|---|---|---|---|---|---|---|---|---|---|---|---|---|---|
| Gly | Pro | Ile | Ala | Val | Gly | Ala | Ala | Leu | Gly | Met | Gly | Trp | Ser | Ala | Ser | |
| | | | 405 | | | | | 410 | | | | | 415 | | | |

| gca | gtc | ttc | tac | gca | atg | tca | gtc | ccc | atg | ctc | gtc | gcc | gga | gct | gcg | 1296 |
|---|---|---|---|---|---|---|---|---|---|---|---|---|---|---|---|---|
| Ala | Val | Phe | Tyr | Ala | Met | Ser | Val | Pro | Met | Leu | Val | Ala | Gly | Ala | Ala | |
| | | | 420 | | | | | 425 | | | | | 430 | | | |

| gtc | ttc | ctc | ctc | ggc | cgc | tgg | gtc | cga | agc | gac | aat | cac | ccc | gat | cgc | 1344 |
|---|---|---|---|---|---|---|---|---|---|---|---|---|---|---|---|---|
| Val | Phe | Leu | Leu | Gly | Arg | Trp | Val | Arg | Ser | Asp | Asn | His | Pro | Asp | Arg | |
| | | | 435 | | | | | 440 | | | | | 445 | | | |

| aag | tcg | gca | gaa | agt | cat | tcg | ctc | gcc | cgc | aag | tag | | | | | 1380 |
|---|---|---|---|---|---|---|---|---|---|---|---|---|---|---|---|---|
| Lys | Ser | Ala | Glu | Ser | His | Ser | Leu | Ala | Arg | Lys | | | | | | |
| | | 450 | | | | | 455 | | | | | | | | | |

```
<210> SEQ ID NO 8
<211> LENGTH: 459
<212> TYPE: PRT
<213> ORGANISM: Rhodococcus jostii

<400> SEQUENCE: 8

Met Ser Leu Ala Pro Ser Arg Val Thr Leu Pro Asp Phe Ile Asp Ser
1               5                   10                  15

Arg Pro Val Ser Arg Tyr Gln Tyr Ile Val Ile Ala Leu Cys Gly Val
            20                  25                  30

Val Met Phe Ile Asp Gly Phe Asp Thr Gln Ser Ile Ser Tyr Met Ala
        35                  40                  45

Pro His Ile Ala Glu Glu Trp Gly Leu Ser Lys Gln Val Leu Gly Pro
    50                  55                  60

Ile Phe Ser Ala Ala Leu Ala Gly Leu Met Val Gly Tyr Leu Ala Leu
65                  70                  75                  80

Ser Pro Leu Ser Glu Arg Phe Gly His Arg Arg Met Ile Leu Thr Ser
                85                  90                  95
```

Thr Val Ile Phe Ala Leu Gly Thr Leu Ala Ala Ala Trp Ser Gln Asn
            100                 105                 110

Val Thr Glu Leu Met Ala Leu Arg Phe Ile Thr Gly Met Gly Leu Gly
        115                 120                 125

Ala Ala Ala Pro Ser Ala Ile Ala Leu Thr Gly Glu Phe Ser Pro Lys
    130                 135                 140

Arg Leu Arg Ala Thr Phe Val Leu Val Ile Tyr Cys Gly Phe Ser Leu
145                 150                 155                 160

Gly Phe Val Ala Ala Gly Leu Val Ser Gly Trp Leu Ile Pro Ile Leu
                165                 170                 175

Gly Trp Arg Ser Val Leu Val Val Gly Ala Val Ala Pro Leu Leu Leu
            180                 185                 190

Leu Pro Ala Leu Leu Arg Tyr Leu Pro Asp Ser Leu Thr Ser Met Ile
        195                 200                 205

Asn Arg Gly Ala Glu Pro Asn Arg Ile Gln Ala Ile Phe Arg Lys Met
    210                 215                 220

Asp Pro Ala Leu Ala Val Gly Pro Asp Ile Thr Tyr Glu Ala Glu Lys
225                 230                 235                 240

Arg Thr Asp Gly Gln Arg Thr Ala Leu Arg Ser Leu Phe Thr Arg Asp
                245                 250                 255

Arg Val Leu Gly Thr Leu Leu Leu Trp Leu Val Phe Val Ile Asn Leu
            260                 265                 270

Gly Glu Phe Tyr Ala Leu Gln Ser Trp Leu Pro Ser Ile Met Thr Ser
        275                 280                 285

Leu Asp Tyr Asp Met Gly Thr Val Val Thr Ala Thr Thr Leu Thr Thr
    290                 295                 300

Val Gly Gly Ile Ala Ala Ala Phe Val Thr Gly Pro Cys Met Asp Arg
305                 310                 315                 320

Leu Gly Ala Tyr Val Thr Leu Gly Thr Val Tyr Val Val Gly Phe Ala
                325                 330                 335

Phe Val Ala Leu Thr Gly Val Ala Phe Thr Ala Pro Leu Trp Val Leu
            340                 345                 350

Leu Thr Ala Asn Phe Phe Ala Gly Val Cys Ile Ser Gly Gly Gln Lys
        355                 360                 365

Ser Leu Ile Ala Leu Ser Ala Val Phe Tyr Pro Thr Pro Met Arg Ser
    370                 375                 380

Thr Gly Val Gly Trp Ala Leu Gly Val Gly Arg Leu Gly Gly Ile Val
385                 390                 395                 400

Gly Pro Ile Ala Val Gly Ala Ala Leu Gly Met Gly Trp Ser Ala Ser
                405                 410                 415

Ala Val Phe Tyr Ala Met Ser Val Pro Met Leu Val Ala Gly Ala Ala
            420                 425                 430

Val Phe Leu Leu Gly Arg Trp Val Arg Ser Asp Asn His Pro Asp Arg
        435                 440                 445

Lys Ser Ala Glu Ser His Ser Leu Ala Arg Lys
    450                 455

<210> SEQ ID NO 9
<211> LENGTH: 948
<212> TYPE: DNA
<213> ORGANISM: Comamonas testosteroni
<220> FEATURE:
<221> NAME/KEY: CDS
<222> LOCATION: (1)..(948)

<400> SEQUENCE: 9

| | | | | | | | | | | | | | | | | |
|---|---|---|---|---|---|---|---|---|---|---|---|---|---|---|---|---|
| atg | aca | ata | gtg | cac | cgt | aga | ttg | gct | ttg | gcc | atc | ggc | gat | ccc | cac | 48 |
| Met | Thr | Ile | Val | His | Arg | Arg | Leu | Ala | Leu | Ala | Ile | Gly | Asp | Pro | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | att | ggc | cca | gaa | atc | gca | ctg | aaa | gct | ctt | cag | cag | ttg | tct | gcc | 96 |
| Gly | Ile | Gly | Pro | Glu | Ile | Ala | Leu | Lys | Ala | Leu | Gln | Gln | Leu | Ser | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | gaa | aga | tcc | ctg | atc | aag | gtc | tat | gga | ccg | tgg | agc | gct | ctt | gaa | 144 |
| Thr | Glu | Arg | Ser | Leu | Ile | Lys | Val | Tyr | Gly | Pro | Trp | Ser | Ala | Leu | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| caa | gca | gcg | cag | atc | tgc | caa | atg | gag | tcc | ctt | ctt | caa | gac | ctc | att | 192 |
| Gln | Ala | Ala | Gln | Ile | Cys | Gln | Met | Glu | Ser | Leu | Leu | Gln | Asp | Leu | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| cat | gag | gaa | gcc | ggc | tcg | ctt | gca | caa | cca | gtg | caa | tgc | gga | gag | atc | 240 |
| His | Glu | Glu | Ala | Gly | Ser | Leu | Ala | Gln | Pro | Val | Gln | Cys | Gly | Glu | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| acc | ccg | cag | gca | ggc | cta | tcc | acg | gtg | caa | tcc | gca | aca | gca | gcc | atc | 288 |
| Thr | Pro | Gln | Ala | Gly | Leu | Ser | Thr | Val | Gln | Ser | Ala | Thr | Ala | Ala | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| cgg | gcg | tgc | gaa | agc | ggc | gag | gtc | gat | gcc | gtc | att | gcc | tgc | ccc | cac | 336 |
| Arg | Ala | Cys | Glu | Ser | Gly | Glu | Val | Asp | Ala | Val | Ile | Ala | Cys | Pro | His | |
| | | | | 100 | | | | | 105 | | | | | 110 | | |

| | | | | | | | | | | | | | | | | |
|---|---|---|---|---|---|---|---|---|---|---|---|---|---|---|---|---|
| cat | gag | acg | gcc | att | cac | cgt | gca | ggc | ata | gcg | ttc | agc | ggc | tac | cca | 384 |
| His | Glu | Thr | Ala | Ile | His | Arg | Ala | Gly | Ile | Ala | Phe | Ser | Gly | Tyr | Pro | |
| | | | 115 | | | | | 120 | | | | | 125 | | | |

| | | | | | | | | | | | | | | | | |
|---|---|---|---|---|---|---|---|---|---|---|---|---|---|---|---|---|
| tct | ttg | ctc | gcc | aat | gtt | ctt | ggc | atg | aac | gaa | gac | gag | gta | ttc | ctg | 432 |
| Ser | Leu | Leu | Ala | Asn | Val | Leu | Gly | Met | Asn | Glu | Asp | Glu | Val | Phe | Leu | |
| | | 130 | | | | | 135 | | | | | 140 | | | | |

| | | | | | | | | | | | | | | | | |
|---|---|---|---|---|---|---|---|---|---|---|---|---|---|---|---|---|
| atg | ctg | gta | ggg | gct | gga | ctg | cgc | atc | gtg | cat | gtc | acc | ttg | cat | gag | 480 |
| Met | Leu | Val | Gly | Ala | Gly | Leu | Arg | Ile | Val | His | Val | Thr | Leu | His | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agc | gtg | cgt | agc | gca | cta | gag | cgg | ctc | tca | cct | cag | ttg | gtt | atc | aac | 528 |
| Ser | Val | Arg | Ser | Ala | Leu | Glu | Arg | Leu | Ser | Pro | Gln | Leu | Val | Ile | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| gcg | gtg | gat | gcc | gcc | gtg | cag | aca | tgc | acc | cta | ctc | ggg | gtg | cct | aaa | 576 |
| Ala | Val | Asp | Ala | Ala | Val | Gln | Thr | Cys | Thr | Leu | Leu | Gly | Val | Pro | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| ccg | caa | gtc | gct | gta | ttc | ggg | atc | aac | cct | cat | gca | tcc | gaa | gga | cag | 624 |
| Pro | Gln | Val | Ala | Val | Phe | Gly | Ile | Asn | Pro | His | Ala | Ser | Glu | Gly | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| ttg | ttc | ggc | ctg | gag | gac | tcg | cag | atc | acc | gtt | cct | gcc | gtc | gag | aca | 672 |
| Leu | Phe | Gly | Leu | Glu | Asp | Ser | Gln | Ile | Thr | Val | Pro | Ala | Val | Glu | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| ctg | cgc | aag | cgc | ggc | ctg | acg | gta | gac | ggc | ccc | atg | gga | gca | gac | atg | 720 |
| Leu | Arg | Lys | Arg | Gly | Leu | Thr | Val | Asp | Gly | Pro | Met | Gly | Ala | Asp | Met | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtt | ctg | gca | cag | cgc | aag | cac | gac | ttg | tat | gtg | gcc | atg | ctg | cat | gac | 768 |
| Val | Leu | Ala | Gln | Arg | Lys | His | Asp | Leu | Tyr | Val | Ala | Met | Leu | His | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| caa | ggg | cac | att | ccc | atc | aag | ctg | ctg | gct | cct | aac | gga | gcc | agt | gcg | 816 |
| Gln | Gly | His | Ile | Pro | Ile | Lys | Leu | Leu | Ala | Pro | Asn | Gly | Ala | Ser | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| ctc | tcc | atc | ggc | ggc | agg | gtg | gtg | ctt | tcc | agc | gtg | ggc | cat | ggc | agc | 864 |
| Leu | Ser | Ile | Gly | Gly | Arg | Val | Val | Leu | Ser | Ser | Val | Gly | His | Gly | Ser | |
| | | 275 | | | | | 280 | | | | | 285 | | | | |

| | | | | | | | | | | | | | | | | |
|---|---|---|---|---|---|---|---|---|---|---|---|---|---|---|---|---|
| gcc | atg | gac | att | gcc | ggc | cgt | ggc | gtg | gct | gac | gcc | acg | gcc | ctc | cta | 912 |
| Ala | Met | Asp | Ile | Ala | Gly | Arg | Gly | Val | Ala | Asp | Ala | Thr | Ala | Leu | Leu | |
| | 290 | | | | | 295 | | | | | 300 | | | | | |

```
cgc aca atc gcc cta ctc gga gcc caa ccg gtc tga                948
Arg Thr Ile Ala Leu Leu Gly Ala Gln Pro Val
305                 310                 315
```

<210> SEQ ID NO 10
<211> LENGTH: 315
<212> TYPE: PRT
<213> ORGANISM: Comamonas testosteroni

<400> SEQUENCE: 10

```
Met Thr Ile Val His Arg Arg Leu Ala Leu Ala Ile Gly Asp Pro His
1               5                   10                  15

Gly Ile Gly Pro Glu Ile Ala Leu Lys Ala Leu Gln Gln Leu Ser Ala
            20                  25                  30

Thr Glu Arg Ser Leu Ile Lys Val Tyr Gly Pro Trp Ser Ala Leu Glu
        35                  40                  45

Gln Ala Ala Gln Ile Cys Gln Met Glu Ser Leu Leu Gln Asp Leu Ile
    50                  55                  60

His Glu Glu Ala Gly Ser Leu Ala Gln Pro Val Gln Cys Gly Glu Ile
65                  70                  75                  80

Thr Pro Gln Ala Gly Leu Ser Thr Val Gln Ser Ala Thr Ala Ala Ile
                85                  90                  95

Arg Ala Cys Glu Ser Gly Glu Val Asp Ala Val Ile Ala Cys Pro His
            100                 105                 110

His Glu Thr Ala Ile His Arg Ala Gly Ile Ala Phe Ser Gly Tyr Pro
        115                 120                 125

Ser Leu Leu Ala Asn Val Leu Gly Met Asn Glu Asp Glu Val Phe Leu
    130                 135                 140

Met Leu Val Gly Ala Gly Leu Arg Ile Val His Val Thr Leu His Glu
145                 150                 155                 160

Ser Val Arg Ser Ala Leu Glu Arg Leu Ser Pro Gln Leu Val Ile Asn
                165                 170                 175

Ala Val Asp Ala Ala Val Gln Thr Cys Thr Leu Leu Gly Val Pro Lys
            180                 185                 190

Pro Gln Val Ala Val Phe Gly Ile Asn Pro His Ala Ser Glu Gly Gln
        195                 200                 205

Leu Phe Gly Leu Glu Asp Ser Gln Ile Thr Val Pro Ala Val Glu Thr
    210                 215                 220

Leu Arg Lys Arg Gly Leu Thr Val Asp Gly Pro Met Gly Ala Asp Met
225                 230                 235                 240

Val Leu Ala Gln Arg Lys His Asp Leu Tyr Val Ala Met Leu His Asp
                245                 250                 255

Gln Gly His Ile Pro Ile Lys Leu Leu Ala Pro Asn Gly Ala Ser Ala
            260                 265                 270

Leu Ser Ile Gly Gly Arg Val Val Leu Ser Ser Val Gly His Gly Ser
        275                 280                 285

Ala Met Asp Ile Ala Gly Arg Val Ala Asp Ala Thr Ala Leu Leu
    290                 295                 300

Arg Thr Ile Ala Leu Leu Gly Ala Gln Pro Val
305                 310                 315
```

<210> SEQ ID NO 11
<211> LENGTH: 1188
<212> TYPE: DNA
<213> ORGANISM: Corynebacterium glutamicum ATCC13032

<220> FEATURE:
<221> NAME/KEY: CDS
<222> LOCATION: (1)..(1188)

<400> SEQUENCE: 11

| | | | | | | | | | | | | | | | | |
|---|---|---|---|---|---|---|---|---|---|---|---|---|---|---|---|---|
| atg | aac | cac | gta | cca | gtg | gca | att | att | ggc | gca | gga | cca | gca | gga | cta | 48 |
| Met | Asn | His | Val | Pro | Val | Ala | Ile | Ile | Gly | Ala | Gly | Pro | Ala | Gly | Leu | |
| 1 | | | | 5 | | | | | 10 | | | | | 15 | | |
| acc | ctc | gcc | cac | ctc | ctc | cac | ctt | caa | ggt | gtg | gaa | tca | atc | gtc | ttt | 96 |
| Thr | Leu | Ala | His | Leu | Leu | His | Leu | Gln | Gly | Val | Glu | Ser | Ile | Val | Phe | |
| | | | 20 | | | | | 25 | | | | | 30 | | | |
| gaa | tcc | cgc | acc | cgc | aag | gac | gtc | gaa | gaa | acc | gtc | cga | gca | ggc | atc | 144 |
| Glu | Ser | Arg | Thr | Arg | Lys | Asp | Val | Glu | Glu | Thr | Val | Arg | Ala | Gly | Ile | |
| | | 35 | | | | | 40 | | | | | 45 | | | | |
| ctg | gaa | caa | ggc | acc | ctg | aat | ctg | atg | cgc | gaa | acc | gga | gtc | ggc | gca | 192 |
| Leu | Glu | Gln | Gly | Thr | Leu | Asn | Leu | Met | Arg | Glu | Thr | Gly | Val | Gly | Ala | |
| 50 | | | | | 55 | | | | | 60 | | | | | | |
| cgc | atg | gaa | gca | gaa | gcc | gat | cac | gat | gaa | gca | atc | gac | atc | tcc | atc | 240 |
| Arg | Met | Glu | Ala | Glu | Ala | Asp | His | Asp | Glu | Ala | Ile | Asp | Ile | Ser | Ile | |
| 65 | | | | | 70 | | | | | 75 | | | | | 80 | |
| aac | aat | gag | cgc | acc | cgc | att | ccg | ctg | acc | gaa | ctc | acc | ggc | cac | aag | 288 |
| Asn | Asn | Glu | Arg | Thr | Arg | Ile | Pro | Leu | Thr | Glu | Leu | Thr | Gly | His | Lys | |
| | | | | 85 | | | | | 90 | | | | | 95 | | |
| gtt | gcg | atc | tac | ccg | cag | cac | gaa | tac | ctc | aaa | gat | ttc | att | gcc | aag | 336 |
| Val | Ala | Ile | Tyr | Pro | Gln | His | Glu | Tyr | Leu | Lys | Asp | Phe | Ile | Ala | Lys | |
| | | | 100 | | | | | 105 | | | | | 110 | | | |
| cgc | atc | gaa | gat | ggc | ggc | gaa | ctc | ctt | ttc | acc | acc | act | gtt | gat | tcc | 384 |
| Arg | Ile | Glu | Asp | Gly | Gly | Glu | Leu | Leu | Phe | Thr | Thr | Thr | Val | Asp | Ser | |
| | | 115 | | | | | 120 | | | | | 125 | | | | |
| gta | gaa | aac | tac | gaa | ggc | gac | ctc | gcc | aag | gtg | acc | tac | acc | gaa | gcc | 432 |
| Val | Glu | Asn | Tyr | Glu | Gly | Asp | Leu | Ala | Lys | Val | Thr | Tyr | Thr | Glu | Ala | |
| 130 | | | | | 135 | | | | | 140 | | | | | | |
| gat | ggt | tcc | tcc | acc | acc | atc | acc | gcc | gac | tac | gtc | atc | gca | gct | gac | 480 |
| Asp | Gly | Ser | Ser | Thr | Thr | Ile | Thr | Ala | Asp | Tyr | Val | Ile | Ala | Ala | Asp | |
| 145 | | | | | 150 | | | | | 155 | | | | | 160 | |
| ggc | tcc | aac | tcc | cct | tac | cgc | aag | ctg | atc | acc | gaa | gac | ggt | ggc | gtg | 528 |
| Gly | Ser | Asn | Ser | Pro | Tyr | Arg | Lys | Leu | Ile | Thr | Glu | Asp | Gly | Gly | Val | |
| | | | | 165 | | | | | 170 | | | | | 175 | | |
| cgc | gcc | cgc | cat | gaa | tac | cct | tac | gca | tgg | ttc | ggc | att | ttg | gtg | gaa | 576 |
| Arg | Ala | Arg | His | Glu | Tyr | Pro | Tyr | Ala | Trp | Phe | Gly | Ile | Leu | Val | Glu | |
| | | | 180 | | | | | 185 | | | | | 190 | | | |
| gca | cca | aaa | acc | caa | aag | gaa | ctc | atc | tac | gca | acc | cac | cct | gag | ggc | 624 |
| Ala | Pro | Lys | Thr | Gln | Lys | Glu | Leu | Ile | Tyr | Ala | Thr | His | Pro | Glu | Gly | |
| | | 195 | | | | | 200 | | | | | 205 | | | | |
| ttt | gcg | ctg | atc | tcc | acc | cgt | acc | gat | gaa | atc | cag | cgc | tac | tac | ctg | 672 |
| Phe | Ala | Leu | Ile | Ser | Thr | Arg | Thr | Asp | Glu | Ile | Gln | Arg | Tyr | Tyr | Leu | |
| 210 | | | | | 215 | | | | | 220 | | | | | | |
| cag | tgc | aac | cct | gac | gac | acc | cca | gac | atg | tgg | ccc | gat | gac | cgc | att | 720 |
| Gln | Cys | Asn | Pro | Asp | Asp | Thr | Pro | Asp | Met | Trp | Pro | Asp | Asp | Arg | Ile | |
| 225 | | | | | 230 | | | | | 235 | | | | | 240 | |
| tgg | gaa | cag | ctg | cac | ctg | cgt | gcg | gac | tcc | cct | ggc | atc | acc | gtg | tct | 768 |
| Trp | Glu | Gln | Leu | His | Leu | Arg | Ala | Asp | Ser | Pro | Gly | Ile | Thr | Val | Ser | |
| | | | | 245 | | | | | 250 | | | | | 255 | | |
| gaa | ggg | cgc | atc | ttt | gac | aag | gcc | gtg | ctg | cgt | ttc | cgc | tcc | gcg | gtc | 816 |
| Glu | Gly | Arg | Ile | Phe | Asp | Lys | Ala | Val | Leu | Arg | Phe | Arg | Ser | Ala | Val | |
| | | | 260 | | | | | 265 | | | | | 270 | | | |
| acc | gaa | cca | atg | caa | aag | gga | cgc | ctc | ttc | ctt | gct | ggc | gat | gct | gca | 864 |
| Thr | Glu | Pro | Met | Gln | Lys | Gly | Arg | Leu | Phe | Leu | Ala | Gly | Asp | Ala | Ala | |
| | | 275 | | | | | 280 | | | | | 285 | | | | |

-continued

```
cac acc gtg ccg cca acc gga gct aag ggc ctc aac ttg gct gtt gcc    912
His Thr Val Pro Pro Thr Gly Ala Lys Gly Leu Asn Leu Ala Val Ala
    290             295                 300 gat gtc tca gta ctc gcg cca gca ctg gtt cgt gcc ctg aag aag aag    960
Asp Val Ser Val Leu Ala Pro Ala Leu Val Arg Ala Leu Lys Lys Lys
305                 310                 315                 320 gac acc ggc ttg ctc gat agc tac acc tcc ctg gca gtc ccc cgc atc   1008
Asp Thr Gly Leu Leu Asp Ser Tyr Thr Ser Leu Ala Val Pro Arg Ile
                325                 330                 335 tgg aaa gca cag cac ttc tcc tac tgg atg agc tcc atg ctc cac gca   1056
Trp Lys Ala Gln His Phe Ser Tyr Trp Met Ser Ser Met Leu His Ala
            340                 345                 350 gta ccc ggc gaa gat cac ttt gcc acc cag cgc cga ttc gct gaa ttg   1104
Val Pro Gly Glu Asp His Phe Ala Thr Gln Arg Arg Phe Ala Glu Leu
        355                 360                 365 cgc tcc gtc cta gaa tcc caa tcc ggc caa cgc tac ctc gca gag cag   1152
Arg Ser Val Leu Glu Ser Gln Ser Gly Gln Arg Tyr Leu Ala Glu Gln
370                 375                 380 ttc gtt ggg cgc gac cta cca cgc ttc gag gta taa                   1188
Phe Val Gly Arg Asp Leu Pro Arg Phe Glu Val
385                 390                 395
```

<210> SEQ ID NO 12
<211> LENGTH: 395
<212> TYPE: PRT
<213> ORGANISM: Corynebacterium glutamicum ATCC13032

<400> SEQUENCE: 12

```
Met Asn His Val Pro Val Ala Ile Ile Gly Ala Gly Pro Ala Gly Leu
1               5                   10                  15

Thr Leu Ala His Leu Leu His Leu Gln Gly Val Glu Ser Ile Val Phe
            20                  25                  30

Glu Ser Arg Thr Arg Lys Asp Val Glu Glu Thr Val Arg Ala Gly Ile
        35                  40                  45

Leu Glu Gln Gly Thr Leu Asn Leu Met Arg Glu Thr Gly Val Gly Ala
    50                  55                  60

Arg Met Glu Ala Glu Ala Asp His Asp Glu Ala Ile Asp Ile Ser Ile
65                  70                  75                  80

Asn Asn Glu Arg Thr Arg Ile Pro Leu Thr Glu Leu Thr Gly His Lys
                85                  90                  95

Val Ala Ile Tyr Pro Gln His Glu Tyr Leu Lys Asp Phe Ile Ala Lys
            100                 105                 110

Arg Ile Glu Asp Gly Gly Glu Leu Leu Phe Thr Thr Thr Val Asp Ser
        115                 120                 125

Val Glu Asn Tyr Glu Gly Asp Leu Ala Lys Val Thr Tyr Thr Glu Ala
    130                 135                 140

Asp Gly Ser Ser Thr Thr Ile Thr Ala Asp Tyr Val Ile Ala Ala Asp
145                 150                 155                 160

Gly Ser Asn Ser Pro Tyr Arg Lys Leu Ile Thr Glu Asp Gly Gly Val
                165                 170                 175

Arg Ala Arg His Glu Tyr Pro Tyr Ala Trp Phe Gly Ile Leu Val Glu
            180                 185                 190

Ala Pro Lys Thr Gln Lys Glu Leu Ile Tyr Ala Thr His Pro Glu Gly
        195                 200                 205

Phe Ala Leu Ile Ser Thr Arg Thr Asp Glu Ile Gln Arg Tyr Tyr Leu
    210                 215                 220
```

Gln Cys Asn Pro Asp Asp Thr Pro Asp Met Trp Pro Asp Asp Arg Ile
225                 230                 235                 240

Trp Glu Gln Leu His Leu Arg Ala Asp Ser Pro Gly Ile Thr Val Ser
            245                 250                 255

Glu Gly Arg Ile Phe Asp Lys Ala Val Leu Arg Phe Arg Ser Ala Val
        260                 265                 270

Thr Glu Pro Met Gln Lys Gly Arg Leu Phe Leu Ala Gly Asp Ala Ala
    275                 280                 285

His Thr Val Pro Pro Thr Gly Ala Lys Gly Leu Asn Leu Ala Val Ala
290                 295                 300

Asp Val Ser Val Leu Ala Pro Ala Leu Val Arg Ala Leu Lys Lys Lys
305                 310                 315                 320

Asp Thr Gly Leu Leu Asp Ser Tyr Thr Ser Leu Ala Val Pro Arg Ile
            325                 330                 335

Trp Lys Ala Gln His Phe Ser Tyr Trp Met Ser Ser Met Leu His Ala
        340                 345                 350

Val Pro Gly Glu Asp His Phe Ala Thr Gln Arg Arg Phe Ala Glu Leu
    355                 360                 365

Arg Ser Val Leu Glu Ser Gln Ser Gly Gln Arg Tyr Leu Ala Glu Gln
370                 375                 380

Phe Val Gly Arg Asp Leu Pro Arg Phe Glu Val
385                 390                 395

<210> SEQ ID NO 13
<211> LENGTH: 33
<212> TYPE: DNA
<213> ORGANISM: Artificial
<220> FEATURE:
<223> OTHER INFORMATION: Synthetic DNA

<400> SEQUENCE: 13
cgagctcgaa ttcgcggccg ctaatagtac ctg                                33

<210> SEQ ID NO 14
<211> LENGTH: 33
<212> TYPE: DNA
<213> ORGANISM: Artificial
<220> FEATURE:
<223> OTHER INFORMATION: Sythetic DNA

<400> SEQUENCE: 14
tgaagtgaaa aatggcgcac attgtgcgac att                                33

<210> SEQ ID NO 15
<211> LENGTH: 37
<212> TYPE: DNA
<213> ORGANISM: Artificial
<220> FEATURE:
<223> OTHER INFORMATION: Synthetic DNA

<400> SEQUENCE: 15 tttttttgtct gccgtttacc ggcgcgccgc gatcgcc                           37

<210> SEQ ID NO 16
<211> LENGTH: 37
<212> TYPE: DNA
<213> ORGANISM: Artificial
<220> FEATURE:
<223> OTHER INFORMATION: Synthetic DNA

<400> SEQUENCE: 16
aattggcgat cgcggcgcgc cggtaaacgg cagacaa          37

<210> SEQ ID NO 17
<211> LENGTH: 32
<212> TYPE: DNA
<213> ORGANISM: Artificial
<220> FEATURE:
<223> OTHER INFORMATION: Synthetic DNA

<400> SEQUENCE: 17
aaaaaatgtc gcacaatgtg cgccattttt ca               32

<210> SEQ ID NO 18
<211> LENGTH: 42
<212> TYPE: DNA
<213> ORGANISM: Artificial
<220> FEATURE:
<223> OTHER INFORMATION: Synthetic DNA

<400> SEQUENCE: 18
cttcacaggt actattagcg gccgcgaatt cgagctcggt ac    42

<210> SEQ ID NO 19
<211> LENGTH: 38
<212> TYPE: DNA
<213> ORGANISM: Artificial
<220> FEATURE:
<223> OTHER INFORMATION: Synthetic DNA

<400> SEQUENCE: 19
tggccggcct gcaggtaata cgactcacta tagggttc         38

<210> SEQ ID NO 20
<211> LENGTH: 41
<212> TYPE: DNA
<213> ORGANISM: Artificial
<220> FEATURE:
<223> OTHER INFORMATION: Synthetic DNA

<400> SEQUENCE: 20
ctggcgttac ctaaggagat ctaaattatg actaatataa a     41

<210> SEQ ID NO 21
<211> LENGTH: 39
<212> TYPE: DNA
<213> ORGANISM: Artificial
<220> FEATURE:
<223> OTHER INFORMATION: Synthetic DNA

<400> SEQUENCE: 21
taaggaggtc cttaattaat aagcttgcat gcctgcagg        39

<210> SEQ ID NO 22
<211> LENGTH: 37
<212> TYPE: DNA
<213> ORGANISM: Artificial
<220> FEATURE:
<223> OTHER INFORMATION: Synthetic DNA

<400> SEQUENCE: 22
tcgacctgca ggcatgcaag cttattaatt aaggacc          37

<210> SEQ ID NO 23
<211> LENGTH: 42
<212> TYPE: DNA
<213> ORGANISM: Artificial
<220> FEATURE:
<223> OTHER INFORMATION: Synthetic DNA

<400> SEQUENCE: 23
tccttattta tattagtcat aatttagatc tccttaggta ac					42

<210> SEQ ID NO 24
<211> LENGTH: 47
<212> TYPE: DNA
<213> ORGANISM: Artificial
<220> FEATURE:
<223> OTHER INFORMATION: Synthetic DNA

<400> SEQUENCE: 24
gccaggaacc ctatagtgag tcgtattacc tgcaggccgg ccacatg					47

<210> SEQ ID NO 25
<211> LENGTH: 43
<212> TYPE: DNA
<213> ORGANISM: Artificial
<220> FEATURE:
<223> OTHER INFORMATION: Synthetic DNA

<400> SEQUENCE: 25
agatctaaaa attatgaata atataaaagg aggaattaat taa					43

<210> SEQ ID NO 26
<211> LENGTH: 31
<212> TYPE: DNA
<213> ORGANISM: Artificial
<220> FEATURE:
<223> OTHER INFORMATION: Synthetic DNA

<400> SEQUENCE: 26
ttggatcctc ctttattatt gtttctgttg c					31

<210> SEQ ID NO 27
<211> LENGTH: 30
<212> TYPE: DNA
<213> ORGANISM: Artificial
<220> FEATURE:
<223> OTHER INFORMATION: Synthetic DNA

<400> SEQUENCE: 27
ttcctgcagg ttaagccact tcctttttgc					30

<210> SEQ ID NO 28
<211> LENGTH: 43
<212> TYPE: DNA
<213> ORGANISM: Artificial
<220> FEATURE:
<223> OTHER INFORMATION: Synthetic DNA

<400> SEQUENCE: 28
ggatccgcga tcgctaaatg cargaatcya tyatycartg gca					43

<210> SEQ ID NO 29
<211> LENGTH: 41
<212> TYPE: DNA
<213> ORGANISM: Artificial
<220> FEATURE:
<223> OTHER INFORMATION: Synthetic DNA

<400> SEQUENCE: 29

```
tctagagcgg ccgctagcta cttctartgg ykrccagtcg g              41
```

<210> SEQ ID NO 30
<211> LENGTH: 3667
<212> TYPE: DNA
<213> ORGANISM: Comamonas testosteroni

<400> SEQUENCE: 30

```
atgcaagaat ccattatcca gtggcatggg gccactaata cacgcgtgcc tttcggtatc     60
tacactgaca cagccaatgc tgatcaagaa cagcagcgca tctatcgcgg cgaggtctgg    120
aactacctgt gcctggaatc tgaaatcccc gaggctggtg atttccgtac tacctttgcc    180
ggtgaaacac cgatagttgt cgtacgggat gccgaccagg aaatctacgc cttcgagaac    240
cgctgcgcgc atcgcggcgc tctcatcgct ctggagaaat cgggacgtac ggatagtttc    300
cagtgcgtct atcacgcctg gagctacaac cgacagggag atctgaccgg cgttgccttc    360
gagaaaggtg tcaagggcca gggtggcatg ccggcctcat tctgcaaaga agagcatggc    420
ccgcgcaagc tccgcgtggc tgtcttttgc ggtttggtct ttggcagttt ttccgaggac    480
gtacccagca ttgaggatta ccttggccct gagatttgcg agcgcataga gcgcgtgctg    540
cacaagcccg tagaagtcat cggtcgcttc acgcaaaagc tgcctaacaa ctggaagctc    600
tacttcgaga acgtgaagga cagctatcac gccagcctcc tgcatatgtt cttcaccacc    660
ttcgagctga atcgcctctc acaaaaaggc ggagtcatcg tcgacgagtc gggtggccac    720
catgtgagct attccatgat tgatcgtagc gccaaagacg actcgtacaa ggaccaggcc    780
atccgctccg acaacgagcg ttaccggctc aaagatccca gccttctaga gggcttcgag    840
gagttcgagg acgcgtgac cctgcagatc ctttctgtgt ccctggcttt gtgctgcag    900
cagattcaga acagcatcgc cgtgcgtcag ttgttgccca agagcatctc cagctcggaa    960
ctcaactgga cctatcttgg ctatgcagat gacagtgcag agcagcgcaa ggtcagactc   1020
aaacaggcca acctcatcgg ccctgcagga tttatttcca tggaggacgg agctgtcggt   1080
ggattcgtgc agcgtggcat cgcaggcgct gccaaccttg atgcggtcat cgagatgggc   1140
ggagaccacg aaggctctag cgagggccgc gccacagaaa cctcggtacg cggcttttgg   1200
aaggcctacc gcaagcatat gggacaggag atgcaagcat gatccatgaa attcaaatcg   1260
cggccttcaa tgccgcttac gcgaagacca tagacagtga cgttatggag caatggccaa   1320
ccttcttcac gaaggattgc cattatcgcg tcaccaatgt cgacaaccat gctgaaggac   1380
ttgctgctgg cattgtctgg gcagattcgc aggacatgct caccgaccga atttctgcgc   1440
tgcgcgaagc caatatctac gagcgccacc gctatcgcca tatcctgggt ctgccttcga   1500
tccagtcagc cgatgcaaca caggccagtg cttccacgcc attcctggtg ctgcgcatca   1560
tgcataccgg ggaaacagag gtctttgcca gcggtgagta ccacgacaaa ttcaccacga   1620
tcgatggaaa gttacgtctg caagagcgcg tcgcggtttg cgacagcacg gtgacggaca   1680
cgctgatgtc attgccgcta tgacaatagt gcaccgtaga ttggctttgg ccatcggcga   1740
tccccacggc attgggccag aaatcgcact gaaagctctt cagcagttgt ctgccaccga   1800
aagatccctg atcaaggtct atggaccgtg gagcgctctt gaacaagcag cgcagatctg   1860
ccaaatggag tcccttcttc aagacctcat tcatgaggaa gccggctcgc ttgcacaacc   1920
agtgcaatgc ggagagatca cccgcaggc aggcctatcc acggtgcaat ccgcaacagc   1980
agccatccgg gcgtgcgaaa gcggcgaggt cgatgccgtc attgcctgcc cccaccatga   2040
```

```
gacggccatt caccgtgcag gcatagcgtt cagcggctac ccatctttgc tcgccaatgt   2100
tcttggcatg aacgaagacg aggtattcct gatgctggta ggggctggac tgcgcatcgt   2160
gcatgtcacc ttgcatgaga gcgtgcgtag cgcactagag cggctctcac ctcagttggt   2220
tatcaacgcg gtggatgccg ccgtgcagac atgcaccta ctcggggtgc ctaaaccgca    2280
agtcgctgta ttcgggatca accctcatgc atccgaagga cagttgttcg gcctggagga   2340
ctcgcagatc accgttcctg ccgtcgagac actgcgcaag cgcggcctga cggtagacgg   2400
ccccatggga gcagacatgg ttctggcaca gcgcaagcac gacttgtatg tggccatgct   2460
gcatgaccaa gggcacattc ccatcaagct gctggctcct aacggagcca gtgcgctctc   2520
catcggcggc agggtggtgc tttccagcgt gggccatggc agcgccatgg acattgccgg   2580
ccgtggcgtg gctgacgcca cggccctcct acgcacaatc gccctactcg gagcccaacc   2640
ggtctgagga ctctctatga accaccagat ccatatccac gactctgata tcgcgttccc   2700
ctgcgcgcct gggcaatccg tactggatgc agccctgcag gccggcatcg agctgcccta   2760
ttcctgccgc aaaggtagct gtggcaactg tgcgagtacg ctgctcgacg gaaatattac   2820
ttccttcaat ggcatggccg tgcgcagcga actctgcacc tcggagcagg tattgctgtg   2880
cggctgcacc gccgccagcg atatacgtat ccagccgagc tcctttcgcc gtctcgaccc   2940
ggaagcccgc aaacgtttta cggccaaggt gtacagcaat acactggcgg cacccgatgt   3000
ctcgctactg cgcctgcgcc tgcctgtggg caagcgcgcc aaatttgaag ccggccaata   3060
cctgctgatt cacctcgacg gcggggaaag ccgcagctac tctatggcca acccaccca    3120 tgagagcgat ggcatcacat tgcatatcag gcatgtaccg ggtggtcgct tcagcactat   3180
cgttcagcag ttgaagtctg gtgacacatt ggatatcgaa ctgccattcg gcagcatcgc   3240
gttgaagcct gacgacagca gaccccctagt ttgcgttgca ggaggcaccg gatttgcacc   3300
catcaagtcc gttctggatg acctggccaa acgaaggta cagcgcgaca tcacgctgat    3360
ttggggtgct cgcaaccccct ctggcctgta tcttcctagc gccatcgaca gtgcgcaa    3420 agcttggccg cagtttcgct acattgcagc catcactgac ctaagcaacg tgcctgcgga   3480
tgctcacgcc ggtcgggtgg atgacgcgct acgcatgcac tttgacaacc tacacgatca   3540
tgttgtccac tgctgtggct caccagccct cgttcaatct gtgcgcacag cagcctccaa   3600
tatgggcctg ctagcacaag actttcatgc ggatgtgttc gctacagacc cgactggcca   3660
ccactaa                                                             3667

<210> SEQ ID NO 31
<211> LENGTH: 48
<212> TYPE: DNA
<213> ORGANISM: Artificial
<220> FEATURE:
<223> OTHER INFORMATION: Synthetic DNA

<400> SEQUENCE: 31
aatttaatta aggaggatta ataaatgtcc ttagcaccat cgcgcgtg                 48

<210> SEQ ID NO 32
<211> LENGTH: 49
<212> TYPE: DNA
<213> ORGANISM: Artificial
<220> FEATURE:
<223> OTHER INFORMATION: Synthetic DNA

<400> SEQUENCE: 32
aagcggccgc gatcgcattc atttacttgc gggcgagcga atgactttc                49
```

<210> SEQ ID NO 33
<211> LENGTH: 37
<212> TYPE: DNA
<213> ORGANISM: Artificial
<220> FEATURE:
<223> OTHER INFORMATION: Synthetic DNA

<400> SEQUENCE: 33
ggtggttcat agcggcaatg acatcagcgt gtccgtc                          37

<210> SEQ ID NO 34
<211> LENGTH: 37
<212> TYPE: DNA
<213> ORGANISM: Artificial
<220> FEATURE:
<223> OTHER INFORMATION: Synthetic DNA

<400> SEQUENCE: 34
cattgccgct atgaaccacc agatccatat ccacgac                          37

<210> SEQ ID NO 35
<211> LENGTH: 44
<212> TYPE: DNA
<213> ORGANISM: Artificial
<220> FEATURE:
<223> OTHER INFORMATION: Synthetic DNA

<400> SEQUENCE: 35
aatttaatta aggaggataa ataaatgaac cacgtaccag tggc                  44

<210> SEQ ID NO 36
<211> LENGTH: 47
<212> TYPE: DNA
<213> ORGANISM: Artificial
<220> FEATURE:
<223> OTHER INFORMATION: Synthetic DNA

<400> SEQUENCE: 36
aagcggccgc gatcgcattc atttatacct cgaagcgtgg taggtcg               47

<210> SEQ ID NO 37
<211> LENGTH: 49
<212> TYPE: DNA
<213> ORGANISM: Artificial
<220> FEATURE:
<223> OTHER INFORMATION: Synthetic DNA

<400> SEQUENCE: 37
aattaattaa atgatggcta acagaatgct tttaaacgaa acggcatgg             49

<210> SEQ ID NO 38
<211> LENGTH: 50
<212> TYPE: DNA
<213> ORGANISM: Artificial
<220> FEATURE:
<223> OTHER INFORMATION: Synthetic DNA

<400> SEQUENCE: 38
tgcggccgct tgtttaaacc tccttatttt accaggcggt atggtaaagc            50

<210> SEQ ID NO 39
<211> LENGTH: 35
<212> TYPE: DNA
<213> ORGANISM: Artificial
<220> FEATURE:
<223> OTHER INFORMATION: Synthetic DNA

```
<400> SEQUENCE: 39
tgatttaaat ttatgagtgt acccgttcaa catcc                                  35

<210> SEQ ID NO 40
<211> LENGTH: 50
<212> TYPE: DNA
<213> ORGANISM: Artificial
<220> FEATURE:
<223> OTHER INFORMATION: Synthetic DNA

<400> SEQUENCE: 40
tgcggccgct tgtttaaacc tccttatttt aagactgtaa ataaaccacc                  50

<210> SEQ ID NO 41
<211> LENGTH: 66
<212> TYPE: DNA
<213> ORGANISM: Artificial
<220> FEATURE:
<223> OTHER INFORMATION: Synthetic DNA

<400> SEQUENCE: 41
gcggccgcga tatcgttgta aaaaccccg ctccggcggg gttttttgta tctggccagg        60
cgcgcc                                                                  66

<210> SEQ ID NO 42
<211> LENGTH: 28
<212> TYPE: DNA
<213> ORGANISM: Artificial
<220> FEATURE:
<223> OTHER INFORMATION: Synthetic DNA

<400> SEQUENCE: 42
aaggcgcgcc gtgtccggtt tgatagggg                                         28

<210> SEQ ID NO 43
<211> LENGTH: 18
<212> TYPE: DNA
<213> ORGANISM: Artificial
<220> FEATURE:
<223> OTHER INFORMATION: Synthetic DNA

<400> SEQUENCE: 43
tgtaaaacga cggccagt                                                     18
```

METHOD FOR PRODUCING USEFUL CHEMICAL SUBSTANCE FROM TEREPHTHALIC ACID POTASSIUM SALT

TECHNICAL FIELD

The present invention relates to a method of producing terephthalate 1,2-cis-dihydrodiol (hereinafter abbreviated as TPA-DHD as necessary) from terephthalic acid potassium salt as raw material using a microorganism expressing terephthalate 1,2-dioxygenase, a method of further converting TPA-DHD into protocatechuic acid or gallic acid, and a method of obtaining the potassium terephthalate that serves as the raw material by depolymerization of waste polyesters. It is to be noted that, in the present invention, the potassium terephthalate refer to a compound in which terephthalic acid in dipotassium terephthalate, 1-potassium 4-sodium terephthalate, 1-potassium 4-ammonium terephthalate, or the like forms a salt with potassium ion through at least one carboxyl group residue of the terephthalic acid.

BACKGROUND ART

Terephthalic acid is an inexpensive chemical that is produced in large quantity mainly as a raw material of terephthalic acid-based polyesters including polyethylene terephthalate (hereinafter abbreviated as PET), polytrimethylene terephthalate (hereinafter abbreviated as PTT), and polybutylene terephthalate (hereinafter abbreviated as PBT). Because terephthalic acid is inexpensive, technologies of producing useful chemicals such as TPA-DHD, 2-pyrone-4,6-dicarboxylic acid, protocatechuic acid, or gallic acid with terephthalic acid as a raw material using microorganisms have been developed (Documents 1 to 5). It has been known that 2-hydroxy terephthalic acid which is a raw material of pharmaceutical products or resin materials can be produced by a dehydration reaction of TPA-DHD (Patent Documents 1 and 2).

In cases where useful chemicals are produced with terephthalic acid as a raw material using microorganisms, it is desired to add terephthalic acid salt which are excellent in water-solubility, rather than terephthalic acid per se, to a culture medium. Because sodium hydroxide is less expensive than potassium hydroxide, sodium salts of terephthalic acid has been thus far used as the raw material. There are no reports describing production of useful chemicals with potassium salts of terephthalic acid as raw materials using microorganisms or no reports showing that the capacity of the sodium salt of terephthalic acid in production of an intended compound is superior to that of the potassium salt of terephthalic acid.

With regard to recycling of terephthalic acid-based polyesters, a number of recycling technologies have been developed in particular with focus on the recycling of waste PET bottles and are advancing toward commercialization. However, the cost for the recycling is high, and a more profitable recycling technology is demanded. As seen above, the use of terephthalic acid derived from waste polyesters as raw materials in the production of chemicals leads to solution for environment problems and to reduction of the production cost, and is therefore an important research and development issue.

As a method of recycling waste polyesters, in addition to a material recycling method whereby original polyesters are obtained, a chemical recycling method whereby terephthalic acid, bis-2-hydroxyethyl terephthalate, or the like is obtained through chemical depolymerization of polyesters is known (Patent Documents 6 to 11). It has been known that depolymerization is feasible by heating polyesters such as PET in an ethylene glycol reaction solvent or alcohol reaction solvent containing an alkali metal hydroxide such as sodium hydroxide. In this case, because sodium hydroxide is inexpensive, sodium hydroxide is in general used as the alkali metal hydroxide. Yet, because there are no usage applications of the obtained alkali metal terephthalate, it is anticipated to set forward recycling operation of further subjecting the alkali metal terephthalate to acid treatment to obtain terephthalic acid. However, such a recycling operation is hardly carried out because the production cost tends to be high and the obtained terephthalic acid is inexpensive.

Although it has been known that PET can be depolymerized in an ethylene glycol solvent containing potassium hydroxide (Non-patent Document 1), there are no reports on results of comparing difference in PET depolymerization between potassium hydroxide and sodium hydroxide in the ethylene glycol solvent. Further, there are no reports on technologies of recycling waste polyesters wherein, after PET, PTT, or PBT is depolymerized in an ethylene glycol reaction solvent containing potassium hydroxide to thereby obtain potassium terephthalates, such potassium terephthalates are converted into other useful chemicals using microorganisms.

An example of an experiment has been reported, wherein terephthalic acid is obtained by depolymerizing waste PET in a 1-butanol reaction solvent containing sodium hydroxide and adding sulfuric acid (Patent Document 12). Yet, there are no reports where waste PET is depolymerized in the 1-butanol reaction solvent containing potassium hydroxide, and where difference in a reaction of depolymerizing polyester in the 1-butanol reaction solvent containing alkali is compared between potassium hydroxide and sodium hydroxide.

In cases where waste polyesters are depolymerized in ethylene glycol containing potassium hydroxide, if an attempt to obtain potassium terephthalate with high purity is made, the cost for the recycling increases. Thus, using potassium terephthalate with low purity containing ethylene glycol as a raw material, it is desired to convert into useful chemicals using microorganisms. However, there are no reports on production of chemicals using microorganisms in a condition where terephthalate and ethylene glycol are present together. It is to be noted that *Escherichia coli* (hereinafter, as appropriate referred to as *Escherichia coli*) K-12 strain which is often used in the field of basic research and the field of industrial production is known to be capable of converting ethylene glycol into glycolic acid by lactaldehyde reductase and lactaldehyde dehydrogenase thereof. Moreover, it has been reported that introduction of mutation into lactaldehyde reductase improves the ability to metabolize ethylene glycol (Non-patent Documents 2 to 4).

PRIOR ART REFERENCES

Patent Documents

Patent Document 1: U.S. Pat. No. 5,068,414
Patent Document 2: U.S. Pat. No. 5,124,479
Patent Document 3: Japanese Patent Application Laid-Open Publication No. 2007-104942
Patent Document 4: Japanese Patent Application Laid-Open Publication No. 2009-65839
Patent Document 5: Japanese Patent Application Laid-Open Publication No. 2009-213392
Patent Document 6: U.S. Pat. No. 3,715,812
Patent Document 7: Japanese Patent Application Laid-Open Publication No. 2000-169623
Patent Document 8: U.S. Pat. No. 3,544,622

Patent Document 9: Japanese Patent Application Laid-Open Publication No. 2002-60542
Patent Document 10: Japanese Patent Application Laid-Open Publication No. 11-21374
Patent Document 11: U.S. Pat. No. 4,542,239
Patent Document 12: WO2005/082826

Non-Patent Documents

Non-patent Document 1: Polym.-Plastics Tech. Eng., 43, 369 (2004)
Non-patent Document 2: J. Bacteriol., 153, 134 (1983)
Non-patent Document 3: J. Bacteriol., 171, 6097 (1989)
Non-patent Document 4: J. Biol. Chem., 273, 8308 (1998)

SUMMARY OF THE INVENTION

An object of the present invention is to provide a method of producing TPA-DHD with alkali metal terephthalates as raw materials and, a method of converting TPA-DHD into protocatechuic acid using microorganisms and improving the capacity in production of these compounds; and to further provide a method of obtaining such alkali metal terephthalates by depolymerization of waste polyesters.

In order to solve the above objects, in the process of carrying out studies on depolymerization of a terephthalic acid-based polyester PET in an alkaline solution to obtain terephthalic acid, the inventors of the present invention compared the capacity of recombinant *Escherichia coli* in production of protocatechuic acid and found that the capacity in production of protocatechuic acid was higher when a potassium terephthalate (dipotassium terephthalate, 1-potassium 4-ammonium salt or 1-potassium 4-sodium terephthalate) was used as a raw material than when disodium terephthalate was used, thereby paying attention to the use of potassium terephthalate.

When the water-solubility of terephthalic acid salt to be used as a raw material is low, a fluid volume fed from a raw material tank increases and thereby the amount of intended compound produced per culture tank decreases. Therefore, it is preferred to use a terephthalic acid salt with high water-solubility as a raw material. In view of this, the solubility of disodium terephthalate, 1-potassium 4-sodium terephthalate, and dipotassium terephthalate in water at 30° C. was investigated; and what were found were the solubility of dipotassium terephthalate was about 1.0 M; the solubility of 1-potassium 4-sodium terephthalate was about 0.96 M; the solubility of disodium terephthalate was about 0.63 M; and potassium terephthalate had high water-solubility. Further, they also found was that potassium terephthalate such as dipotassium terephthalate or 1-potassium 4-sodium terephthalate provided the capacity of a microorganism such as *Escherichia coli* in production of an intended compound, as compared with disodium terephthalate.

Further, in light of the fact that the price per mole of ammonia is lower than the price per mole of potassium hydroxide or sodium hydroxide, the solubility of various ammonium terephthalates in water at 30° C. was investigated; and what were found were the solubility of 1-potassium 4-ammonium terephthalate was about 0.85 M; the solubility of 1-sodium 4-ammonium terephthalate was about 0.61 M; the solubility of diammonium terephthalate was about 0.51 M; and 1-potassium 4-ammonium terephthalate had high water-solubility. In addition, they also found that a capacity of a microorganism such as *Escherichia coli* in production of an intended compound was excellent when 1-potassium 4-ammonium terephthalate was used, thereby solving the object of the present invention.

Next, the inventors of the present invention intensively studied on depolymerization of each of PET, PTT and PBT in an alkaline solution by heating to find out that, when the depolymerization is carried out in an ethylene glycol reaction solvent containing an alkali metal hydroxide, the use of potassium hydroxide as the alkali metal hydroxide led to a faster depolymerization rate of the polyester and moreover better efficiency of collecting the terephthalic acid salt, as compared with the use of sodium hydroxide. As a result, they found that the depolymerization of terephthalic acid-based polyesters in the ethylene glycol reaction solvent containing potassium hydroxide is excellent as a method of preparing the terephthalic acid salt by the depolymerization of waste polyesters.

Further, the inventors of the present invention found that, alteration of the reaction solvent for the depolymerization from ethylene glycol to 1-butanol was able to lower a reaction temperature of the depolymerization and unexpectedly resulted in an excellent efficiency of collecting the terephthalic acid salt. Furthermore, in a depolymerization reaction in 1-butanol, the use of not sodium hydroxide but potassium hydroxide as an alkali metal hydroxide unexpectedly resulted in an excellent efficiency of depolymerizing the terephthalic acid salt.

As described above, the inventors of the present invention found that the use of not sodium but potassium as a used alkali metal was preferred not only in the production of an intended compound by microorganisms with an alkali metal salt of terephthalic acid as a raw material but also in the depolymerization reaction of polyesters in an ethylene glycol solvent or 1-butanol solvent for the purpose of obtaining potassium terephthalate for the raw material.

Accordingly, the present invention provides the following (1) to (24).

(1) A method of producing terephthalate 1,2-cis-dihydrodiol comprising reacting a microorganism or a processed product of a culture thereof with terephthalic acid in an aqueous medium containing a terephthalic acid salt to generate terephthalate 1,2-cis-dihydrodiol, wherein said terephthalic acid salt contains 0.5 times or more and twice or less the amount of potassium based on all of the terephthalic acids contained in the terephthalic acid salt in terms of moles: and wherein said microorganism has a DNA shown in the following (a), (b), (c), or (d); a DNA shown in the following (e), (f), (g); or (h), and a DNA shown in the following (i), (j), (k), or (l); and has an ability to produce terephthalate 1,2-cis-dihydrodiol from terephthalic acid;

(a) a DNA coding for a protein comprising the amino acid sequence set forth in SEQ ID NO: 2;

(b) a DNA comprising the amino acid sequence set forth in SEQ ID NO: 2 except that one or several amino acids are deleted, substituted, and/or added; and coding for a protein having a function involved in conversion from terephthalic acid to terephthalate 1,2-cis-dihydrodiol;

(c) a DNA comprising the nucleotide sequence set forth in SEQ ID NO: 1;

(d) a DNA that is able to hybridize with a DNA comprising a sequence complementary to the entire or a partial sequence of the nucleotide sequence set forth in SEQ ID NO: 1 under stringent conditions; and coding for a protein having a function involved in conversion from terephthalic acid to terephthalate 1,2-cis-dihydrodiol;

(e) a DNA coding for a protein comprising the amino acid sequence set forth in SEQ ID NO: 4;

(f) a DNA comprising the same amino acid sequence set forth in SEQ ID NO: 4 except that one or several amino acids are deleted, substituted, and/or added; and coding for a protein having a function involved in conversion from terephthalic acid to terephthalate 1,2-cis-dihydrodiol;

(g) a DNA comprising the nucleotide sequence set forth in SEQ ID NO: 3;

(h) a DNA that is able to hybridize with a DNA comprising a sequence complementary to the entire or a partial sequence of the nucleotide sequence set forth in SEQ ID NO: 3 under stringent conditions; and coding for a protein having a function involved in conversion from terephthalic acid to terephthalate 1,2-cis-dihydrodiol;

(i) a DNA coding for a protein comprising the amino acid sequence set forth in SEQ ID NO: 6;

(j) a DNA comprising the same amino acid sequence set forth in SEQ ID NO: 6 except that one or several amino acids are deleted, substituted, and/or added; and coding for a protein having a function involved in conversion from terephthalic acid to terephthalate 1,2-cis-dihydrodiol;

(k) a DNA comprising the nucleotide sequence set forth in SEQ ID NO: 5;

(l) a DNA that is able to hybridize with a DNA comprising a sequence complementary to the entire or a partial sequence of the nucleotide sequence set forth in SEQ ID NO: 5 under stringent conditions; and coding for a protein having a function involved in conversion from terephthalic acid to terephthalate 1,2-cis-dihydrodiol.

(2) The method of producing terephthalate 1,2-cis-dihydrodiol according to (1), wherein said aqueous medium containing a terephthalic acid salt is an aqueous solution containing one or more potassium terephthalates selected from the group consisting of dipotassium terephthalate, 1-potassium 4-sodium terephthalate, and 1-potassium 4-ammonium terephthalate.

(3) The method of producing terephthalate 1,2-cis-dihydrodiol according to (1) or (2), wherein said terephthalic acid salt is added as a form of aqueous solution, a form of powder or a form of suspension, to said microorganism or the processed product of a culture thereof to react said microorganism or the processed product with the terephthalic acid.

(4) The method of producing terephthalate 1,2-cis-dihydrodiol according to any one of (1) to (3), wherein the microorganism recited in (1) further has an enhanced ability to intracellularly transport terephthalic acid by introducing DNA shown in the following (m), (n), (o), or (p):

(m) a DNA coding for a protein comprising the amino acid sequence set forth in SEQ ID NO: 8;

(j) a DNA comprising the same amino acid sequence set forth in SEQ ID NO: 8 except that one or several amino acids are deleted, substituted, and/or added; and coding for a protein having a terephthalic acid transporter activity;

(o) a DNA comprising the nucleotide sequence set forth in SEQ ID NO: 7;

(p) a DNA that is able to hybridize with a DNA comprising a sequence complementary to the entire or a partial sequence of the nucleotide sequence set forth in SEQ ID) NO: 7 under stringent conditions; and coding for a protein having a terephthalic acid transporter activity.

(5) A method of producing protocatechuic acid comprising generating terephthalate 1,2-cis-dihydrodiol from terephthalic acid salt by the method according to any one of (1) to (4) and further converting terephthalate 1,2-cis-dihydrodiol into protocatechuic acid, wherein said microorganism further has a DNA shown in the following (q), (r), (s), or (t) and has an ability to produce protocatechuic acid from terephthalic acid:

(q) a DNA coding for a protein comprising the amino acid sequence set forth in SEQ ID NO: 10;

(r) a DNA comprising the same amino acid sequence set forth in SEQ ID NO: 10 except that one or several amino acids are deleted, substituted, and/or added; and coding for a protein having an activity of converting terephthalate 1,2-cis-dihydrodiol into protocatechuic acid;

(s) a DNA comprising the nucleotide sequence set forth in SEQ ID NO: 9;

(t) a DNA that is able to hybridize with a DNA comprising a sequence complementary to the entire or a partial sequence of the nucleotide sequence set forth in SEQ ID NO: 9 under stringent conditions; and coding for a protein having an activity of converting terephthalate 1,2-cis-dihydrodiol into protocatechuic acid.

(6) A method of producing protocatechuic acid comprising generating terephthalate 1,2-cis-dihydrodiol from terephthalic acid salt by the method according to any one of (1) to (4), and then converting terephthalate 1,2-cis-dihydrodiol into protocatechuic acid by using a microorganism obtained by introducing said DNA shown in (q), (r), (s), or (t) by transformation, or a processed product of a culture thereof.

(7) A method of producing gallic acid comprising generating terephthalate 1,2-cis-dihydrodiol from terephthalic acid salt by the method according to any one of (1) to (4) and then converting terephthalate 1,2-cis-dihydrodiol into gallic acid, wherein said microorganism further has a DNA shown in the following (q), (r), (s), or (t), a DNA shown in the following (u), (v), (w), or (x) and has an ability to produce gallic acid from terephthalic acid:

(q) a DNA coding for a protein comprising the amino acid sequence set forth in SEQ ID NO: 10;

(r) a DNA comprising the same amino acid sequence set forth in SEQ ID NO: 10 except that one or several amino acids are deleted, substituted, and/or added; and coding for a protein having an activity of converting terephthalate 1,2-cis-dihydrodiol into protocatechuic acid;

(s) a DNA comprising the nucleotide sequence set forth in SEQ ID NO: 9;

(t) a DNA that is able to hybridize with a DNA comprising a sequence complementary to the entire or a partial sequence of the nucleotide sequence set forth in SEQ ID NO: 9 under stringent conditions; and coding for a protein having an activity of converting terephthalate 1,2-cis-dihydrodiol into protocatechuic acid;

(u) a DNA coding for a protein comprising the amino acid sequence set forth in SEQ ID NO: 12;

(v) a DNA comprising the same amino acid sequence set forth in SEQ ID NO: 12 except that one or several amino acids are deleted, substituted, and/or added; and coding for a protein having an activity of converting protocatechuic acid into gallic acid;

(w) a DNA comprising the nucleotide sequence set forth in SEQ ID NO: 11;

(x) a DNA that is able to hybridize with a DNA comprising a sequence complementary to the entire or a partial sequence of the nucleotide sequence set forth in SEQ ID NO: 11 under stringent conditions; and coding for a protein having an activity of converting protocatechuic acid into gallic acid.

(8) A method of producing gallic acid comprising generating terephthalate 1,2-cis-dihydrodiol from terephthalic acid salt by the method according to any one of (1) to (4), and then converting terephthalate 1,2-cis-dihydrodiol into gallic acid by using a microorganism obtained by introducing the DNA shown in (u), (v), (w), or (x), in addition to the DNA shown in (q), (r), (s), or (t) by transformation, or a processed product of a culture thereof.

(9) The method of producing terephthalate 1,2-cis-dihydrodiol according to any one of (1) to (4) further comprising a step of obtaining terephthalic acid salt by the following steps (A) to (D):

(A) the step of heating a polyester waste material containing polyethylene terephthalate, polytrimethylene terephthalate, or polybutylene terephthalate as a major component and containing a foreign substance in an ethylene glycol reaction solvent containing potassium hydroxide or in an ethylene glycol reaction solvent containing both potassium hydroxide and sodium hydroxide at between 100° C. and 196° C. for 10 minutes or more to thereby evaporate water in a reaction solution and to concurrently depolymerize the polyethylene terephthalate, polytrimethylene terephthalate, or polybutylene terephthalate contained in the waste material;

(B) the step of removing a solid foreign substance floating in the depolymerization reaction solution of the waste material obtained in the step (A) by a flotation screening method out of solid foreign substances contained in the solution;

(C) the step of collecting solids other than the floating foreign substance from the solution subjected to the treatment of the step (B) by a solid-liquid separation method;

(D) the step of subjecting the solids collected by the step (C) to heat drying treatment, drying treatment under reduced pressure, or centrifugation treatment to thereby decrease a content of glycol in the solids and obtain a remaining solid as a terephthalic acid salt.

(10) The method of producing terephthalate 1,2-cis-dihydrodiol according to (9) comprising collecting the ethylene glycol reaction solvent after collecting the solids by the solid-liquid separation method in said step (C), and using the solvent as the ethylene glycol reaction solvent in said (A).

(11) The method of producing protocatechuic acid according to (5) or (6) further comprising the step of obtaining terephthalic acid salt by the following steps (A) to (D):

(A) the step of heating a polyester waste material containing polyethylene terephthalate, polytrimethylene terephthalate, or polybutylene terephthalate as a major component and containing a foreign substance in an ethylene glycol reaction solvent containing potassium hydroxide or in an ethylene glycol reaction solvent containing both potassium hydroxide and sodium hydroxide at between 100° C. and 196° C. for 10 minutes or more to thereby evaporate water in a reaction solution and to concurrently depolymerize the polyethylene terephthalate, polytrimethylene terephthalate, or polybutylene terephthalate contained in the waste material;

(B) the step of removing a solid foreign substance floating in the depolymerization reaction solution of the waste material obtained in the step (A) by a flotation screening method out of solid foreign substances contained in the solution;

(C) the step of collecting solids other than the floating foreign substance from the solution subjected to the treatment of the step (B) by a solid-liquid separation method;

(D) the step of subjecting the solids collected by the step (C) to heat drying treatment, drying treatment under reduced pressure, or centrifugation treatment to thereby decrease a content of glycol in the solids and obtain a remaining solid as a terephthalic acid salt.

(12) The method of producing protocatechuic acid according to (11) comprising collecting the ethylene glycol reaction solvent after collecting the solids by the solid-liquid separation method in said step (C); using the solvent as the ethylene glycol reaction solvent in said step (A); and thereby using terephthalic acid salt obtained by repeatedly use, without disposing of, the ethylene glycol reaction solvent.

(13) The method of producing gallic acid according to (7) or (8) further comprising the step of obtaining terephthalic acid salt by the following steps (A) to (D):

(A) the step of heating a polyester waste material containing polyethylene terephthalate, polytrimethylene terephthalate, or polybutylene terephthalate as a major component and containing a foreign substance in an ethylene glycol reaction solvent containing potassium hydroxide or in an ethylene glycol reaction solvent containing both potassium hydroxide and sodium hydroxide at between 100° C. and 196° C. for 10 minutes or more to thereby evaporate water in a reaction solution and to concurrently depolymerize the polyethylene terephthalate, polytrimethylene terephthalate, or polybutylene terephthalate contained in the waste material;

(B) the step of removing a solid foreign substance floating in the depolymerization reaction solution of the waste material obtained in the step (A) by a flotation screening method out of solid foreign substances contained in the solution;

(C) the step of collecting solids other than the floating foreign substance from the solution subjected to the treatment of the step (B) by a solid-liquid separation method;

(D) the step of subjecting the solids collected by the step (C) to heat drying treatment, drying treatment under reduced pressure, or centrifugation treatment to thereby decrease a content of glycol in the solids and obtain a remaining solid as a terephthalic acid salt.

(14) The method of producing gallic acid according to (13) comprising collecting the ethylene glycol reaction solvent after collecting the solids by the solid-liquid separation method in said step (C); using the solvent as the ethylene glycol reaction solvent in said step (A); and thereby using terephthalic acid salt obtained by repeatedly use, without disposing of, the ethylene glycol reaction solvent.

(15) The method of producing terephthalate 1,2-cis-dihydrodiol according to (9) or (10), wherein said microorganism according to (1) or (4) is able to decompose ethylene glycol contained in terephthalic acid salt obtained by said steps (A) to (D) by enhancing an expression amount of lactaldehyde reductase and lactaldehyde dehydrogenase.

(16) The method of producing protocatechuic acid according to (11) or (12), wherein said microorganism according to (5) is able to decompose ethylene glycol contained in terephthalic acid salt obtained by said steps (A) to (D) by enhancing an expression amount of lactaldehyde reductase and lactaldehyde dehydrogenase.

(17) The method of producing gallic acid according to (13) or (14), wherein said microorganism according to (7) is able to decompose ethylene glycol contained in terephthalic acid salt obtained by said steps (A) to (D) by enhancing an expression amount of lactaldehyde reductase and lactaldehyde dehydrogenase.

(18) The method of producing terephthalate 1,2-cis-dihydrodiol according to any one of (1) to (4) further comprising the step of obtaining terephthalic acid salt by the following steps (E) to (H):

(E) the step of heating a polyester waste material containing polyethylene terephthalate, polytrimethylene terephthalate, or polybutylene terephthalate as a major component and containing a foreign substance in a 1-butanol reaction solvent containing potassium hydroxide or in a 1-butanol reaction solvent containing both potassium hydroxide and sodium hydroxide at between 100° C. and 116° C. for 10 minutes or more to thereby evaporate water in a reaction solution and to concurrently depolymerize the polytrimethylene terephthalate or polybutylene terephthalate contained in the waste material;

(F) the step of removing a solid foreign substance floating in the depolymerization reaction solution of the waste material obtained in the step (E) by a flotation screening method out of solid foreign substances contained in the solution;

(G) the step of collecting solids other than the floating foreign substance from the solution subjected to the treatment of the step (F) by a solid-liquid separation method;

(H) the step of subjecting the solids collected by the step (G) to heat drying treatment, drying treatment under reduced pressure, or centrifugation treatment to thereby decrease a content of 1-butanol and glycols in the solids and obtain a remaining solid as a terephthalic acid salt.

(19) The method of producing terephthalate 1,2-cis-dihydrodiol according to (18) comprising collecting the 1-butanol reaction solvent after collecting the solids by the solid-liquid separation method in said step (G); using the solvent as the 1-butanol reaction solvent in said step (E); and thereby using terephthalic acid salt obtained by repeatedly using, without disposing of, ethylene glycol reaction solvent.

(20) The method of producing protocatechuic acid according to (5) or (6) further comprising the step of obtaining terephthalic acid salt by the following steps (E) to (H):

(E) the step of heating a polyester waste material containing polyethylene terephthalate, polytrimethylene terephthalate, or polybutylene terephthalate as a major component and containing a foreign substance in a 1-butanol reaction solvent containing potassium hydroxide or in a 1-butanol reaction solvent containing both potassium hydroxide and sodium hydroxide at between 100° C. and 116° C. for 10 minutes or more to thereby evaporate water in a reaction solution and to concurrently depolymerize the polytrimethylene terephthalate or polybutylene terephthalate contained in the waste material;

(F) the step of removing a solid foreign substance floating in the depolymerization reaction solution of the waste material obtained in the step (E) by a flotation screening method out of solid foreign substances contained in the solution;

(G) the step of collecting solids other than the floating foreign substance from the solution subjected to the treatment of the step (F) by a solid-liquid separation method;

(H) the step of subjecting the solids collected by the step (G) to heat drying treatment, drying treatment under reduced pressure, or centrifugation treatment to thereby decrease a content of 1-butanol and glycols in the solids and obtain a remaining solid as a terephthalic acid salt.

(21) The method of producing protocatechuic acid according to (20) comprising collecting the 1-butanol reaction solvent after collecting the solids by the solid-liquid separation method in said step (G); using the solvent as the 1-butanol reaction solvent in said step (E); and thereby using terephthalic acid salt obtained by repeatedly using, without disposing of, the ethylene glycol reaction solvent.

(22) The method of producing gallic acid according to (7) or (8) further comprising the step of obtaining terephthalic acid salt by the following steps (E) to (H):

(E) the step of heating a polyester waste material containing polyethylene terephthalate, polytrimethylene terephthalate, or polybutylene terephthalate as a major component and containing a foreign substance in a 1-butanol reaction solvent containing potassium hydroxide or in a 1-butanol reaction solvent containing both potassium hydroxide and sodium hydroxide at between 100° C. and 116° C. for 10 minutes or more to thereby evaporate water in a reaction solution and to concurrently depolymerize the polytrimethylene terephthalate or polybutylene terephthalate contained in the waste material;

(F) the step of removing a solid foreign substance floating in the depolymerization reaction solution of the waste material obtained in the step (E) by a flotation screening method out of solid foreign substances contained in the solution;

(G) the step of collecting solids other than the floating foreign substance from the solution subjected to the treatment of the step (F) by a solid-liquid separation method;

(H) the step of subjecting the solids collected by the step (G) to heat drying treatment, drying treatment under reduced pressure, or centrifugation treatment to thereby decrease a content of I-butanol and glycols in the solids and obtain a remaining solid as a terephthalic acid salt.

(23) The method of producing gallic acid according to (22) comprising collecting the 1-butanol reaction solvent after collecting the solids by the solid-liquid separation method in said step (G); using the solvent as the 1-butanol reaction solvent in said step (E); and thereby using terephthalic acid salt obtained by repeatedly using, without disposing of, the ethylene glycol reaction solvent.

(24) The method of production according to any one of (1) to (23) wherein said microorganism is *Escherichia coli*.

According to the present invention, when a terephthalic acid salt contains 0.5 times or more and twice or less the amount of potassium based on all of the terephthalic acids contained in the terephthalic acid salt in terms of moles is used as a raw material, TPA-DHD can be efficiently produced using a microorganism. In addition, according to the present invention, the obtained TPA-DHD can be efficiently converted into protocatechuic acid or gallic acid. Further, by depolymerization of waste polyesters, potassium terephthalate suitable for the raw material of terephthalate derivatives by the microorganism can be efficiently prepared.

EMBODIMENTS FOR CARRYING OUT THE INVENTION

Figure 1:
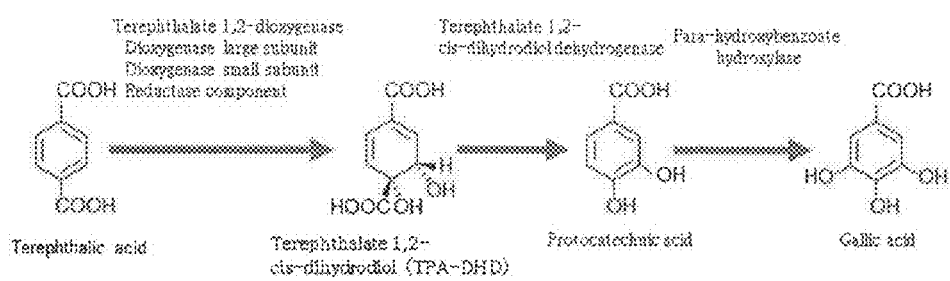
FIG. 1 shows the pathway in which protocatechuic acid and gallic acid are produced from terephthalic acid via TPA-DHD.

The present invention will be described in detail below.

As a mode of terephthalic acid used as a raw material of compound production by a microorganism, terephthalic acid salts are in general more preferred than terephthalic acid itself because they have higher water-solubility. Examples of the terephthalic acid salts to be used for such a purpose include dipotassium terephthalate, 1-potassium 4-sodium terephthalate, 1-potassium 4-ammonium terephthalate, disodium terephthalate, 1-sodium 4-ammonium terephthalate, and diammonium terephthalate.

Here, dipotassium terephthalate refers to a salt in which the carboxyl group residues at positions 1 and 4 of terephthalic acid are ionically bound with potassium ions.

1-potassium 4-sodium terephthalate refers to a salt in which the carboxyl group residue at position 1 of terephthalic acid is ionically bound with a potassium ion and the carboxyl group residue at position 4 of terephthalic acid is ionically bound with a sodium ion.

1-potassium 4-ammonium terephthalate refers to a salt in which the carboxyl group residue at position 1 of terephthalic acid is ionically bound with a potassium ion and the carboxyl group residue at position 4 of terephthalic acid is ionically bound with an ammonium ion.

Disodium terephthalate refers to a salt in which the carboxyl group residues at positions 1 and 4 of terephthalic acid are ionically bound with sodium ions.

1-sodium 4-ammonium terephthalate refers to a salt in which the carboxyl group residue at position 1 of terephthalic acid is ionically bound with a sodium ion and the carboxyl group residue at position 4 of terephthalic acid is ionically bound with an ammonium ion.

Diammonium terephthalate refers to a salt in which the carboxyl group residues at positions 1 and 4 of terephthalic acid are ionically bound with ammonium ions.

An aqueous solution of each of the terephthalalic acid salts, namely dipotassium terephthalate, 1-potassium 4-sodium terephthalate, 1-potassium 4-ammonium terephthalate, disodium terephthalate, 1-sodium 4-ammonium terephthalate, and diammonium terephthalate, can be obtained by adding, based on terephthalic acid powder, twice the amount of potassium hydroxide in terms of molar ratio, one-fold the amount of potassium hydroxide and one-fold the amount of sodium hydroxide in terms of molar ratio, one-fold the amount of potassium hydroxide and an ammonium solution containing one-fold the amount of ammonia in terms of molar ratio, twice the amount of sodium hydroxide in terms of molar ratio, one-fold the amount of sodium hydroxide and an ammonium solution containing one-fold the amount of ammonia in terms of molar ratio, and an ammonium solution containing twice the amount of ammonia in terms of molar ratio, respectively, to an appropriate amount of water; and then stirring while heating. Powder of terephthalalic acid salt can be obtained by applying heat drying treatment, drying treatment under reduced pressure, or crystallization treatment to an aqueous solution of the terephthalalic acid salt.

The terephthalalic acid salt to be used in the present invention refers to a terephthalalic acid salt that contains 0.5 times or more and twice or less the amount of potassium based on all of the terephthalic acids contained in the terephthalalic acid salt in terms of moles. More preferably, it is a terephthalalic acid salt that contains 0.6 times or more and twice or less the amount of potassium based on all of the terephthalic acids contained in the terephthalalic acid salt in terms of moles.

Here, the amount of potassium defined to be contained in a 0.5 times or more and twice or less amount based on all of the terephthalic acids contained in the terephthalalic acid salt in terms of moles refers to the amount of potassium derived from potassium terephthalate, that is, potassium forming an ionic bond with the carboxyl group residues of the terephthalic acid. That is, in cases where a crude terephthalalic acid salt is used, even if potassium derived from potassium hydroxide or the like is contained therein as an impure substance, the amount of potassium is calculated by excluding such potassium. At the time of reaction, potassium (ion) derived from the potassium terephthalate needs only to be contained in a 0.5 times or more and twice or less amount based on all of the terephthalic acids in terms of moles in an aqueous solvent.

As for the terephthalalic acid salt, any mode of a powder of the terephthalalic acid salt, an aqueous solution in which the terephthalalic acid salt is dissolved, or a suspension of the terephthalalic acid salt in which the powder of the terephthalalic acid salt is mixed and present in the aqueous solution of the terephthalalic acid salt in a slurry state can be used in the present invention. Hereinafter, the terephthalalic acid salt, unless otherwise specified, shall include any mode of the terephthalalic acid salt.

Preferably, in the present invention, a terephthalalic acid salt that contains one or more potassium terephthalates selected from the group consisting of dipotassium terephthalate, 1-potassium 4-sodium terephthalate, and 1-potassium 4-ammonium terephthalate; and contains 0.5 times or more and twice or less the amount of potassium based on all of the terephthalic acids contained in the terephthalalic acid salt in terms of moles can be used.

In the present invention, a terephthalalic acid salt selected from dipotassium terephthalate, 1-potassium 4-sodium terephthalate, and 1-potassium 4-ammonium terephthalate as a single component may be used. On the other hand, the terephthalalic acid salt to be used in the present invention may contain, in addition to the above potassium terephthalate, disodium terephthalate, 1-sodium 4-ammonium terephthalate, diammonium terephthalate and the like as long as it satisfies with the above potassium content.

For instance, in cases where a mixture of two kinds of terephthalalic acid salts, 1-potassium 4-sodium terephthalate and disodium terephthalate, whereby 1-potassium 4-sodium terephthalate is contained one or more times the amount based on disodium terephthalate in terms of molar ratio, can be used. Further, in cases where a mixture of two kinds of terephthalates, dipotassium terephthalate and disodium terephthalate, whereby dipotassium terephthalate is contained ⅓ times or more the amount based on disodium terephthalate in terms of molar ratio can be used.

In the present invention, a mixture of 3 kinds or more of terephthalalic acid salts can also be used. In this instance, such a mixture needs to contain 0.5 times or more and twice or less the amount of potassium based on all of the terephthalic acids contained in the terephthalalic acid salt in terms of moles. Preferably, a terephthalalic acid salt containing one or more kinds of potassium terephthalates selected from the group consisting of dipotassium terephthalate, 1-potassium 4-sodium terephthalate, and 1-potassium 4-ammonium terephthalate; and 2 or more kinds of terephthalalic acid salts selected from the group consisting of disodium terephthalate, 1-sodium 4-ammonium terephthalate and diammonium terephthalate can be used. Concrete examples thereof include an aqueous solution prepared by mixing dipotassium terephthalate, disodium terephthalate, and diammonium terephthalate at a ratio of 1:2:1 in terms of molar ratio. Such an aqueous solution contains 0.5 times the amount of potassium based on all of the terephthalic acids, and can also be obtained by adding, based on 1 mole of terephthalic acid, 0.5 moles of potassium hydroxide, 1.0 mole of sodium hydroxide, and 0.5 moles of ammonia in water to dissolve.

In the present invention, a terephthalalic acid salt containing dipotassium terephthalate or 1-potassium 4-sodium terephthalate obtained by depolymerizing waste polyesters in an ethylene glycol solvent or 1-butanol solvent containing potassium hydroxide or a mixture of potassium hydroxide and sodium hydroxide can be used as a raw material of compound production by a microorganism.

In this instance, because the price per mole of sodium hydroxide or ammonium solution is lower than that of potassium hydroxide, the production cost may in some cases be lower when a terephthalalic acid salt generated by adding terephthalic acid with high purity and sodium hydroxide or ammonium solution to the terephthalalic acid salt obtained by the depolymerization of waste polyesters is used. Concrete examples thereof include use of an aqueous solution of the terephthalalic acid salt obtained by mixing dipotassium terephthalate obtained by the depolymerization of waste polyesters, terephthalic acid with high purity, and ammonium solution at a ratio of 6:4:8, respectively. The thus obtained aqueous solution of terephthalalic acid salt is equivalent to an aqueous solution obtained by mixing dipotassium terephthalate and diammonium terephthalate at a ratio of 6:4 in terms of molar ratio.

In cases where potassium terephthalate is prepared from waste polyesters using the method disclosed in the present invention, besides potassium ions, sodium ions, and ammonium ions, other metal ions such as calcium ions or lithium ions may be contaminated as foreign substances. In this instance, as long as the terephthalalic acid salt to be used in the present invention is a terephthalalic acid salt containing 0.5 times or more and twice or less the amount of potassium based on all of the terephthalic acids contained in the terephthalalic acid salt in terms of moles, there would be no problems even if a small amount of terephthalalic acid salt such as calcium terephthalate or lithium terephthalate mixed is contaminated.

The steps of producing TPA-DHD, protocatechuic acid, and gallic acid from terephthalic acid in the present invention will now be described. As shown in FIG. 1, terephthalic acid is oxidized by terephthalate 1,2-dioxygenase to be converted into TPA-DHD. Further, TPA-DI-HD can be converted into protocatechuic acid by TPA-DHD dehydrogenase. Furthermore, protocatechuic acid can be converted into gallic acid by para-hydroxybenzoate hydroxylase or improved para-hydroxybenzoate hydroxylase (for example, a mutant having the same amino acid sequence as para-hydroxybenzoate hydroxylase except that leucine at position 199 or leucine at position 200 is substituted by valine or glycine; and tyrosine at position 385 or 386 is substituted phenyl alanine, valine, or alanine).

The terephthalate 1,2-dioxygenase to be used in the present invention is composed of an oxygenase component and a reductase component. Further, the oxygenase component is composed of two subunits: large and small ones. Examples of the oxygenase large subunit protein include a protein having the amino acid sequence set forth in SEQ ID NO: 2, which amino acid sequence is derived from *Comamonas testeroni* 72W2 strain. The bacterial strain has been internationally deposited with Incorporated Administrative Agency National Institute of Technology and Evaluation, Patent Microorganisms Depositary (NPMD) (2-5-8, Kazusakamatari, Kisarazu-shi, Chiba 292-0818, Japan) under Accession No. NITE ABP-1209 as of Jan. 24, 2012 and available for furnishing. Further, examples of the oxygenase large subunit protein to be used in the present invention include a protein having the amino acid sequence set forth in SEQ ID NO: 2 except that one or several amino acids are deleted, substituted, or added, and having a function involved in conversion from terephthalic acid into TPA-DHD. In addition, examples of such a protein include a protein composed of an amino acid sequence with an identity of 75% or more, preferably 90% or more, in particular preferably 95% or more to the amino acid sequence of SEQ ID NO: 2, and having a function involved in conversion from terephthalic acid into TPA-DHD. Here, a "function involved in conversion from terephthalic acid into TPA-DHD" means a function whereby TPA-DHD may be generated when terephthalic acid is allowed to react in conjunction with a terephthalate 1,2-dioxygenase oxygenase small subunit protein and terephthalate 1,2-dioxygenase reductase protein.

Examples of the terephthalate 1,2-dioxygenase oxygenase small subunit protein include a protein having the amino acid sequence set forth in SEQ ID NO: 4, which amino acid sequence is derived from the above-mentioned *Comamonas testeroni* 72W2 strain. Further, examples of the terephthalate 1,2-dioxygenase oxygenase small subunit protein to be used in the present invention include a protein having the amino acid sequence set forth in SEQ ID NO: 4 except that one or several amino acids are deleted, substituted, or added, and a function involved in conversion from terephthalic acid into TPA-DHD. In addition, examples of such a protein include a protein composed of an amino acid sequence with an identity of 75% or more, preferably 90% or more, in particular preferably 95% or more to the amino acid sequence of SEQ ID NO: 4, and having a function involved in conversion from terephthalic acid into TPA-DHD. Here, a "function involved in conversion from terephthalic acid into TPA-DHD" means a function whereby TPA-DHD may be generated when terephthalic acid is allowed to react in conjunction with a terephthalate 1,2-dioxygenase oxygenase large subunit protein and terephthalate 1,2-dioxygenase reductase protein.

Examples of the terephthalate 1,2-dioxygenase oxygenase small subunit protein to be used in the present invention include a protein having the amino acid sequence set forth in SEQ ID NO: 6, which amino acid sequence is derived from the above-mentioned *Comamonas testeroni* 72W2 strain. Further, examples of the terephthalate 1,2-dioxygenase reductase protein to be used in the present invention include a protein having the amino acid sequence set forth in SEQ ID NO: 6 except that one or several amino acids are deleted, substituted, or added, and a function involved in conversion from terephthalic acid into TPA-DHD. In addition, examples of such a protein include a protein composed of an amino acid sequence with an identity of 75% or more, preferably 90% or more, in particular preferably 95% or more to the amino acid sequence of SEQ ID NO: 6, and having a function involved in conversion from terephthalic acid into TPA-DHD. Here, a "function involved in conversion from terephthalic acid into TPA-DHD" means a function whereby TPA-DHD may be generated when terephthalic acid is allowed to react in conjunction with a terephthalate 1,2-dioxygenase oxygenase large subunit protein and terephthalate 1,2-dioxygenase oxygenase small subunit protein.

Examples of the terephthalic acid transporter protein to be used in the present invention include a protein having the amino acid sequence set forth in SEQ ID NO: 8, which amino acid sequence is derived from *Rhodococcus jostii* RHA1 strain. Further, examples of the terephthalic acid transporter protein to be used in the present invention include a protein having the amino acid sequence set forth in SEQ ID NO: 8 except that one or several amino acids are deleted, substituted, or added, and having an ability to intracellularly transport terephthalic acid. In addition, examples of such a protein include a protein composed of an amino acid sequence with an identity of 75% or more, preferably 90% or more, in particular preferably 95% or more to the amino acid sequence of SEQ ID NO: 8, and having an activity of transporting terephthalic acid into cells.

Examples of the TPA-DHD dehydrogenase protein to be used in the present invention include a protein having the amino acid sequence set forth in SEQ ID NO: 10, which amino acid sequence is derived from the above-mentioned *Comamonas testeroni* 72W2 strain. Further, examples of the TPA-DHD dehydrogenase protein to be used in the present invention include a protein having the amino acid sequence set forth in SEQ ID NO: 10 except that one or several amino acids are deleted, substituted, or added, and having an activity of converting TPA-DHD into protocatechuic acid. In addition, examples of such a protein include a protein composed of an amino acid sequence with an identity of 75% or more, preferably 90% or more, in particular preferably 95% or more to the amino acid sequence of SEQ ID NO: 10, and having an activity of converting TPA-DHD into protocatechuic acid.

Examples of the para-hydroxybenzoate hydroxylase to be used in the present invention include a protein of GenBank (hereinafter, GenBank is abbreviates as GB) GB Accession No. AAG03636 of *Pseudomonas aeruginosa* PAO strain, a protein of GB Accession No. AAN69138 of *Pseudomonas putida* KT2440 strain, and a protein having the amino acid sequence set forth in SEQ ID NO: 12, which amino acid sequence is derived from *Corynebacterium glutamicum* ATCC13032 strain. Further, examples of the para-hydroxybenzoate hydroxylase protein to be used in the present invention include a protein having the amino acid sequence set forth in SEQ ID NO: 12 except that one or several amino acids are deleted, substituted, or added, and an activity of converting protocatechuic acid into gallic acid. In particular, it is preferred to use a mutant having the amino acid sequence as GB Accession No. AAG03636 except that leucine at position 199 is substituted by valine or glycine and tyrosine at position 385 is substituted by phenyl alanine, valine, or alanine; a mutant having the amino acid sequence as GB Accession No. AAN69138 except that leucine at position 199 is substituted by valine or glycine and tyrosine at position 386 is substituted by phenyl alanine, valine, or alanine; or a mutant having the amino acid sequence as GB Accession No. BAB98470 except that leucine at position 200 is substituted by valine or glycine and tyrosine at position 385 is substituted by phenyl alanine, valine, or alanine. In addition, examples of such a protein include a protein composed of an amino acid sequence with an identity of 75% or more, preferably 90% or more, in particular preferably 95% or more to the amino acid sequence of SEQ ID NO: 12, and having an activity of converting protocatechuic acid into gallic acid.

Examples of the lactaldehyde reductase to be used in the present invention include a protein of GB Accession No. AAB40449 of *Escherichia coli* K-12 strain. Further, examples of the lactaldehyde reductase protein to be used in the present invention include a protein having the amino acid sequence of GB Accession No. AAB40449 except that one or several amino acids are deleted, substituted, or added, and having an activity of converting ethylene glycol into glycoaldehyde. In addition, examples of such a protein include a protein composed of an amino acid sequence with an identity of 75% or more, preferably 90% or more, in particular preferably 95% or more to the amino acid sequence of GB Accession No. AAB40449, and having an activity of converting ethylene glycol into glycoaldehyde.

Examples of the lactaldehyde dehydrogenase to be used in the present invention include a protein of GB Accession No. AAC74497 of *Escherichia coli* K-12 strain. Further, examples of the lactaldehyde dehydrogenase protein to be used in the present invention include a protein having the amino acid sequence of GB Accession No. AAC74497 except that one or several amino acids are deleted, substituted, or added, and having an activity of converting glycoaldehyde into glycolic acid. In addition, examples of such a protein include a protein composed of an amino acid sequence with an identity of 75% or more, preferably 90% or more, in particular preferably 95% or more to the amino acid sequence of GB Accession No. AAC74497, and having an activity of converting glycoaldehyde into glycolic acid.

These bacterial strains can be obtained from ATCC, Incorporated Administrative Agency National Institute of Technology and Evaluation, Biological Resource Center (hereinafter, abbreviated as NBRC), Incorporated Administrative Agency RIKEN Tsukuba Campus, Biological Resource Center, National Institute of Genetics, National BioResource Project (hereinafter, abbreviated as NBRP), The Coli Genetic Stock Center (hereinafter, abbreviated as CGSC as necessary), or the like.

A protein composed of the amino acid sequence as the above terephthalate 1,2-dioxygenase oxygenase large subunit protein, terephthalate 1,2-dioxygenase oxygenase small subunit protein, terephthalate 1,2-dioxygenase reductase protein, TPA-DHD dehydrogenase protein, terephthalic acid transporter protein, lactaldehyde reductase protein, or lactaldehyde dehydrogenase protein except that one or several amino acids are deleted, substituted, or added and having each of the activities of intended enzyme can be obtained by introducing site specific mutations into DNA such that deletion, substitution, or addition is introduced at specific positions in each of the proteins using a site specific mutagenesis method described in Molecular Cloning, A Laboratory Manual, Second Edition, Cold Spring Harbor Laboratory Press (1989) (hereinafter, shortened to Molecular Cloning Second Edition), Current Protocols in Molecular Biology, John Wiley & Sons (1987-1997) (hereinafter, shortened to Current Protocols in Molecular Biology), Nucleic Acids Res., 10, 6487 (1982), Proc. Natl. Acad. Sci., USA, 79, 6409 (1982), Gene, 34, 315 (1985), Nucleic Acids Res., 13, 4431 (1985), Proc. Natl. Acad. Sci., USA, 82, 488 (1985) or the like. The number of the amino acids in the phrase "one or several amino acids are deleted, substituted, or added" is not particularly restricted as long as each of the enzyme activities is maintained. It is desired to be within the number of amino acids different from the original amino acid sequence; and preferred to be 1 to 20, more preferably 1 to 10, and in particularly 1 to 5.

Examples of DNA coding for the terephthalate 1,2-dioxygenase oxygenase large subunit protein to be used in the present invention include DNA having the nucleotide sequence set forth in SEQ ID NO: 1.

Examples of DNA coding for the terephthalate 1,2-dioxygenase oxygenase small subunit protein to be used in the present invention include DNA having the nucleotide sequence set forth in SEQ ID NO: 3.

Examples of DNA coding for the terephthalate 1,2-dioxygenase reductase protein to be used in the present invention include DNA having the nucleotide sequence set forth in SEQ ID NO: 5.

Examples of DNA coding for the terephthalic acid transporter protein to be used in the present invention include DNA having the nucleotide sequence set forth in SEQ ID NO: 7.

Examples of DNA coding for the TPA-DHD dehydrogenase protein to be used in the present invention include DNA having the nucleotide sequence set forth in SEQ ID NO: 9.

Examples of DNA coding for the para-hydroxybenzoate hydroxylase protein to be used in the present invention include DNA having the nucleotide sequence set forth in SEQ ID NO: 11.

Examples of DNA coding for the lactaldehyde reductase protein to be used in the present invention include DNA having the nucleotide sequence of positions 13420 to 14571 of GB Accession No. U2958.

Examples of DNA coding for the lactaldehyde dehydrogenase protein to be used in the present invention include DNA having the nucleotide sequence of positions 1486256 to 1487695 of GB Accession No. NC_000913.

The DNA to be used in the present invention also encompasses DNA in which mutation such as substitution mutation, deletion mutation, or insertion mutation is introduced to the extent that a protein coded by each DNA does not lose an intended enzyme activity; and DNA that is able to hybridize with the entire or a part of DNA set forth in, for example, SEQ ID NO: 1, 3, 5, 7, 9 or 11 as a probe under stringent conditions by a hybridization method. To be specific, DNA that is able to hybridize under stringent conditions means DNA that can be identified by, using a filter immobilized with DNA, washing the filter at 65° C. in an SSC solution with a concentration of between 0.1-fold concentration to two-fold concentration (the composition of an SSC solution with 1-fold concentration was 150 mM NaCl and 15 mM sodium citrate) after carrying out hybridization in the presence of 0.7 to 1.0 M NaCl at 65° C. It is to be noted that experimental methods of hybridization are described in Molecular Cloning: A laboratory manual, Second Edition (edited by Sambrook, Fritsch, and Maniatis, Cold Spring Harbor Laboratory Press, published in 1989).

As a microorganism to be used in the present invention for producing TPA-DHD with a terephthalalic acid salt containing 0.5 times or more and twice or less the amount of potassium based on all of the terephthalic acids contained in the terephthalalic acid salt in terms of moles as a raw material, any microorganism can be used as long as it is a microorganism having DNA coding for the above terephthalate 1,2-dioxygenase oxygenase large subunit, DNA coding for the above terephthalate 1,2-dioxygenase oxygenase small subunit, and DNA coding for the above terephthalate 1,2-dioxygenase oxygenase reductase; and having an ability to produce TPA-DHD from terephthalic acid. That is, a microorganism having the DNA described in the above-mentioned (1) and having an ability to produce TPA-DHD from terephthalic acid can be used. A microorganism having such a property may be a transformant obtained by introducing one or more DNAs of the DNAs described in the above-mentioned (1) into host cells using a recombination technique.

Further, when TPA-DHD is produced with a terephthalalic acid salt as a raw material using the above microorganism, it is preferred to use, as such a microorganism, a microorganism that has DNA coding for terephthalic acid transporter and whose ability to transport terephthalic acid is enhanced. A microorganism having such a property may be a transformant obtained by introducing, in addition to one or more DNAs of the DNAs described in the above-mentioned (1), one or more DNAs of the DNAs described in the above-mentioned (4) into host cells using a recombination technique.

As a microorganism to be used in the present invention for production of protocatechuic acid, any microorganism can be used as long as it is a microorganism having DNA coding for a protein having a TPA-DHD dehydrogenase activity and having an ability to produce protocatechuic acid from TPA-DHD, in addition to the above-mentioned ability to produce TPA-DHD from terephthalic acid. That is, a microorganism described in the above-mentioned (1) or (4), the microorganism having the DNA described in the above-mentioned (5) and having an ability to produce protocatechuic acid from TPA-DHD can be used. A microorganism having such a property may be a transformant obtained by introducing, in addition to one or more DNAs of the DNAs described in the above-mentioned (1), one or more DNAs of the DNAs described in the above-mentioned (5) into host cells using a recombination technique. Further, when protocatechuic acid is produced with a terephthalalic acid salt as a raw material using the above microorganism, it is preferred to use, as such a microorganism, a microorganism that has DNA coding for terephthalic acid transporter and whose ability to transport terephthalic acid is enhanced. As a microorganism having such a property, a transformant obtained by introducing, in addition to the DNAs described in the above-mentioned (1) and (4), one or more DNAs of the DNAs described in the above-mentioned (5) into host cells using a recombination technique can be used.

As a microorganism to be used in the present invention for production of gallic acid, any microorganism can be used as long as it is a microorganism having DNA coding for a protein having a TPA-DHD dehydrogenase activity and DNA coding for a protein having para-hydroxybenzoate hydroxylase; and having an ability to produce gallic acid from TPA-DHD, in addition to the above-mentioned ability to produce TPA-DHD from terephthalic acid. That is, a microorganism having, in addition to the DNA described in the above-mentioned (5), the DNA described in the above-mentioned (7) and having an ability to produce gallic acid from terephthalic acid can be used. A microorganism having such a property may be a transformant obtained by introducing, in addition to one or more DNAs of the DNAs described in the above-mentioned (1) and (5), one or more DNAs of the DNAs described in the above-mentioned (7) into host cells using a recombination technique. Further, when gallic acid is produced with a terephthalate as a raw material using the above microorganism, it is preferred to use, as such a microorganism, a microorganism that has DNA coding for terephthalic acid transporter and whose ability to transport terephthalic acid is enhanced. The microorganism having such a property may be a transformant obtained by introducing, in addition to the DNAs described in the above-mentioned (1), (4), and (5), one or more DNAs of the DNAs described in the above-mentioned (7) into host cells using a recombination technique.

As a microorganism to be used in the present invention that decomposes ethylene glycol contaminated in terephthalalic acid salt when polyesters are depolymerized in an ethylene glycol solvent, what can be used is a microorganism whose ability to decompose ethylene glycol is enhanced by introducing mutation in lactaldehyde reductase and lactaldehyde dehydrogenase, and/or enhancing the expression amount of lactaldehyde reductase and lactaldehyde dehydrogenase in the above-mentioned microorganism that produces TPA-DHD, protocatechuic acid, or gallic acid from terephthalic acid.

DNA cloning and a method of creating a transformed strain will now be described in detail below.

Bacteria such as *Escherichia coli* K-12 strain which is described above, *Comamonas testeroni* 72W2 strain, *Rhodococcus jostii* RHA1 strain, or *Corynebacterium glutamicum* ATCC13032 strain is cultured under culture conditions recommended by the above microorganism depository institute or a known method that is usually used. After the culturing, the chromosomal DNA of such a microorganism is isolated and purified by a known method (for example, a method described in Current Protocols in Molecular Biology). A fragment containing DNA coding for an intended protein can be obtained from this chromosomal DNA using a synthetic DNA by a hybridization method, PCR method, or the like.

DNA coding for an intended protein can also be obtained by chemical synthesis. Such a synthetic DNA can be designed on the basis of, for example, the nucleotide sequence set forth in SEQ ID NO: 1 coding for the terephthalate 1,2-dioxygenase oxygenase large subunit protein derived from *Comamonas testeroni* 72W2 strain, the nucleotide sequence set forth in SEQ ID NO: 3 coding for the terephthalate 1,2-dioxygenase oxygenase small subunit protein derived from *Comamonas testeroni* 72W2 strain, and the nucleotide sequence set forth in SEQ ID NO: 5 coding for the terephthalate 1,2-dioxygenase reductase protein derived from *Comamonas testeroni* 72W2 strain.

A synthetic DNA coding for a terephthalic acid transporter protein can be designed on the basis of the nucleotide sequence set forth in SEQ ID NO: 7 of DNA coding for the terephthalic acid transporter protein derived from *Rhodococcus jostii* RHA1 strain.

A synthetic DNA coding for TPA-DHD dehydrogenase can be designed on the basis of the nucleotide sequence set forth in SEQ ID NO: 9 of DNA coding for the TPA-DHD dehydrogenase protein derived from *Comamonas testeroni* 72W2 strain.

A synthetic DNA coding for para-hydroxybenzoate hydroxylase can be designed on the basis of the nucleotide sequence set forth in SEQ ID NO: 11 of DNA coding for the para-hydroxybenzoate hydroxylase protein (a protein in which tyrosine at position 385 is substituted by phenyl alanine) derived from *Corynebacterium glutamicum* ATCC13032 strain.

A synthetic DNA coding for lactaldehyde reductase can be designed on the basis of the nucleotide sequence of positions 13420 to 14571 of GB Accession No. U2958 of DNA coding for the lactaldehyde reductase protein derived from *Escherichia coli* K-12 strain.

A synthetic DNA coding for lactaldehyde dehydrogenase can be designed on the basis of the nucleotide sequence of positions 1486256 to 1487695 of GB Accession No. NC_000913 of DNA coding for the lactaldehyde dehydrogenase protein derived from *Escherichia coli* K-12 strain.

As a vector to which the above DNA is linked, any vector including plasmid vector and phage vector can be used as long as it is a vector capable of autonomously replicating in *Escherichia coli* K12 strain or the like. To be specific, pUC19 (Gene, 33, 103 (1985)), pUC18, pBR322, pHelix1 (manufactured by Roche Diagnostics), ZAP Express (manufactured by Stratagene, Strategies, 5, 58 (1992)), pBluescript II SK(+) (manufactured by Stratagene, Nucleic Acids Res., 17, 9494 (1989)), pUC118 (manufactured by Takara Bio Inc.), or the like can be used.

As *Escherichia coli* to be used as a host for a recombinant DNA obtained by linking the DNA obtained above to such a vector, any microorganism can be used as long as it is a microorganism belonging to *Escherichia coli*. Concrete examples thereof include *Escherichia coli* XL1-Blue MRF' (manufactured by Stratagene, Strategies, 5, 81 (1992)), *Escherichia coli* C600 (Genetics, 39, 440 (1954)), *Escherichia coli* Y1088 (Science, 222, 778 (1983)), *Escherichia coli* Y1090 (Science, 222, 778 (1983)), *Escherichia coli* NM522 (J. Mol. Biol., 166, 1 (1983)), *Escherichia coli* K802 (J. Mol. Biol., 16, 118 (1966)), *Escherichia coli* JM105 (Gene, 38, 275 (1985)), and *Escherichia coli* JM109, *Escherichia coli* BL21.

When the above DNA is introduced into a microorganism belonging to the genus *Rhodococcus*, the genus *Comamonas*, the genus *Corynebacterium*, the genus *Pseudomonas*, the genus *Polaromonas*, the genus *Ralstonia*, or the genus *Burkholderia*, a vector capable of autonomously replicating in these microorganisms is used. Preferably, using a shuttle vector capable of autonomously replicating in both microorganisms of any of such microorganisms and *Escherichia coli* K12 strain, a recombinant DNA can be introduced into such a microorganism that serves as a host.

As a method of introducing a recombinant DNA, any method can be used as long as it is a method of introducing DNA into the above host cells, and examples thereof include a method using calcium ions (Proc. Natl. Acad. Sci., USA, 69, 2110 (1972)), an electroporation method (Nucleic Acids Res., 16, 6127 (1988)), a conjugation transfer method (J. G. C. Ottow, Ann. Rev. Microbiol., Vol. 29, p. 80 (1975)), and a cell fusion method (M. H. Gabor, J. Bacteriol., Vol. 137, p. 1346 (1979)).

A recombinant DNA is extracted from the transformant obtained as described above, and the nucleotide sequence of DNA used in the present invention that is contained in such a recombinant DNA can be determined. For the determination of the nucleotide sequence, a nucleotide sequence analysis method that is commonly used including, for example, the dideoxy chain termination method (Proc. Natl. Acad. Sci. USA, 74, 5463 (1977)); or a nucleotide sequence analytical apparatus 3730xl type DNA analyzer (manufactured by Applied Biosystems) can be used.

Further, on the basis of the nucleotide sequence of DNA determined in the above, an intended DNA can also be prepared by chemical synthesis using an 8905 type DNA synthesis device manufactured by PerSeptive Biosystems or the like.

The above transformant that expresses the terephthalate 1,2-dioxygenase oxygenase large subunit protein, terephthalate 1,2-dioxygenase oxygenase small subunit protein, terephthalate 1,2-dioxygenase reductase protein, terephthalic acid transporter protein, TPA-DHD dehydrogenase protein, para-hydroxybenzoate hydroxylase protein, lactaldehyde reductase protein, and/or lactaldehyde dehydrogenase protein can be obtained by expressing the above DNA in host cells using the following method.

When DNA coding for the above protein is used, a DNA fragment with appropriate length can be prepared as necessary, which DNA fragment contains a part coding for the protein to be used in the present invention. Further, nucleotides can be substituted such that the nucleotide sequence of the part coding for such a protein has a codon optimal for expression in a host to thereby improve a rate of producing such a protein. A transformant that expresses DNA to be used in the present invention can be obtained by inserting the above DNA fragment in the downstream of a promoter of an appropriate expression vector to prepare a recombinant DNA and introducing such a recombinant DNA into host cells suitable for such an expression vector.

As a host in which the protein to be used in the present invention is expressed, any host including bacteria, yeasts, animal cells, insect cells, and plant cells can be used as long as it is a host capable of expressing an intended gene. Preferably, a microorganism that does not originally have a capacity to metabolize TPA-DHD can be used. More preferred examples include bacteria of the genus *Escherichia* or bacteria of the genus *Pseudomonas*, both of which do not originally have a capacity to metabolize TPA-DHD. Still more preferred examples include *Escherichia coli* K-12 strain and *Pseudomonas putida* KT2440 strain.

As an expression vector, one capable of autonomously replicating in the above host cells or of being incorporated in the chromosome thereof, and capable of containing a promoter at a position where DNA to be used in the present invention can be transcribed.

In cases where prokaryotes such as bacteria are used as host cells, a recombinant DNA comprising the DNA to be used in the present invention is preferably a recombinant DNA composed of a promoter, ribosome binding sequence, DNA used in the present invention, and transcription termination sequence concurrently with being capable of autonomously replicating the prokaryote. A gene that controls the promoter may be contained.

A vector for introducing a DNA coding for the protein to be used in the present invention or a fusion protein of such a protein with another protein into a microorganism such as *Escherichia coli* to express is preferably a so-called multi-copy type; and examples thereof include plasmids having the origin of replication derived from ColE1 including, for example, pUC-based plasmids and pBR322-based plasmids; and derivatives thereof. Here, a "derivative" means a plasmid in which bases are subjected to modification by substitution, deletion, insertion, addition, inversion, and/or the like. The modification used herein includes mutagenesis treatment by mutagens, UV irradiation, or the like; and modification by natural mutation or the like. To be more specific, pUC19 (Gene, 33, 103 (1985)), pUC18, pBR322, pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pBluescript II SK(+), pBluescript II KS(+) (manufactured by Stratagene), pSTV28 (manufactured by Takara Bio Inc.), pUC118 (manufactured by Takara Bio Inc.), or the like can, for example, be used as the vector.

As a promoter, any promoter may be employed as long as it is one capable of expressing in host cells such as *Escherichia coli*. For instance, promoters derived from *Escherichia coli*, phage, or the like such as trp promoter (Ptrp), lac promoter (Plac), PL promoter, PR promoter, T7 promoter, or the like, or tac promoter; promoters that are artificially designed and modified like lacT7 promoter; or Pm promoter that is controlled by XylS protein of TOL plasmid of *Pseudomonas putida* can be used.

It is preferred to use a plasmid in which a distance between a Shine-Dalgarno sequence which is a ribosome binding sequence and the start codon is adjusted to a proper distance (for example 5 to 18 bases). In the recombinant DNA used in the present invention, although a transcription termination sequence is not necessarily required for expression of the DNA used in the present invention, it is preferred to arrange the transcription termination sequence immediately after the structural gene.

A microorganism whose production amount of any one or more of the above proteins is enhanced, as compared with the counterpart of a parent strain, can be created using a recombinant DNA technique or the like to increase the production amount of TPA-DHD, protocatechuic acid, or gallic acid. To be specific, examples include use of a promoter that exhibits a stronger transcription activity than a natural promoter as a promoter for expressing a gene coding for any of the above proteins, use of a terminator that exhibits a stronger transcription termination activity than a natural terminator as a terminator for terminating transcription of a gene coding for such a protein, use of a high copy number vector as an expression vector, or incorporation into the chromosome by homologous recombination.

By using a microorganism expressing the terephthalate 1,2-dioxygenase oxygenase large subunit protein, terephthalate 1,2-dioxygenase oxygenase small subunit protein, and terephthalate 1,2-dioxygenase reductase protein, which are obtained as described above, TPA-DHD can be produced from terephthalic acid salt. For instance, by culturing such a microorganism in a liquid medium and then adding a terephthalic acid salt containing 0.5 times or more and twice or less the amount of potassium based on all of the terephthalic acids contained in the terephthalic acid salt in terms of moles to the culture solution of such a microorganism such that the concentration thereof is 0.1 mM to 1 M, TPA-DHD can be generated and accumulated, and then TPA-DHD can be collected from such a culture solution. As for a method of culturing the microorganism to be used in the present invention in a medium, the culturing can be carried out according to a method that is commonly used in culturing the microorganism.

Further, TPA-DHD can also be produced by culturing the above microorganism and then adding cultured bacterial cells of such a microorganism or a processed product of such cultured bacterial cells to an aqueous medium containing a terephthalic acid salt containing 0.5 times or more and twice or less the amount of potassium based on all of the terephthalic acids contained in the terephthalic acid salt in terms of moles to generate and accumulate TPA-DHD and then to collect TPA-DHD from such a medium.

By using a microorganism expressing a terephthalate 1,2-dioxygenase oxygenase large subunit protein, terephthalate 1,2-dioxygenase oxygenase small subunit protein, terephthalate 1,2-dioxygenase reductase protein, and TPA-DHD dehydrogenase, protocatechuic acid can be produced from terephthalate. For instance, by culturing such a microorganism in a liquid medium and then adding a terephthalic acid salt containing 0.5 times or more and twice or less the amount of potassium based on all of the terephthalic acids contained in the terephthalic acid salt in terms of moles in the culture solution of such a microorganism such that the concentration thereof is 0.1 mM to 1 M, protocatechuic acid can be generated and accumulated, and then protocatechuic acid can be collected from such a culture solution. As for a method of culturing the microorganism used in the present invention in a medium, the culturing can be carried out according to a method that is commonly used in culturing a microorganism.

Further, protocatechuic acid can also be produced by culturing the above microorganism and then adding cultured bacterial cells of such a microorganism or a processed product of such cultured bacterial cells in an aqueous medium containing a terephthalic acid salt containing 0.5 times or more and twice or less the amount of potassium based on all of the terephthalic acids contained in the terephthalic acid salt in terms of moles to generate and accumulate protocatechuic acid and then to collect protocatechuic acid form such a medium.

Further, protocatechuic acid can also be produced by generating TPA-DHD from terephthalic acid salt by the method described in the above-mentioned (1) to (4), then converting TPA-DHD into protocatechuic acid using the culture of another microorganism obtained by introducing DNA shown in the above-mentioned (q), (r), (s) or (t) by a transformation method or a processed product of such a culture, and collecting protocatechuic acid from such a culture solution or such a medium.

By using a microorganism expressing a terephthalate 1,2-dioxygenase oxygenase large subunit protein, terephthalate 1,2-dioxygenase oxygenase small subunit protein, terephthalate 1,2-dioxygenase reductase protein, TPA-DHD dehydrogenase, and para-hydroxybenzoate hydroxylase, gallic acid can be produced from terephthalic acid salt. For instance, by culturing such a microorganism in a liquid medium and then adding a terephthalic acid salt containing 0.5 times or more and twice or less the amount of potassium based on all of the terephthalic acids contained in the terephthalic acid salt in terms of moles to the culture solution of such a microorganism such that the concentration thereof is 0.1 mM to 1 M, gallic acid can be generated and accumulated, and then gallic acid can be collected from such a culture solution. As for a method of culturing the microorganism used in the present invention in a medium, the culturing can be carried out according to a method that is commonly used in culturing a microorganism.

Further, gallic acid can also be produced by culturing the above microorganism and then adding cultured bacterial cells of such a microorganism or a processed product of such cultured bacterial cells to an aqueous medium containing a terephthalic acid salt containing 0.5 times or more and twice or less the amount of potassium based on all of the terephthalic acids contained in the terephthalic acid salt in terms of moles to generate and accumulate gallic acid and then to collect gallic acid form such a medium.

Further, gallic acid can also be produced by generating TPA-DHD from terephthalic acid salt by the method described in the above-mentioned (1) to (4), then converting TPA-DHD into gallic acid using the culture of another microorganism obtained by introducing DNA shown in the above-mentioned (q), (r), (s), or (t) and DNA shown in the above-mentioned (u), (v), (w), or (x) by a transformation method or a processed product of such a culture, and collecting gallic acid from such a culture solution or such a medium.

As a terephthalic acid salt containing 0.5 times or more and twice or less the amount of potassium based on all of the terephthalic acids contained in the terephthalic acid salt in terms of moles, a high-purity terephthalic acid salt containing potassium terephthalate such as dipotassium terephthalate, 1-potassium 4-sodium terephthalate, or 1-potassium 4-ammonium terephthalate may be used. One obtained from waste polyesters may also be used. The following will describe a method of obtaining a terephthalic acid salt containing 0.5 times or more and twice or less the amount of potassium based on all of the terephthalic acids contained in the terephthalic acid salt in terms of moles that is used as a raw material of compound production by a microorganism from waste polyesters.

As for a form of waste polyesters, one in any form including vessels, films, sheets, parts, fibers, granular ground products, and powder ground products can be utilized. Polyester waste materials having these polyesters as major components (the major components mean containing, for example, 80% or more of PET and/or PTT and/or PBT) and containing foreign substances (main components thereof include polyethylene and polypropylene) are collected. The foreign substance such as metals and plastics other than polyesters is removed as necessary and then the polyester waste material is ground by a grinder mill. As the ground product of the polyester waste material, flakes of PET bottles can be used as a starting raw material, which flakes are processed and handled by a PET bottle recycling supplier. By processing the thus obtained ground product of the polyester waste material by a specific gravity fractionation method, metal a separation method by a magnet, a washing method by water, a method of removing floating foreign substances with water, or the like, foreign substances and/or contaminating substances such as metals, glass, stones, residues of food products or beverages, plastics other than polyesters, or polyethylene or polypropylene sheet are separated from the polyester ground product.

The thus obtained polyester ground product is weighed to measure the content (the number of moles) of terephthalic acid and placed in a metal reaction tank. Further, potassium hydroxide or a mixture of potassium hydroxide and sodium hydroxide, and a reaction solvent of either ethylene glycol or 1-butanol are added to the reaction tank; and then the resulting mixture is heated only for a proper period of time to thereby carry out a depolymerization reaction of the polyester ground product. Inclusion of an appropriate amount of water in a solution of the depolymerization reaction leads to faster proceeding of the reaction, and, on the top of that, to improvement of the yield of terephthalic acid salt that can be collected.

The potassium hydroxide or sodium hydroxide to be added can be added in a form of either solid particle or aqueous solution; and is preferably added so as to be about twice the number of moles, preferably a total of 2 to 2.2 times the number of moles based on the number of moles of terephthalic acid in the polyester ground product placed in the reaction tank. More preferably, the amount of alkali to be added may be a total of 2.10 times the number of moles based on the content of terephthalic acid in the polyester ground product.

The ethylene glycol or 1-butanol to be added is preferably added such that the amount thereof is 3 to 10 times based on the volume of such a polyester ground product. More preferably, the amount of the solvent to be added may be 5 times. It is desired to add an appropriate amount of water in a solution of such a depolymerization reaction. The total amount of water to be contained in the solution of such a depolymerization reaction is desirably 1 to 5 times based on the number of moles of terephthalic acid in the polyester ground product.

The pressure in a reaction tank is preferably pressure near atmospheric pressure, for example, 0.9 to 1.1 atm (91.193 to 111.458 kPa). The reaction temperature when ethylene glycol is used as a reaction solvent is a temperature at which water evaporates whereas ethylene glycol does not evaporate. When the pressure in the reaction tank is 1 atm, the temperature is preferably 100 to 196° C. When a reaction is carried out at a pressure of lower than 1 atm, the reaction is carried out at a temperature at which water evaporates whereas ethylene glycol does not evaporate in the range of 100 to 196° C. Further, when a reaction is carried out at a pressure of higher than 1 atm, the reaction is carried out at a temperature at which water evaporates whereas ethylene glycol does not evaporate in the range of 100 to 196° C. The reaction temperature when 1-butanol is used as a reaction solvent is a temperature at which water evaporates whereas 1-butanol does not evaporate. When the pressure in the reaction tank is 1 atm, the temperature is preferably 100 to 116° C. When a reaction is carried out at a pressure of lower than 1 atm, the reaction is carried out at a temperature at which water evaporates whereas 1-butanol does not evaporate in the range of 100 to 116° C. Further, when a reaction is carried out at a pressure of higher than 1 atm, the reaction is carried out at a temperature at which water evaporates whereas 1-butanol does not evaporate in the range of 100 to 116° C.

A period of time of heating is preferably a period of time of completely decomposing a polyester ground product, and usually 10 to 240 minutes. Yet, because a rate of dissolution in the order of from the highest to the lowest is PET, PTT, and PBT, it is, when PTT or PBT is depolymerized, desired to increase a period of time of heating and decomposition. Volatile substances such as water which evaporate during a heating reaction are collected by a condenser.

After completion of the depolymerization reaction, when foreign substance plastics other than polyester including, for example, polyethylene, polypropylene, polystyrene, and vinyl chloride, in addition to the solution of ethylene glycol or 1-butanol and solids derived from terephthalates, are present as floating substances, such floating substances are removed. After that, the solid of terephthalic acids is separated from an ethylene glycol solvent or 1-butanol solvent by a solid-liquid separation method such as filtration or centrifugal treatment.

Because significant amounts of terephthalic acid salts are dissolved in an ethylene glycol solvent separated by the above solid-liquid separation method, it is preferred to use such a solvent as a solvent for the above depolymerization reaction of PET, PTT, or PBT. Further, although the solubility of terephthalic acid salt in a 1-butanol solvent is low, reuse of 1-butanol solvent used in the depolymerization reaction as a solvent for the above depolymerization reaction of PET, PTT, or PBT is preferred because the production cost can be more reduced. As just described, the ethylene glycol solvent and 1-butanol solvent used in the depolymerization reaction of PET, PTT, or PBT can be repeatedly used in the depolymerization reaction of polyester by separating the generated terephthalates.

Subsequently, in cases where a large amount of impure substances are contained in solids of terephthalic acid salts, the obtained solids of terephthalic acid salts may be subjected to washing treatment with an appropriate amount of ethylene glycol or 1-butanol. In particular, in cases where polyester waste materials containing PIT or PBT are depolymerized, 1,3-propanediol or 1,4-butanediol are mixed in such solids and it is therefore preferred to carry out washing treatment with ethylene glycol or 1-butanol. Further, in cases where a PET resin is depolymerized in a 1-butanol reaction solvent, ethylene glycol is mixed in such solids. Although such an ethylene glycol can be remove by drying under reduced pressure which is described below, such an ethylene glycol may be removed by washing treatment with 1-butanol.

Because the thus obtained solid of terephthalic acid salts contains a significant amount of ethylene glycol or 1-butanol, treatment of decreasing ethylene glycol or 1-butanol in such a solid of terephthalic acid salts using a decompression dryer or the like, or separation of liquid substances using a centrifuge or the like is carried out as necessary. A terephthalic acid salt containing 0.5 times or more and twice or less the amount of potassium based on all of the terephthalic acids contained in terms of moles contained in the thus obtained terephthalic acid salts can be used in production of TPA-DHD, protocatechuic acid, or gallic acid. Further, in cases where solid foreign substances with poor water solubility are mixed in such a terephthalic acid salt, an aqueous solution of terephthalic acid salt obtained by dissolving such a terephthalic acid salt in an appropriate amount of water and then removing the foreign substance by a filtration method may be used in compound production by a microorganism.

It is to be noted that, in order to decompose ethylene glycol mixed in terephthalic acid salts obtained by depolymerization of waste polyesters in an ethylene glycol solvent, by culturing a microorganism used in the present invention whose expression amount of lactaldehyde reductase and lactaldehyde dehydrogenase is enhanced in a liquid medium and then adding a terephthalic acid salt containing ethylene glycol and containing 0.5 times or more and twice or less the amount of potassium based on all of the terephthalic acids contained in the terephthalic acid salt in terms of moles in a culture solution such that the concentration thereof is 0.1 mM to 1 M, TPA-DHD, protocatechuic acid, or gallic acid can be generated while decomposing ethylene glycol.

By culturing the microorganism to be used in the present invention and then adding cultured bacterial cells of such a microorganism or a processed product of such cultured bacterial cells in an aqueous medium containing a terephthalic acid salt containing 0.5 times or more and twice or less the amount of potassium based on all of the terephthalic acids contained in the terephthalic acid salt in terms of moles, TPA-DHD, protocatechuic acid, or gallic acid can also be generated and accumulated and then TPA-DHD, protocatechuic acid, or gallic acid can be collected from such a medium.

The culture of the microorganism to be used in the present invention can be carried out in a common nutrient medium containing carbon sources, nitrogen sources, inorganic salts, various vitamins or the like. As the carbon source, for example, sugars such as glucose, sucrose, or fructose, alcohols such as ethanol or methanol, organic acids such as citric acid, malic acid, or succinic acid, blackstrap molasses, or the like is used. As the nitrogen source, for example, ammonia, ammonium sulfate, ammonium chloride, ammonium nitrate, urea, or the like is solely used; or a mixture thereof is used. In addition, as the inorganic salt, for example, potassium monohydrogen phosphate, potassium dihydrogen phosphate, magnesium sulfate, or the like is used. Besides, nutrients including peptone, meat extract, yeast extract, corn steep liquor, casamino acid, and various vitamins such as biotin can be added in the medium. As a raw material for producing for TPA-DHD, protocatechuic acid, or gallic acid, a terephthalic acid salt containing 0.5 times or more and twice or less the amount of potassium based on all of the terephthalic acids contained in the terephthalic acid salt in terms of moles, prepared as described above, is added.

The culture is usually carried out under aerobic conditions such as aeration stirring or shaking. A culture temperature is not particularly restricted as long as it is a temperature at which the microorganism used in the present invention can grow. Further, a pH in the course of culturing is not particularly restricted either as long as it is a pH at which the microorganism used in the present invention can grow. The adjustment of pH during the culturing can be carried out by adding an acid or alkali.

As a processed product of such cultured bacterial cells, one obtained by immobilizing the microorganism to be used in the present invention to a carrier may be used. In that case, bacterial cells collected from a culture can be used as they are; or bacterial cells washed with an appropriate buffer such as about 0.02 to 0.2 M phosphate buffer solution (pH 6 to 10) can be used. Further, a ground product obtained by grounding the bacterial cells collected from the culture by means such as ultrasonic wave or compression; an extract containing the protein to be used in the present invention, which extract is obtained by extracting such a ground product with water; or one obtained by immobilizing a partially purified component or the like of the protein to be used in the present invention to a carrier, which partially purified component is obtained by further subjecting such an extract to treatment such as ammonium sulfate precipitation or column chromatography, can also be used in production of the TPA-DHD, protocatechuic acid, or gallic acid of the present invention.

The immobilization of these bacterial cells, ground products of bacterial cells, extracts or purified enzymes can be carried out, according to a method that is known per se and commonly used, by a method of immobilizing the bacterial cells or the like to an appropriate carrier such as an acrylamide monomer, alginic acid, or carrageenan.

As for an aqueous medium to be used in a reaction, an aqueous solution or appropriate buffer, for example, about 0.02 to 0.2 M phosphate buffer solution (pH 6 to 10), that contains terephthalic acid salts can be used. To this aqueous medium, when the permeability of the plasma membrane of bacterial cells is required to be further enhanced, toluene, xylene, nonionic surfactant, or the like can be added at a concentration of 0.05 to 2.0% (w/v).

It is appropriate that the concentration of terephthalic acid salt that serves as a reaction raw material in an aqueous medium is about 0.1 mM to 1 M. The temperature and pH of an enzymatic reaction in the above aqueous medium are not particularly restricted. It is appropriate that the temperature is usually 10 to 60° C. and preferably 15 to 50° C.; and the pH in a reaction solution can be set to 5 to 10 and preferably in the vicinity of 6 to 9. The adjustment of pH can be carried out by adding an acid or alkali.

The enzyme to be used in the invention can be obtained by suspending a bacterial cell extraction liquid as it is or one collected by subjecting the bacterial cell extraction liquid to centrifugation, filtration, or the like in water or a buffer. The thus obtained enzyme is allowed to react in the presence of terephthalic acid salts. It is advantageous that the concentration of the terephthalic acid salt in a reaction solution is set to as high as possible within the range where the activity of the enzyme is not inhibited. The reaction may be carried out by any method of still standing, stirring, and shaking. Further, a method comprising filling the enzyme that is immobilized to an appropriate support in a column and running a solution containing the terephthalates can also be used. The reaction is carried out at usually 10 to 60° C. and preferably 15 to 50° C., and at pH 5 to 9 and preferably pH 6 to 9.

Further, addition of an antioxidant or reductant in the above an aqueous medium at the time of the reaction may in some cases further improve the generation yield of TPA-DI-HD, protocatechuic acid, or gallic acid. Examples of the antioxidant/reductant include ascorbic acid, isoascorbic acid, cysteine, sulfites such as sulfite sodium or sodium hydrogen sulfite, and thiosulfate salts such as sodium thiosulfate. The added concentration varies in the types of the antioxidant/reductant. It is desired to add at a concentration at which the generation of TPA-DHD, protocatechuic acid, or gallic acid is not inhibited. The concentration is usually 0.001 to 5% (w/v) and preferably 0.005 to 1%.

Further, addition of an oxidant in the above an aqueous medium at the time of the reaction may in some cases further improve the generation yield of TPA-DHD, protocatechuic acid, or gallic acid. Examples of the oxidant include nitrate such as sodium nitrite or potassium nitrite, metal salts such as ferric chloride or ferric sulfate, halogen, and peroxy acid. Preferred is sodium nitrite, ferric chloride, or ferric sulfate. The added concentration varies in the types of the oxidant. It is desired to add at a concentration at which the generation of TPA-DHD, protocatechuic acid, or gallic acid is not inhibited. The concentration is usually 0.001 to 0.05% (w/v) and preferably 0.005 to 0.02%.

TPA-DHD, protocatechuic acid, or gallic acid in a culture solution after completion of the culturing or a reaction solution can be, after removing as necessary insoluble materials such as bacterial cells from such a culture solution by centrifugation or the like, subjected to methods including, for example, an extraction method by an organic solvent such as ethyl acetate, a method using active carbons, a method using an ion-exchange resin, a precipitation method such as a crystallization method or salting-out, and a distillation method solely or in combination to thereby collect TPA-DHD, protocatechuic acid or gallic acid. When TPA-DHD, protocatechuic acid, or gallic acid is required to be obtained not in a form of salt but in a state of acid, carboxylic acid that forms the salt can become a form of free acid in by adding sulfuric acid, hydrochloric acid, or the like in the above purification step to lower the pH.

By way of the examples, the method of the present invention will now be concretely described below. However, the present invention is by no means limited thereto.

Examples

Example 1

Measurement of the Solubility of Various Terephthalic Acid Salts 2.99 g (0.018 mol) of terephthalic acid (in a form of powder, manufactured by Sigma-Aldrich Japan; hereinafter, unless otherwise specified, reagents used were ones manufactured by Sigma-Aldrich Japan) and 0.036 mol of potassium hydroxide (in a form of granule) were put in a 50 mL-glass beaker. Distilled water was filled to obtain a volume of about 15 mL. The resulting mixture was covered with aluminum foil as a lid, heated at 50° C. for 60 minutes while stirred by a hot stirrer (manufactured by AS ONE Corporation), and allowed to cool to 30° C. After stirring at 30° C. for 120 minutes or more and confirming the precipitate remained in the solution, 1 mL of the solution was collected and subjected to centrifugation using a high speed micro centrifuge (manufactured by Tomy Seiko Co., Ltd.) (30° C., 14000 rpm (17800 g), 30 seconds) to collect the supernatant.

The concentration of terephthalic acid in this supernatant was measured and regarded as the solubility of dipotassium terephthalate. With regard to the measurement of the concentration of terephthalic acid, the sample was diluted 16,000-fold with 2.5% aqueous acetonitrile solution and analyzed in separation conditions of Table 1 using high performance liquid chromatography (Waters Corporation, LCT Premier XE). Thereafter, the concentration was calculated on the basis of a ratio of the area of terephthalic acid peaks using aqueous terephthalic acid solution with a known concentration as a control.

TABLE 1

| Condition for HPLC analysis using LCT Premier XE | |
|---|---|
| HPCL separation column | ACQUITY UPLC HSS T3 (manufactured by Waters, inner diameter 2.1 mm, length 50 mm) |
| Column temperature | 40° C. |
| Flow rale of solvent | 0.4 ml/min |
| Mobile phase A | Water |
| Mobile phase B | Acetonitrile |
| Gradient condition | 0 min (start) 2% mobile phase B |
| | 0.75 min 5% mobile phase B |
| | 1.75 min 30% mobile phase B |
| | 1.76 min 5% mobile phase B |
| | 2.50 min 5% mobile phase B |

In the same manner as the above method of preparing the aqueous solution of dipotassium terephthalate, 0.036 mol of sodium hydroxide (in a form of granule); 0.036 mol of 28% ammonium solution; 0.018 mol of potassium hydroxide and 0.018 mol of sodium hydroxide; 0.018 mol of potassium hydroxide and 0.018 mol of 28% ammonium solution; or 0.018 mol of sodium hydroxide and 0.018 mol of 28% ammonium solution was added to 2.99 g (0.018 mol) of terephthalic acid (in a form of powder) to prepare an aqueous solution of disodium terephthalate, diammonium terephthalate, 1-potassium 4-sodium terephthalate, 1-potassium 4-ammonium terephthalate, or 1-sodium 4-ammonium terephthalate and then the solubility of each of the terephthalic acid salts was measured.

The obtained solubility of each of the terephthalic acid salts is shown in Table 2. From the results of Table 2, it was found out that the solubility in water in the order of the highest to lowest was: dipotassium terephthalate, 1-potassium 4-sodium terephthalate, 1-potassium 4-ammonium terephthalate, disodium terephthalate, 1-sodium 4-ammonium terephthalate, and diammonium terephthalate; and that a salt in which at least one carboxyl group residue of the terephthalic acid forms a salt in conjunction with potassium had an excellent solubility.

TABLE 2

Solubility of terephthalic acid salts in water

| Type of terephthalate | Alkali | Solubility (mol/L) |
|---|---|---|
| Dipotassium terephthalate | Potassium hydroxide | 1.011 |
| Disodium terephthalate | Sodium hydroxide | 0.630 |
| Diammonium terephthalate | Ammonia | 0.512 |
| 1-potassium 4-sodium terephthalate | Potassium hydroxide, sodium hydroxide | 0.956 |
| 1-potassium 4-ammonium terephthalate | Potassium hydroxide, ammonia | 0.845 |
| 1-sodium-ammonium terephthalate | Potassium hydroxide, ammonia | 0.612 |

Example 2

Difference in the Capacity in Production of TPA-DHD According to Difference in Terephthalic Acid Salts Based on the results of Example 1, on the basis of terephthalic acid, potassium hydroxide, sodium hydroxide, 28% ammonium solution and distilled water, 0.6 M dipotassium terephthalate aqueous solution, 0.6 M 1-potassium 4-sodium terephthalate aqueous solution, 0.6 M 1-potassium 4-ammonium terephthalate aqueous solution, and 0.6 M disodium terephthalate aqueous solution were prepared 500 mL each. 30 ml of these terephthalic acid salt solutions and 7 g of glucose were mixed to prepare a glucose and substrate mixed solution.

A TPA-DHD production plasmid pUXPEaLT_tphA2A3A1_tpaK constructed in Reference Example 3 was introduced into *Escherichia coli* M7032 strain (obtained from CGSC of Yale University) by a transformation method to obtain a recombinant *Escherichia coli* strain M7032 (pUXPEaLT_tphA2A3A1_tpaK).

This transformant was cultured in 1 ml of LB liquid medium (10 g/l tryptone (manufactured by Difco), 5 g/l dried yeast extract (manufactured by Difco), 10 g/l sodium chloride) containing ampicillin at a final concentration of 100 mg/1 overnight. Next, merely 1% of this overnight culture was inoculated in 10 ml of F6.6W/P100/G2 medium containing ampicillin at a final concentration of 100 mg/I and cultured at 30° C. for 24 hours. It is to be noted that F6.6W/P100/G2 medium refers to an aqueous solution containing potassium dihydrogen phosphate 13.6 g/L, citric acid monohydrate 2.1 g/L, ammonium sulfate 9.9 g/L, ferrous sulfate (II) heptahydrate 1.703 g/L, glucose 20 g/L, magnesium sulfate heptahydrate 246 mg/ml, calcium chloride dihydrate 12.9 mg/L, thiamine hydrochloride 10 mg/L, magnesium oxide 10.75 mg/L, calcium carbonate 2 mg/L, zinc sulfate heptahydrate 4.5 mg/ml, manganese sulfate (II) tetrahydrate 1.12 mg/L, copper sulfate (II) pentahydrate 0.25 mg/L, cobalt sulfate (II) heptahydrate 0.28 g/L, and boric acid 0.06 mg/L.

Next, in order to carry out main culture based on this preculture, 65 ml of F6.6W/P10/G1 medium which is a main culture medium was put in an octuple mini jar fermentor (manufactured by ABLE Corporation) and adjusted to 30.2° C.±0.2 and pH 6.9±0.1. It is to be noted that F6.6W/P10/G1 medium refers to an aqueous solution containing potassium dihydrogen phosphate 1.36 g/L, citric acid monohydrate 2.1 g/L, ammonium sulfate 9.9 g/L, ferrous sulfate (II) heptahydrate 1.703 g/L, glucose 20 g/L, magnesium sulfate heptahydrate 246 mg/ml, calcium chloride dihydrate 12.9 mg/L, thiamine 10 mg/L, magnesium oxide 10.75 mg/L, calcium carbonate 2 mg/L, zinc sulfate heptahydrate 4.5 mg/ml, manganese sulfate tetrahydrate 1.12 mg/L, copper sulfate pentahydrate 0.2 5 mg/L, cobalt sulfate heptahydrate 0.28 g/L, and boric acid 0.06 mg/L.

The aeration condition of the jar fermentor culture was adjusted to 1 vvm and the adjustment of the pH of the culture was carried out using an ammonium solution and sulfuric acid. Further, dissolved oxygen in the culture solution was regulated as a saturated oxygen concentration of 100% and controlled with the revolution of stirring blade such that the dissolved oxygen is maintained at 15%, which dissolved oxygen decreasing as bacterial cells grow.

In a main culture medium, 0.1% of preculture was inoculated and cultured in the above condition. When the bacterial cell turbidity reached about 7 at an absorbance of 600 nm, an inducer, m-toluic acid was added such that the final concentration thereof was 1 mM to express a terephthalate 1,2-dioxygenase protein, terephthalate 1,2-dioxygenase reductase protein, and terephthalic acid transporter protein. The glucose concentration was measured with time. When the glucose concentration reached 0, the glucose and substrate mixed solution was administered.

Sampling was carried out 48 hours after the start of the main culture. Each of the samples was subjected to analysis in conditions shown in Table 1 by an LC-TOF type mass spectrometer (Waters Corporation, LCT Premier XE). Identification of terephthalic acid was carried out with a combination of retention time of high performance liquid chromatography and an accurate mass value from the mass spectrometer, comparing to a standard sample of terephthalic acid. Among substances appeared as terephthalic acid decreased, TPA-DHD was identified on the basis of a predicted accurate mass value of TPA-DHD. Further, quantification of TPA-DHD was carried out on the basis of a calibration curve prepared from an amount of terephthalic acid decreased and an increase in the peak area of TPA-DHD.

As a result, it was observed that TPA-DHD increased as terephthalic acid decreased. Table 3 shows a ratio with the amount of TPA-DHD produced from each of the terephthalic acid salts 48 hours after the start of the culture as 100%. From the results shown in Table 3, it became clear that all of 3 kinds of the potassium terephthalates exhibited a superior capacity in production of TPA-DHD to production of disodium terephthalate.

TABLE 3

Difference in the capacity in production of TPA-DHD among terephthalic acid salts

| Terephthalate used as a raw material | TPA-DHD (g/L) | Ratio of the capacity in production |
|---|---|---|
| Disodium terephthalate | 9.7 | 100% |
| Dipotassium terephthalate | 11.3 | 116% |
| 1-potassium 4-sodium terephthalate | 10.7 | 110% |
| 1-potassium 4-ammonium terephthalate | 12.2 | 126% |

Example 3

Difference in the Capacity in Production of TPA-DHD Among the Concentrations of Potassium Ion in Terephthalic Acid Salts The results of Example 2 showed that use of potassium terephthalate as a raw material resulted in an excellent capacity in production of TPA-DHD. Having this in mind, effects of the concentration of potassium ion in terephthalic acid salt on TPA-DHD was examined as follows:

First, 0.6 M dipotassium terephthalate aqueous solution and 0.6 M disodium terephthalate aqueous solution, both of which were prepared in Example 2, were mixed at a ratio of 0:100, 20:80, 25:75, 30:70, 35:65, and 50:50 to prepare each aqueous solution of the terephthalic acid salts. These terephthalic acid salt solutions 30 ml and glucose 7 g were mixed to obtain glucose and substrate mixed solutions.

Using these glucose and substrate mixed solutions, the capacity of recombinant *Escherichia coli* strain M7032 (pUXPEaLT_tphA2A3A1_tpaK) in production of TPA-DHD was examined by the same method as the method of Example 2. The results are shown in Table 4.

As a result, as shown in Table 4, a phenomenon where the capacity in production of TPA-DHD increased as the potassium ion content in the terephthalic acid salt increased was observed; and it was shown that the capacity in production of TPA-DHD was higher when the terephthalic acid salt containing 0.5 times or more the amount of potassium based on all of the terephthalic acids contained in the terephthalic acid salt in terms of moles is used, as compared with the capacity in production when disodium terephthalate was used as a raw materials.

TABLE 4

Difference in the capacity in production of TPA-DHD among the concentrations of potassium ion in terephthalic acid salts

| Mixing ratio between dipotassium terephthalate and disodium terephthalate | 51 hours after the start of the main culture | | 73 hours after the start of the main culture | |
|---|---|---|---|---|
| | TPA-DHD (g/L) | Ratio of the capacity in production | TPA-DHD (g/L) | Ratio of the capacity in production |
| 0:100 | 15.2 | 100% | 17.4 | 100% |
| 20:80 | 15.0 | 99% | 18.1 | 104% |
| 25:75 | 15.6 | 103% | 18.0 | 103% |
| 30:70 | 16.5 | 109% | 19.6 | 113% |
| 35:65 | 16.9 | 111% | 19.4 | 111% |
| 50:50 | 17.2 | 113% | 20.5 | 118% |

Example 4

Difference in the Capacity in Production of Protocatechuic Acid According to Difference in Terephthalic Acid Salts A protocatechuic acid-producing plasmid pUXPEaLT_tphA2A3BA1_tpaK constructed in Reference Example 2 was introduced into *Escherichia coli* M7032 strain by a transformation method to obtain a protocatechuic acid-producing *Escherichia coli* strain M7032 (pUXPEaLT_tphA2A3BA1_tpaK).

Subsequently, in the same manner as described in Example 2, the preculture of the present protocatechuic acid-producing bacterium was prepared and then merely 2% of such a preculture was inoculated in a main culture medium to carry out main culture. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, terephthalate dihydrodiol dehydrogenase protein, and terephthalic acid transporter protein. The glucose concentration was measured with time. When the glucose concentration reached 0, the glucose and substrate mixed solution was administered.

Sampling was carried out 48 hours after the start of the main culture. Each of the samples was subjected to analysis by an LC-TOF type mass spectrometer (Waters Corporation, LCT Premier XE). Identification of terephthalic acid and protocatechuic acid was carried out with a combination of retention time of high performance liquid chromatography and an accurate mass value from the mass spectrometer, comparing to a standard sample of terephthalic acid and protocatechuic acid.

As a result, it was observed that protocatechuic acid increased as terephthalic acid decreased. Table 5 shows a ratio with the amount of protocatechuic acid produced from each of the terephthalates 48 hours after the start of the culture as 100%. From the results shown in Table 5, it became clear that all of 3 kinds of the potassium terephthalates exhibited a superior capacity in production of protocatechuic acid to production of disodium terephthalate.

TABLE 5

Difference in the capacity in production of protocatechuic acid among terephthalates

| Terephthalate used as a raw material | Protocatechuic acid (g/L) | Ratio of the capacity in production |
|---|---|---|
| Disodium terephthalate | 5.0 | 100% |
| Dipotassium terephthalate | 8.3 | 166% |
| 1-potassium 4-sodium terephthalate | 7.7 | 154% |
| 1-potassium 4-ammonium terephthalate | 7.1 | 142% |

Example 5

Difference in the Capacity in Production of Gallic Acid According to Difference in Terephthalic Acid Salts A gallic acid plasmid pUXPEaLT_HFM145_tphA2A3BA1_tpaK constructed in Reference Example 2 was introduced into *Escherichia coli* M7032 strain by a transformation method to obtain a gallic acid-producing *Escherichia coli* strain M7032 (pUXPEaLT_HFM145_tphA2A3BA1_tpaK). Subsequently, in the same manner as described in Example 2, the preculture of this gallic acid-producing bacterium was prepared and then merely 2% of this preculture was inoculated in a main culture medium to carry out main culture in the above condition. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, terephthalate dihydrodiol dehydrogenase protein, terephthalic acid transporter protein and improved para-hydroxybenzoate hydroxylase. The glucose concentration was measured with time. When the glucose concentration reached 0, the glucose and substrate mixed solution was administered.

Sampling was carried out 48 hours after the start of the main culture. Each of the samples was subjected to analysis by an LC-TOF type mass spectrometer (Waters Corporation, LCT Premier XE). Identification of gallic acid and protocatechuic acid was carried out with a combination of retention time of high performance liquid chromatography and an accurate mass value from the mass spectrometer, comparing to a standard sample of terephthalic acid and gallic acid.

As a result, it was observed that gallic acid increased as terephthalic acid decreased. Table 6 shows a ratio with the amount of gallic acid produced from each of the terephthalic acid salts 48 hours after the start of the culture as 100%. From the results shown in Table 6, it became clear that all of 3 kinds of the potassium terephthalates exhibited a superior capacity in the production of gallic acid to the production of disodium terephthalate.

TABLE 6

Difference in the capacity in production of gallic acid according to terephthalic acid

| Terephthalate used as a raw material | Gallic acid (g/L) | Ratio of the capacity in production |
|---|---|---|
| Disodium terephthalate | 7.6 | 100% |
| Dipotassium terephthalate | 8.6 | 113% |
| 1-potassium 4-sodium terephthalate | 8.4 | 111% |
| 1-potassium 4-ammonium terephthalate | 8.5 | 112% |

Example 6

Depolymerization of Waste PET in Ethylene Glycol Solvent (1) Difference in a Rate of Depolymerizing and Efficiency of Depolymerizing Waste PET According to the Type of Alkali Metal Hydroxide Waste PET bottles 22 kg were collected. After the label and cap thereof were separated, the bottle was washed and air-dried. This washed waste PET bottle was ground to pellets having a size enough to pass through a 5 mm-square screen, the operation of which Nippon Coke & Engineering Co., Ltd. was requested to do. This ground product was used in the following step as a waste PET bottle ground product.

In a 200 mL stainless-steel beaker (purchased from Sansyo Co., Ltd.), waste PET bottle ground product 12 g and ethylene glycol 60 g were placed. And then, potassium hydroxide (in a form of granule) 0.13 mol, sodium hydroxide (in a form of granule) 0.13 mol, or potassium hydroxide 0.066 mol, and sodium hydroxide 0.066 mol were put therein and subjected, while vigorously stirred using a hot stirrer, to heat treatment at 160° C. for 120 minutes.

Figure 2:
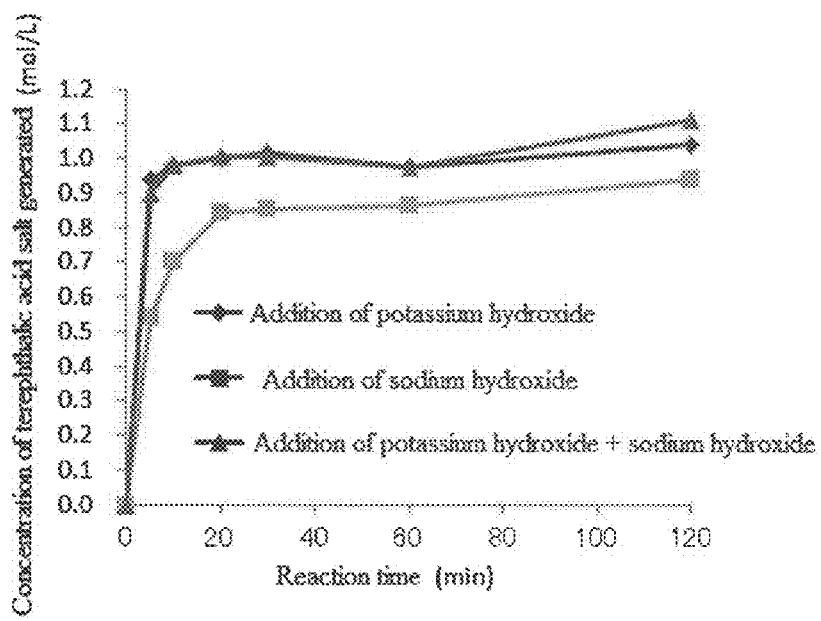
FIG. 2 is a graph showing the generation rate of terephthalic acid when waste PET is depolymerized in an ethylene glycol solvent containing potassium hydroxide and/or sodium hydroxide.

On this occasion, about 200 μL of the reaction solution was collected at the time of 0 minutes, 5 minutes, 10 minutes, 20 minutes, 30 minutes, 60 minutes, or 120 minutes after the inner temperature of the solution reached 160° C.; and the concentration of terephthalate at each of the time points was measured. FIG. 2 shows the concentration of terephthalate generated in the course of reaction time.

From the results of FIG. 2, it was found out that the addition of potassium hydroxide led to a higher rate of generating the terephthalic acid salt from the waste PET bottle ground product and moreover a superior efficiency of the generation. Further, between the case of adding potassium hydroxide alone and the case of adding both potassium hydroxide and sodium hydroxide in an equimolar amount, there was no difference in the effects.

(2) Analysis of Solid Residues after Depolymerization Reaction of Waste PET

In a 500 mL stainless-steel beaker (purchased from Sansyo Co., Ltd.), 30 g of waste PET bottle ground product and 150 g of ethylene glycol were placed. And then, 0.33 mol of potassium hydroxide (in a form of granule), 0.33 mol of sodium hydroxide (in a form of granule), or 0.17 mol of potassium hydroxide, and 0.17 mol of sodium hydroxide were put therein and subjected, while vigorously stirred using a hot stirrer, to heat treatment at 160° C. for 60 minutes. Thereafter, the resultant was allowed to naturally cool, and when the inner temperature thereof reached 40° C. or less, the content was taken out.

This content was filtered off with a filter paper (Grade 540 manufactured by Whatman) to separate residues from a filtrate and then the weight of each of the residues and the total amount of terephthalic acid in the residue were measured. The results are shown in Table 7.

In addition, the solubility of dipotassium terephthalate, disodium terephthalate, and 1-potassium 4-sodium terephthalate in ethylene glycol was examined as the same method as described in Example 1 and were then found to be 231 mM, 109 mM, and 205 mM, respectively.

Thus, it was found out that, because of a higher solubility of the terephthalic acid salt in ethylene glycol, as compared with the addition of sodium hydroxide, the addition of potassium hydroxide led to a superior efficiency of generating the terephthalic acid salt, whereas the amount of terephthalic acid collected were about the same (in terms of moles) between the case of adding potassium hydroxide and the case of adding sodium hydroxide (see Table 7).

TABLE 7

Difference in the amount of terephthalic acid produced among alkali metal hydroxides in depolymerization of PET in the ethylene glycol solvent

| Alkali metal hydroxide used in depolymerization of PET | The amount of residue collected (g) | The total amount of terephthalic acid in the residue (mmol) |
|---|---|---|
| Potassium hydroxide | 43.0 | 142.0 |
| Sodium hydroxide | 62.8 | 143.6 |
| Potassium hydroxide and sodium hydroxide | 45.4 | 120.6 |

(3) Depolymerization Reaction of Waste PET Using an Ethylene Glycol Solvent Saturated with Terephthalic Acid Salt In the step of depolymerizing waste PET, it is desired to reuse an ethylene glycol solvent obtained by separating solid residues with terephthalic acid salts as major components after the depolymerization is completed. Considering that each of the terephthalic acid salts was dissolved, in a saturated state, in the ethylene glycol solvent that had been subjected to the depolymerization reaction of waste PET, a depolymerization reaction of waste PET using the ethylene glycol solvent saturated with the terephthalic acid salt was carried out as follows:

4.15 g of terephthalic acid (0.025 mol) was placed in a 200 mL glass beaker and then 0.050 mol of potassium hydroxide (in a form of granule), 0.050 mol of sodium hydroxide (in a form of granule), or 0.025 mol of potassium hydroxide, and 0.025 mol of sodium hydroxide were placed thereto. Ethylene glycol was filled to obtain a volume of about 100 mL. The resulting mixture was covered with aluminum foil as a lid, heated at 100° C. for 60 minutes while stirred by a hot stirrer, and allowed to cool to 30° C. or less. These solutions were filtered with a filter paper (Grade 540 manufactured by Whatman) to obtain an ethylene glycol solvent saturated with the terephthalate.

The concentration of each of the terephthalates contained in such a solvent was 0.23 M in a dipotassium terephthalate saturated solution, 0.11 M in a disodium terephthalate saturated solution, and 0.20 M in a 1-potassium 4-sodium terephthalate saturated solution.

In a 200 mL stainless-steel beaker (purchased from Sansyo Co., Ltd.), 12 g of a waste PET bottle ground product was placed. And then an ethylene glycol solvent saturated with 65 g of dipotassium terephthalate and 0.13 mol of potassium hydroxide, an ethylene glycol solvent saturated with 65 g of disodium terephthalate and 0.13 mol of sodium hydroxide, or an ethylene glycol solvent saturated with 65 g of 1-potassium 4-sodium terephthalate, and 0.066 mol of potassium hydroxide and 0.066 mol of sodium hydroxide were put therein and subjected, while vigorously stirred using a hot stirrer, to heat treatment at 160° C. for 60 minutes. The resultant was allowed to cool; and when the inner temperature thereof reached 40° C. or less, the content was taken out.

This content was filtered off with a filter paper to separate residues from a filtrate and then the weight of each of the residues and the total amount of terephthalic acid in the residue were measured. From the results shown in Table 8, it was found out that the total amount of terephthalic acid in the residue after the filtration in the order of from the highest to the lowest was potassium hydroxide, the mixture of potassium hydroxide and sodium hydroxide, and sodium hydroxide.

TABLE 8

Difference in the amount of terephthalic acid produced in depolymerization of PET in the ethylene glycol solvent saturated with the terephthalic acid salt

| Solvent used in depolymerization of PET | Alkali metal hydroxide used in depolymerization of PET | The amount of residue collected (g) | The total amount of terephthalic acid in the residue (mmol) |
|---|---|---|---|
| Ethylene glycol saturated with dipotassium terephthalate | Potassium hydroxide | 21.8 | 63.9 |
| Ethylene glycol saturated with disodium terephthalate | Sodium hydroxide | 28.0 | 54.6 |
| Ethylene glycol saturated with 1-potassium 4-sodium terephthalate | Potassium hydroxide and sodium hydroxide | 24.1 | 59.9 |

(4) Depolymerization Reaction of a Waste PET Bottle Ground Product in a Solvent Containing Water In a 200 mL stainless-steel beaker, 10 g of a waste PET bottle ground product and 50 g of ethylene glycol were placed. And then, 0.083 mol, 0.090 mol, or 0.11 mol of potassium hydroxide (in a form of granule), or 0.083 mol, 0.090 mol, or 0.11 mol of a 34% aqueous potassium hydroxide solution was further put therein.

Subsequently, the resulting mixture was subjected, while vigorously stirred using a hot stirrer, to heat treatment at 160° C. for 60 minutes. As a result of mostly evaporating the water content in the depolymerization reaction solution added with the 34% aqueous potassium hydroxide solution, the fluid volume thereof became nearly equal to that of the depolymerization reaction solution added with potassium hydroxide (in a form of granule). The resultant was allowed to naturally cool; and when the inner temperature thereof reached 40° C. or less, the content was taken out. This content was filtered off with a filter paper to separate residues from a filtrate. The terephthalate content of these residues is shown on FIG. 3.

Figure 3:
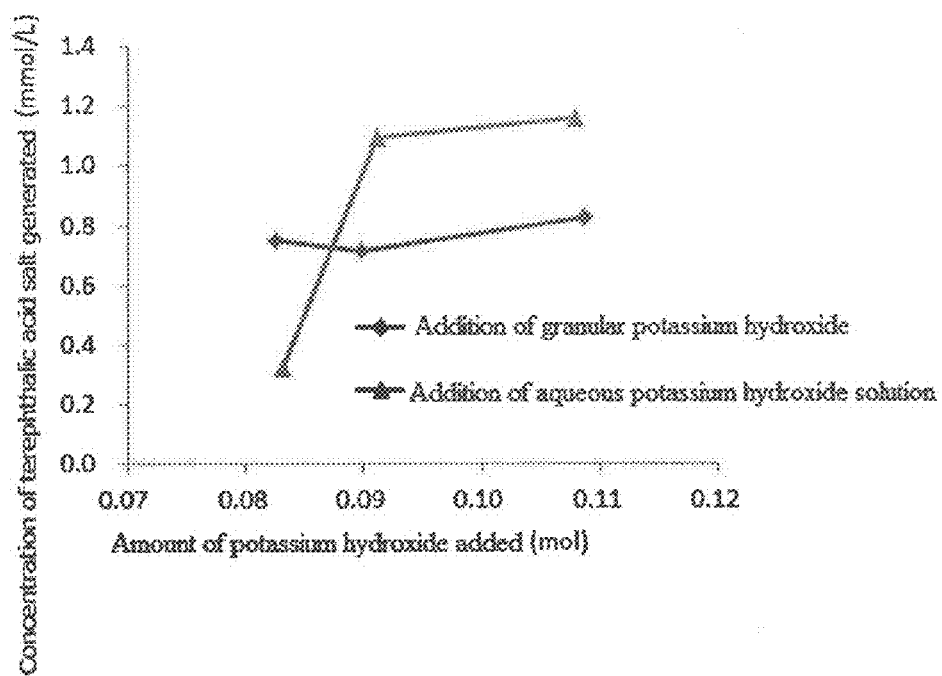
FIG. 3 is a graph showing the generation rate of terephthalic acid when the depolymerization is carried out in an ethylene glycol solvent containing granular potassium hydroxide or aqueous potassium hydroxide solution.

From the results shown in FIG. 3, it was found out that, when potassium hydroxide was put in an amount of 0.090 mol or 0.11 mol, the depolymerization reaction in the solvent containing water led to an excellent efficiency of generating terephthalic acid salts.

Example 7

Depolymerization of PTT in an Ethylene Glycol Solvent 13 g of batting made from PTT (manufactured by Nishikawa Sangyo Co., Ltd., FINE SMOOTH SOLOTEX batting refill package RC7954); and 130 g of an ethylene glycol solvent saturated with dipotassium terephthalate, which was prepared in Example 6(3) and 0.13 mol of potassium hydroxide; 130 g of a solution saturated with disodium terephthalate and 0.13 mol of sodium hydroxide; or 130 g of a 1-potassium 4-sodium terephthalate saturated solution, 0.066 mol of potassium hydroxide and 0.066 mol of sodium hydroxide were placed in a 200 mL stainless-steel beaker and subjected, while vigorously stirred using a hot stirrer, to heat treatment at 160° C. for 60 minutes to be hydrolyzed. The resultant was allowed to cool; and when the inner temperature thereof reached 40° C. or less, the content was taken out. This content was filtered off with a filter paper (Grade 540 manufactured by Whatman) to separate residues from a filtrate and then the weight of each of the residues and the total amount of terephthalic acid in the residue were measured. From the results shown in Table 9, it was found out that the total amount of terephthalic acid in the residue after the filtration in the order of from the highest to the lowest was potassium hydroxide, the mixture of potassium hydroxide and sodium hydroxide, and sodium hydroxide.

TABLE 9

Difference in the amount of terephthalic acid produced in depolymerization of PTT in the ethylene glycol solvent saturated with the terephthalic acid salt

| Solvent used in depolymerization of PTT | Alkali metal hydroxide used in depolymerization of PTT | The amount of residue collected (g) | The total amount of terephthalic acid in the residue (mmol) |
|---|---|---|---|
| Ethylene glycol saturated with dipotassium terephthalate | Potassium hydroxide | 20.7 | 64.8 |
| Ethylene glycol saturated with disodium terephthalate | Sodium hydroxide | 21.6 | 59.4 |
| Ethylene glycol saturated with 1-potassium 4-sodium terephthalate | Potassium hydroxide and sodium hydroxide | 25.3 | 60.5 |

Example 8

Depolymerization of PBT in an Ethylene Glycol Solvent

In a 200 mL, stainless-steel beaker, 15 g of a ground product of Chinese-style spoon made from PBT (PBT Chinese-style spoon 103TW white (RLVH001) was purchased from Amazon.com, Inc.) was added. 75 g of the ethylene glycol solvent saturated with dipotassium terephthalate, which was prepared in Example 6(3), and 0.15 mol of potassium hydroxide, 75 g of ethylene glycol solvent saturated with disodium terephthalate and 0.15 mol of sodium hydroxide, or 75 g of ethylene glycol solvent saturated with 1-potassium 2-sodium terephthalate salt and 0.075 mol of potassium hydroxide; and 0.075 mol of sodium hydroxide were further placed therein.

Subsequently, the resulting mixture was subjected, while vigorously stirred using a hot stirrer, to heat treatment at 160° C. for 120 minutes to be hydrolyzed. The resultant was allowed to cool; and when the inner temperature thereof reached 40° C. or less, the content was taken out.

This content was filtered off with a filter paper to separate residues from a filtrate and then the weight of each of the residues and the total amount of terephthalic acid in the residue were measured. From the results shown in Table 10, it was found out that the total amount of terephthalic acid in the residue after the filtration in the order of from the highest to the lowest was potassium hydroxide, the mixture of potassium hydroxide and sodium hydroxide, and sodium hydroxide.

TABLE 10

Difference in the amount of terephthalic acid produced in depolymerization of PBT in the ethylene glycol solvent saturated with the terephthalic acid salt

| Solvent used in depolymerization of PBT | Alkali metal hydroxide used in depolymerization of PBT | The amount of residue collected (g) | The total amount of terephthalic acid in the residue (mmol) |
| --- | --- | --- | --- |
| Ethylene glycol saturated with dipotassium terephthalate | Potassium hydroxide | 25.8 | 53.0 |
| Ethylene glycol saturated with disodium terephthalate | Sodium hydroxide | 26.8 | 41.4 |
| Ethylene glycol saturated with 1-potassium 4-sodium terephthalate | Potassium hydroxide and sodium hydroxide | 26.6 | 49.7 |

Example 9

Difference Between Potassium Hydroxide and Sodium Hydroxide in Depolymerization of Waste PET in 1-Butanol The solubility of dipotassium terephthalate and disodium terephthalate in 1-butanol was examined as the same manner as described in Example 1 and found to be 0.2 mM and 1.9 mM, respectively. As just seen above, it was found out that, unlike the dissolution in ethylene glycol, the dissolution in 1-butanol was very poor.

Thus, there were large differences in efficiency of collecting the terephthalic acid salt generated in the depolymerization reaction between a solvent for a depolymerization reaction using fresh 1-butanol and 1-butanol solvent that was once subjected to a depolymerization reaction of waste PET. Therefore, only examples using fresh 1-butanol will be shown in the following examples using 1-butanol.

In a 200 mL stainless-steel beaker, a waste PET bottle ground product 13 g and 1-butanol 80 g were placed. And then, 0.14 mol of potassium hydroxide (in a form of granule) or 0.14 mol of sodium hydroxide (in a form of granule) were put therein and subjected, while vigorously stirred using a hot stirrer, to heat treatment at 100° C. for 60 minutes or 90 minutes, respectively. These solutions were allowed to naturally cool; and, when the inner temperature thereof reached 40° C. or less, filtered off with a filter paper (Grade 540 manufactured by Whatman) to separate residues from a filtrate. The residue was washed with methanol 50 mL on a funnel and then dried using a vacuum dryer (manufactured by AS ONE Corporation) at 60° C. until a decrease in weight became less than 0.1 g/hour. The weight of the residue and terephthalic acid content in the residues are shown in Table 11. As shown in Table 11, it was found out that the use of potassium hydroxide led to a superior efficiency of generating the terephthalic acid salt to the use of sodium hydroxide.

TABLE 11

Difference in the amount of terephthalic acid produced among alkali metal hydroxides in depolymerization of PET in the 1-butanol solvent

| Alkali metal hydroxide used in depolymerization of PET | Heating time (min) | The amount of residue collected (g) | The total amount of terephthalic acid in the residue (mmol) |
| --- | --- | --- | --- |
| Potassium hydroxide | 60 | 17.1 | 67.5 |
| Potassium hydroxide | 90 | 16.1 | 67.3 |
| Sodium hydroxide | 60 | 14.5 | 59.2 |
| Sodium hydroxide | 90 | 14.5 | 63.9 |

Example 10

Difference Between Potassium Hydroxide and Sodium Hydroxide in Depolymerization of PTT in 1-Butanol In a 200 mL stainless-steel beaker, 13 g of batting made from PTT (manufactured by Nishikawa Sangyo Co., Ltd., FINE SMOOTH SOLOTEX batting refill package RC7954) and 130 g of 1-butanol were placed; and then 0.13 mol of potassium hydroxide (in a form of granule) or 0.13 mol of sodium hydroxide (in a form of granule) was placed therein. The resulting mixture was subjected, while vigorously stirred using a hot stirrer, to heat treatment at 100° C. for 90 minutes in the case of potassium hydroxide and at 100° C. for 120 minutes in the case of sodium hydroxide.

After the heat treatment, the resultant was allowed to naturally cool; and when the inner temperature thereof reached 40° C. or less, the content was taken out. This content was filtered off with a filter paper (Grade 540 manufactured by Whatman) to separate residues from a filtrate and then the weight of each of the residues and the total amount of terephthalic acid in the residue were measured.

From the results shown in Table 12, it was found out that, when potassium hydroxide was used, despite that the period of time of heating time was shorter, the total amount of terephthalic acid in the residue was greater, as compared with when sodium hydroxide was used.

TABLE 12

Difference in the amount of terephthalic acid produced among alkali metal hydroxides in depolymerization of PTT in the 1-butanol solvent

| Alkali metal hydroxide used in depolymerization of PTT | Heating time (min) | The amount of residue collected (g) | The total amount of terephthalic acid in the residue (mmol) |
| --- | --- | --- | --- |
| Potassium hydroxide | 60 | 26.1 | 60.2 |
| Sodium hydroxide | 120 | 22.2 | 54.3 |

Example 11

Difference Between Potassium Hydroxide and Sodium Hydroxide in Depolymerization of PBT in 1-Butanol In a 200 mL stainless-steel beaker, 15 g of the ground product of a Chinese-style spoon made from waste PBT, which was prepared in Example 7, and 75 g of 1-butanol were added; and then 0.15 mol of potassium hydroxide (in a form of granule) or 0.15 mol of sodium hydroxide (in a form of granule) was placed therein. The resulting mixture was subjected, while vigorously stirred using a hot stirrer, to heat treatment at 100° C. for 240 minutes, then allowed to naturally cool, and, when the inner temperature thereof reached 40° C. or less, the content was taken out.

This content was filtered off with a filter paper to separate residues from a filtrate and then the weight of each of the residues and the total amount of terephthalic acid in the residue were measured.

As shown in Table 13, it was found out that the total amount of terephthalic acid in the residue was greater when potassium hydroxide was used, as compared with when sodium hydroxide was used.

TABLE 13

Difference in the amount of terephthalic acid produced among alkali metal hydroxides in depolymerization of PBT in the 1-butanol solvent

| Alkali metal hydroxide used in depolymerization of PBT | The amount of residue collected (g) | The total amount of terephthalic acid in the residue(mmol) |
| --- | --- | --- |
| Potassium hydroxide | 26.0 | 44.5 |
| Sodium hydroxide | 25.0 | 43.3 |

Example 12

Decomposition of Ethylene Glycol at the Time of Production of TPA-DHD from Terephthalic Acid Salt Containing Ethylene Glycol With regard to a TPA-DHD producing bacterium having a capability of decomposing ethylene glycol, pUXPEaLT_tpaA_tpaK_Pm_fucO_I7L_aldA constructed in Reference Example 3 was introduced into *Escherichia coli* K-12 M7032 strain by a transformation method, thereby creating *Escherichia coli* M7032 (pUXPEaLT_tpaA_tpaK_Pm_fucO_I7L_aldA) strain.

Subsequently, in the same manner as described in Example 1, *Escherichia coli* M7032 (pUXPEaLT_tpaA_tpaK_Pm_fucO_I7L_aldA) strain and *Escherichia coli* K-12 M7032 strain which serves as a control were cultured in a mini jar fermentor. Concurrently with administration of dipotassium terephthalate which serves as a raw material, 0.278 ml (final concentration 72 mM) of ethylene glycol was placed.

Sampling was carried out 48 hours after the start of main culture. Each of the samples was subjected to analysis in conditions shown in Table 1 by an LC-TOF type mass spectrometer (Waters Corporation, LCT Premier XE). Identification of terephthalic acid was carried out with a combination of retention time of high performance liquid chromatography and an accurate mass value from the mass spectrometer, comparing to a standard sample of terephthalic acid. Among substances appeared as terephthalic acid decreased, TPA-DHD was identified on the basis of a predicted accurate mass value of TPA-DID. Further, quantification of TPA-DHD was carried out on the basis of a calibration curve prepared from an amount of terephthalic acid decreased and an increase in the peak area of TPA-DHD.

As a result, it was observed that TPA-DHD increased as terephthalic acid decreased. With regard to the amount of TPA-DHD produced 48 hours after the start of the culture, the amount of TPA-DHD produced 48 hours after the start of the culture of *Escherichia coli* M7032 (pUXPEaLT_tpaA_tpaK_Pm_fucO_I7L_aldA) strain and *Escherichia coli* K-12 M7032 strain was 10.5 g/L and 11.1 g/L, respectively.

Subsequently, the amount of ethylene glycol 48 hours after the start of the culture in the culture solution was subjected to analysis in conditions shown in Table 14 using an gas chromatography (GC) type mass spectrometer (GC: Agilent 7890A, mass spectrometer: Agilent 5975C). Ethylene glycol was identified by carrying out measurement of retention time of gas chromatography and measurement from the mass spectrometer with m/z62 as a target ion in combination, comparing a standard sample of ethylene glycol. As a result, the concentration of ethylene glycol 48 hours after the start of the culture of *Escherichia coli* M7032 (pUXPEaLT_tpaA_tpaK_Pm_fucO_I7L_aldA) strain and *Escherichia coli* M7032 strain was found to be 37.1 mM and 0.0 mM, respectively; and the enhancement of the expression amount of lactaldehyde reductase and lactaldehyde dehydrogenase was found to enable the decomposition of the ethylene glycol contained in terephthalate.

TABLE 14

Condition for analysis using gas chromatography type mass spectrometer

| | |
| --- | --- |
| Column | DB-WAX (inner diameter: 0.25 mm, length: 30 m, membrane thickness: 0.25 μm, J&W Scientific) |
| Injection temperature | 250° C. |
| Interface temperature | 250° C. |
| Injection mode | Splitless |
| Injection volume | 1 μl |
| Open program | 1 ml/min |
| MS mode | 40° C. (5 min), followed by increasing the temperature to 230° C. at a rate of 10° C./min |
| Detector gain | EI (70 eV) |
| Measurement mode | SIM |

Example 13

Production of Protocatechuic Acid from Terephthalic Acid Salt Obtained by Depolymerization of PET Using the protocatechuic acid-producing *Escherichia coli* strain M7032 (pUXPEaLT_tphA2A3BA1_tpaK) created in Reference Example 2, in the same manner as described in Example 2, the preculture of the present protocatechuic acid-producing bacteria was prepared and then merely 2% of such a preculture was inoculated in a main culture medium to carry out main culture. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, terephthalate dihydrodiol dehydrogenase protein, and terephthalic acid transporter protein. The glucose concentration was measured with time. When the glucose concentration reached 0, the terephthalic acid salt derived from PET, which was prepared in Example 6, was dissolved such that the concentration thereof was 0.6M, mixed with glucose, and administered to a culture device.

Sampling was carried out 52 hours after the start of the main culture. Each of the samples was subjected to analysis by an LC-TOF type mass spectrometer (Waters Corporation, LCT Premier XE). Identification of terephthalic acid and protocatechuic acid was carried out with a combination of retention time of high performance liquid chromatography and an accurate mass value from the mass spectrometer, comparing to a standard sample of terephthalic acid and protocatechuic acid.

As a result, it was observed that protocatechuic acid increased as terephthalic acid decreased. Table 15 shows a ratio with the amount of protocatechuic acid produced from each of the terephthalic acid salts 52 hours after the start of the culture as 100%. From the results shown in Table 15, it became clear that both of 2 kinds of the potassium terephthalates exhibited a superior capacity in the production of protocatechuic acid to the production of disodium terephthalate.

TABLE 15

Production of protocatechuic acid from the terephthalic acid salt obtained by depolymerization of PET

| Terephthalic acid salt used as a raw material | Protocatechuic acid (g/L) | Ratio of the capacity in production |
| --- | --- | --- |
| Disodium terephthalate | 10.2 | 100% |
| Dipotassium terephthalate | 11.5 | 113% |
| 1-potassium 4-sodium terephthalate | 11.1 | 108% |

Example 14

Production of TPA-DHD from Terephthalic Acid Salt Obtained by Depolymerization of PIT Using the TPA-DHD production recombinant *Escherichia coli* strain M7032 (pUXPEaLT_tphA2A3A1_tpaK) constructed in Reference Example 2, in the same manner as described in Example 2, the preculture of the present TPA-DHD production bacterium was prepared and then merely 2% of such a preculture was inoculated in a main culture medium to carry out main culture. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, and terephthalic acid transporter protein. The glucose concentration was measured with time. When the glucose concentration reached 0, the terephthalic acid salt derived from PTT, which was prepared in Example 7, was dissolved such that the concentration thereof was 0.6M, mixed with glucose, and administered to a culture device.

Sampling was carried out 48 hours after the start of the main culture. Each of the samples was subjected to analysis in conditions shown in Table 1 by an LC-TOF type mass spectrometer (Waters Corporation, LCT Premier XE). Identification of terephthalic acid was carried out with a combination of retention time of high performance liquid chromatography and an accurate mass value from the mass spectrometer, comparing to a standard sample of terephthalic acid. Among substances appeared as terephthalic acid decreased, TPA-DHD was identified on the basis of a predicted accurate mass value of TPA-DHD. Further, quantification of TPA-DHD was carried out on the basis of a calibration curve prepared from an amount of terephthalic acid decreased and an increase in the peak area of TPA-DHD.

As a result, it was observed that TPA-DHD increased as terephthalic acid decreased. Table 16 shows a ratio with the amount of TPA-DHD produced from each of the terephthalic acid salts 48 hours after the start of the culture as 100%. From the results shown in Table 16, it became clear that both of 2 kinds of the potassium terephthalic acid salts exhibited a superior capacity in the production of TPA-DHD to the production of disodium terephthalate.

TABLE 16

Production of TPA-DHD from the terephthalic acid salt obtained by depolymerization of PTT

| Terephthalate used as a raw material | TPA-DHD (g/L) | Ratio of the capacity in production |
| --- | --- | --- |
| Disodium terephthalate | 12.8 | 100% |
| Dipotassium terephthalate | 17.7 | 138% |
| 1-potassium 4-sodium terephthalate | 14.3 | 112% |

Example 15

Production of Protocatechuic Acid from Terephthalic Acid Salt Obtained by Depolymerization of PTT Using the protocatechuic acid-producing *Escherichia coli* strain M7032 (pUXPEaLT_tphA2A3BA1_tpaK) created in Reference Example 2, in the same manner as described in Example 2, the preculture of the present protocatechuic acid-producing bacterium was prepared and then merely 2% of such a preculture was inoculated in a main culture medium to carry out main culture. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, terephthalate dihydrodiol dehydrogenase protein, and terephthalic acid transporter protein. The glucose concentration was measured with time. When the glucose concentration reached 0, the terephthalic acid salt derived from PBT, which was prepared in Example 8, was dissolved such that the concentration thereof was 0.6M, mixed with glucose, and administered to a culture device.

Sampling was carried out 48 hours after the start of the main culture. Each of the samples was subjected to analysis by an LC-TOF type mass spectrometer (Waters Corporation, LCT Premier XE). Identification of terephthalic acid and protocatechuic acid was carried out with a combination of retention time of high performance liquid chromatography and an accurate mass value from the mass spectrometer, comparing to a standard sample of terephthalic acid and protocatechuic acid.

As a result, it was observed that protocatechuic acid increased as terephthalic acid decreased. Table 17 shows a ratio with the amount of protocatechuic acid produced from each of the terephthalic acid salts 48 hours after the start of the culture as 100%. From the results shown in Table 17, it became clear that both of 2 kinds of the potassium terephthalates exhibited a superior capacity in the production of protocatechuic acid to the production of disodium terephthalate.

TABLE 17

Production of protocatechuic acid from the terephthalic acid salt obtained by depolymerization of PBT

| Terephthalic acid salt used as a raw material | protocatechuic acid (g/L) | Ratio of the capacity in production |
| --- | --- | --- |
| Disodium terephthalate | 10.2 | 100% |
| Dipotassium terephthalate | 11.6 | 114% |
| 1-potassium 4-sodium terephthalate | 11.0 | 108% |

Example 16

Production of TPA-DHD from Terephthalic Acid Salt Obtained by Depolymerization of PET in 1-Butanol Solvent Using the TPA-DHD production recombinant *Escherichia coli* strain M7032 (pUXPEaLT_tphA2A3A1_tpaK) created in Reference Example 2, in the same manner as described in Example 2, the preculture of the present TPA-DHD production bacterium was prepared and then merely 2% of such a preculture was inoculated in a main culture medium to carry out main culture. When the bacterial cell turbidity reached about 7 at an absorbance of 600 nm, an inducer m-toluic acid was added such that the final concentration thereof came to 1 mM to express terephthalate 1,2-dioxygenase protein, terephthalate 1,2-dioxygenase reductase protein, and terephthalic acid transporter protein. The glucose concentration was measured with time. When the glucose concentration reached 0, the terephthalic acid salt derived from PET that was obtained by the depolymerization in 1-butanol, which terephthalic acid salt was prepared in Example 9, was dissolved so such that the concentration thereof was 0.6M, mixed with glucose, and administered to a culture device.

Sampling was carried out 35 hours after the start of the main culture. Each of the samples was subjected to analysis in conditions shown in Table 1 by an LC-TOF type mass spectrometer (Waters Corporation, LCT Premier XE). Identification of terephthalic acid was carried out with a combination of retention time of high performance liquid chromatography and an accurate mass value from the mass spectrometer, comparing to a standard sample of terephthalic acid. Among substances appeared as terephthalic acid decreased, TPA-DHD was identified on the basis of a predicted accurate mass value of TPA-DHD. Further, quantification of TPA-DHD was carried out on the basis of a calibration curve prepared from an amount of terephthalic acid decreased and an increase in the peak area of TPA-DHD.

As a result, it was observed that TPA-DHD increased as terephthalic acid decreased. Table 18 shows a ratio with the amount of TPA-DHD produced from each of the terephthalic acid salts 35 hours after the start of the culture as 100%. From the results shown in Table 18, it became clear that both of 2 kinds of the potassium terephthalic acid salts exhibited a superior capacity in the production of TPA-DHD to the production of disodium terephthalate.

TABLE 18

Production of TPA-DHD from the terephthalic acid salt obtained by depolymerization of PET in 1-butanol

| Terephthalic acid salt used as a raw material | TPA-DHD (g/L) | Ratio of the capacity in production |
|---|---|---|
| Disodium terephthalate | 12.8 | 100% |
| Dipotassium terephthalate | 17.4 | 136% |
| 1-potassium 4-sodium terephthalate | 14.8 | 116% |

Reference Example 1

Construction of Expression Vector pUXPEaLT19

In order to carry out efficient expression independent of the efficiency of transcription and translation of genes using *Escherichia coli*, construction of an expression system was carried out, wherein transcription of an intended gene depends on pseudogene and the intended gene was also translated in a state of maintaining the efficiency of translating the pseudogene. To be specific, in order to insert a terminator sequence into pUC19 (manufactured by Takara Bio Inc.), six of synthetic DNAs set forth in SEQ ID NOs: 13 to 18 were synthesized.

These synthetic DNAs were inserted between the KpnI site and EcoRI site of pUC19 to construct a plasmid pUC1LT1. A region between the PvuII site and HindIII site of pUC1LT1 was then deleted to construct pULTDL1. In order to insert a T7 promoter sequence and a PacI site for linking the pseudogene with the intended gene into pULTDL1, six of synthetic DNAs set forth in SEQ ID NOs: 19 to 24 were synthesized. These synthetic DNAs were inserted between the SphI site and SaiI site of pULTDL1 to construct an expression plasmid pUTPELT19. And then, by a PCR method using PrimeSTAR DNA polymerase (manufactured by Takara Bio Inc.; hereinafter, unless otherwise specified, this enzyme was used as a DNA amplification enzyme used in PCR reactions), a region between the BglII site and PacI site of pUTPELT19 was substituted by the sequence set forth in SEQ ID NO: 25 to construct an expression plasmid pUTPEaLT19.

Further, in order to construct an inducible expression system using an XylS-Pm promoter, DNA of an XylS-Pm promoter domain was obtained. The XylS-Pm promoter domain was amplified by a PCR reaction with a plasmid pJB866 which was obtained from National Institute of Genetics as a template using 2 kinds of DNA primers (SEQ ID NOs: 26 and 27). To the 3' end of amplified DNA fragment, an A residue was added by Taq DNA polymerase and such an amplified DNA fragment was purified by a gel electrophoresis method and incorporated into pT7Blue-T vector (manufactured by Novagen), thereby constructing a plasmid pT7-xylS_Pm retaining the entire region of XylS-Pm promoter.

The region of the XylS-Pm promoter was cut out from the plasmid pT7-xylS_Pm by a restriction enzyme SbfI and restriction enzyme BamHI and incorporated between SbfI site and BglII site of pUTPEaLT19, thereby creating an expression vector pUXPEaLT19.

Reference Example 2

Construction of Protocatechuic Acid-Producing Plasmid (1) Separation of *Comamonas testeroni* 72W2 Strain from Nature

*Comamonas testeroni* 72W2 strain was obtained as a bacterial strain growing with terephthalic acid as a sole carbon source from soil collected in Itabashi Ward, Tokyo.

To be specific, the collected soil sample was added to 5 ml of W liquid medium containing 10 mM of terephthalic acid placed in a 15 ml Falcon tube and cultured with shaking at 30° C. It is to be noted that the composition of W liquid medium is potassium dihydrogen phosphate 0.85 g/L, disodium hydrogen phosphate 4.9 g/L, ammonium sulfate 0.5 g/L, magnesium sulfate heptahydrate 9.5 mg/L, ferrous sulfate (II) heptahydrate 9.5 mg/L, magnesium oxide 10.75 mg/L, calcium carbonate 2 mg/L, zinc sulfate heptahydrate 4.5 mg/ml, manganese sulfate (II) tetrahydrate 1.12 mg/L, copper sulfate (II) pentahydrate 0.25 mg/L, cobalt sulfate (II) heptahydrate 0.28 g/L, and boric acid 0.06 mg/L.

The culture solution was spread on an agar plate of the W liquid medium containing 10 mM terephthalic acid and cultured at 30° C. to thereby select a bacterial strain growing with terephthalic acid as a sole carbon source. Colonies on the agar plate were cultured in the W liquid medium 5 ml containing 10 mM terephthalic acid for 3 days. By determining the 16S rDNA sequence of this bacterial strain, this bacterial strain was identified as *Comamonas testeroni* and named a 72W2 strain.

(2) Isolation of Genes from *Comamonas testeroni* 72W2 Strain

*Comamonas testeroni* 72W2 strain was cultured and cells were collected. Genomic DNA was extracted using illustra bacteria genomic Prep Mini Spin Kit (purchased from GE Healthcare Japan Corporation).

Next, the nucleotide sequence of an operon coding for a terephthalic acid metabolism gene cluster of *Comamonas testeroni* YZW-D strain was obtained as GB Accession No. AY923836 from the GB database of the National Center for Biotechnology Information (hereinafter, abbreviated as NCBI). Further, the nucleotide sequence of two operons coding for the terephthalic acid metabolism gene cluster possessed by *Comamonas* E6 strain was obtained from the GB database of NCBI. To be specific, for *Comamonas testeroni* YZW-D strain, a sequence of nucleotides 8242 to 11908 in GB Accession No. AY923836 was used as the nucleotide sequence of the operon of the terephthalic acid metabolism gene cluster. Because *Comamonas* bacterium E6 strain possessed 2 operons of the terephthalic acid metabolism gene cluster, a sequence of nucleotides 3260 to 6926 in GB Accession No. AB238678.1 and a sequence of nucleotides 4911 to 8577 in GB Accession No. AB238679.1 were each used as the nucleotide sequence of the operon of the terephthalic acid metabolism gene cluster.

On the basis of these sequences, degenerate primers were designed for cloning DNA coding for the terephthalic acid metabolism gene cluster of *Comamonas testeroni* 72W2 strain. Of such degenerate primers, a PacI recognition site was added to a 5'-primer (SEQ ID NO: 28) and a SgfI recognition site and NotI recognition site were added to a 3'-primer (SEQ ID NO: 29).

Using these 2 kinds of the degenerate primers, with the genomic DNA of *Comamonas testeroni* 72W2 strain as a template, an operon region of the terephthalic acid metabolism gene cluster (tphA2 gene-tphA3 gene-tphB gene-tphA1 gene; hereinafter abbreviated as tphA2A3BA1 gene) was amplified by a PCR reaction. The amplified DNA fragment was recovered using QIAquick PCR purification kit (manufactured by QIAGEN; hereinafter, unless otherwise specified, this kit was used as a PCR purification kit). After the nucleotide sequence of such an amplified DNA fragment was determined, it was confirmed that such a DNA coded for tphA2 gene coding for terephthalate 1,2-dioxygenase oxygenase large subunit protein (SEQ ID NO: 1), tphA3 gene coding for terephthalate 1,2-dioxygenase oxygenase small subunit protein (SEQ ID NO: 3), tphB gene coding for TPA-DHD dehydrogenase protein (SEQ ID NO: 9), and tphA1 gene coding for terephthalate 1,2-dioxygenase reductase protein (SEQ ID NO: 5).

The operon of tphA2A3BA1 gene (SEQ ID NO: 30) was cut out from the PCR product by a restriction enzyme PacI and restriction enzyme NotI and incorporated between the PacI site and NotI site of the expression vector pUXPEaLT19 described in Reference Example 1, thereby creating a plasmid pUXPEaLT_tphA2A3BA1 expressing a group of enzymes involved in conversion from terephthalic acid to protocatechuic acid.

(4) Cloning of Terephthalic Acid Transporter and Construction of Protocatechuic Acid-Producing Plasmid Because an ability of *Escherichia coli* K-12 strain to transport terephthalic acid was found to be weak, it was attempted to enhance the ability thereof to transport terephthalic acid by expressing a terephthalic acid transporter which promotes transport of terephthalic acid.

To be specific, DNA coding for a terephthalic acid transporter tpaK *Rhodococcus jostii* RHA1 strain which has an effect of promoting the transport of terephthalic acid to bacterial cells was be obtained. The nucleotide sequence of tpaK gene was obtained from the GB database of NCBI as the sequence of nucleotides 175046 to 176425 (SEQ ID NO: 7) in Accession No. CP000432. With the chromosomal DNA (100 ng) of *Rhodococcus jostii* RHA1 strain obtained from Professor Masao Fukuda, Nagaoka University of Technology as a template, using 2 kinds of DNA primers (SEQ ID NO: 31 and SEQ ID NO: 32), the entire region of tpaK gene coding for terephthalic acid transporter protein (SEQ ID NO: 8) was amplified by PCR.

The amplified DNA fragment was recovered using a PCR purification kit. The tpaK gene was cut out from the PCR product by a restriction enzyme PacI and restriction enzyme NotI and incorporated between the SgfI site and NotI site of the above-mentioned plasmid pUXPEaLT_tphA2A3BA1, thereby creating a protocatechuic acid-producing plasmid pUXPEaLT_tphA2A3BA1_tpaK.

Reference Example 3

Construction of TPA-DHD Production Plasmid

With pUXPEaLT_tphA2A3BA1_tpaK (100 ng) constructed in Reference Example 2(4) as a template, and using 2 kinds of DNA primers (SEQ ID NO: 28 and SEQ ID NO: 33), a tphA2 gene-tphA3 gene region was amplified by PCR. Further, using 2 kinds of DNA primers (SEQ ID NO: 29 and SEQ ID NO: 34), a tphA1 gene region was amplified by PCR. These amplified DNA fragments were recovered using a PCR purification kit. Subsequently, with the amplified fragment of the tphA2 gene-tphA3 gene region and the tphA1 gene amplified fragment, both of which were recovered, as a template, and using 2 kinds of DNA primers (SEQ ID NO: 28 and SEQ ID NO: 29), a tphA2-tphA3-tphA1 gene region was amplified by a PCR reaction. The amplified DNA fragment was recovered using a PCR purification kit. The amplified fragment was digested by a restriction enzyme PacI and restriction enzyme HindIII, and then incorporated between the PacI site and HindIII site of the expression vector pUXPEaLT_tphA2A3BA1 created in Reference Example 2(3), thereby constructing pUXPEaLT_tphA2A3A1_tpaK.

Reference Example 4

Construction of Gallic Acid-Producing Plasmid

For the purpose of efficiently converting protocatechuic acid into gallic acid, a plasmid expressing para-hydroxybenzoate hydroxylase gene in conjunction with the protocatechuic acid-producing gene cluster was constructed as follows: To be specific, with DNA (SEQ ID NO: 11) coding for para-hydroxybenzoate hydroxylase (SEQ ID NO: 12) disclosed in Japanese Patent Application Laid-Open Publication No. 2009-213392 as a template, and using 2 kinds of DNA primers (SEQ ID NO: 35 and SEQ ID NO: 36), DNA coding for para-hydroxy benzoate hydroxylase protein was amplified by PCR. The amplified DNA fragment was recovered using a PCR purification kit. The DNA was digested by a restriction enzyme PacI and restriction enzyme SgfI, and then incorporated in the PacI site of pUXPEaLT_tphA2A3BA1 tpaK created above, thereby constructing a gallic acid-producing plasmid pUXPEaLT_HFM145_tphA2A3BA1_tpaK.

Reference Example 5

Creation of Ethylene Glycol Decomposing Bacterium (1) Cloning of fucO Gene of *Escherichia coli* K-12 Strain The nucleotide sequence of fucO gene coding for lactaldehyde reductase protein derived from *Escherichia coli* K-12 MG1655 strain was obtained as the sequence of positions 13420 to 14571 of the nucleotide sequence (GB Accession No. U29581) obtained from NCBI via the Internet. Using 2 kinds of DNA primers (SEQ ID NO: 37 and SEQ ID NO: 38) synthesized on the basis of this sequence, with the chromosomal DNA (100 ng) of *Escherichia coli* K-12 MG1655 strain obtained from NBRP as a template, the entire region of fucO gene was amplified by PCR. This amplified DNA fragment was cut out from the PCR product by a restriction enzyme PacI and restriction enzyme NotI and incorporated in the expression vector pUXPEaLT19 created in Reference Example 1, thereby creating a plasmid pUXPEaLT_fucO_I7L.

(2) Cloning of aldA Gene of *Escherichia coli* K-12 Strain

The nucleotide sequence of aldA gene coding for lactaldehyde dehydrogenase protein derived from *Escherichia coli* K-12 MG1655 strain was obtained as the sequence of positions 1486256 to 1487695 of the nucleotide sequence (GB Accession No. U00096.2) obtained from NCBI via the Internet. Using 2 kinds of DNA primers (SEQ ID NO: 39 and SEQ ID NO: 40) synthesized on the basis of this sequence, with the chromosomal DNA (100 ng) of *Escherichia coli* K-12 MG1655 strain obtained from NBRP as a template, the entire region of aldA gene was amplified by PCR. This amplified DNA fragment was cut out from the PCR product by a restriction enzyme SwaI and restriction enzyme NotI and incorporated in the plasmid pUXPEaLT_fucO_I7L, thereby creating a plasmid pUXPEaLT_fucO_I7L_aldA.

A fragment was cut out from a synthetic DNA having the sequence set forth in SEQ ID NO: 41 by a restriction enzyme NotI and restriction enzyme AscII and incorporated between the NotI site and AscI site of the plasmid pUEPEaLT_fucO_I7L_aldA, thereby creating a plasmid pUXPEaLTEk_fucO_I7L_aldA.

Subsequently, using 2 kinds of DNA primers (SEQ ID NO: 42 and SEQ ID NO: 43), an expression unit containing fucO gene and aldA gene (hereinafter abbreviated as a fucO-aldA expression unit) was amplified from the plasmid pUXPEaLTEX_fucO_I7L_aldA by PCR. A fragment was cut out from the PCR product by a restriction enzyme AscI site and incorporated in the expression vector pUXPEaLT_tphA2A3A1_tpaK created in the above (Reference Example 3), thereby constructing a plasmid pUXPEaLT_tpaA_tpaK_PmfucO_I7L_aldA.

INDUSTRIAL APPLICABILITY

According to the present invention, provided are a method of producing terephthalate 1,2-cis-dihydrodiol with potassium terephthalate as a raw material using a microorganism expressing terephthalate 1,2-dioxygenase, a method of further converting TPA-DHD into phenol acids such as protocatechuic acid or gallic acid, and a method of obtaining the potassium terephthalate that serves as the raw material by depolymerization of waste polyesters.

DESCRIPTION OF SEQUENCE LISTING

SEQ ID NO: 1: DNA coding for terephthalate 1,2-dioxygenase oxygenase large subunit protein
SEQ ID NO: 2: Terephthalate 1,2-dioxygenase oxygenase large subunit protein
SEQ ID NO: 3: DNA coding for terephthalate 1,2-dioxygenase oxygenase small subunit protein
SEQ ID NO: 4: Terephthalate 1,2-dioxygenase oxygenase small subunit protein
SEQ ID NO: 5: DNA coding for terephthalate 1,2-dioxygenase reductase protein
SEQ ID NO: 6: Terephthalate 1,2-dioxygenase reductase protein
SEQ ID NO: 7: DNA coding for terephthalic acid transporter protein
SEQ ID NO: 8: Terephthalic acid transporter protein
SEQ ID NO: 9: DNA coding for TPA-DHD dehydrogenase protein
SEQ ID NO: 10: TPA-DHD dehydrogenase protein
SEQ ID NO: 11: DNA coding for para-hydroxybenzoate hydroxylase protein
SEQ ID NO: 12: Para-hydroxybenzoate hydroxylase protein
SEQ ID NO: 13: Synthetic DNA for terminator construction
SEQ ID NO: 14: Synthetic DNA for terminator construction
SEQ ID NO: 15: Synthetic DNA for terminator construction
SEQ ID NO: 16: Synthetic DNA for terminator construction
SEQ ID NO: 17: Synthetic DNA for terminator construction
SEQ ID NO: 18: Synthetic DNA for terminator construction
SEQ ID NO: 19: Synthetic for constructing DNA T7 promoter and pseudogene
SEQ ID NO: 20: Synthetic for constructing DNA T7 promoter and pseudogene
SEQ ID NO: 21: Synthetic for constructing DNA T7 promoter and pseudogene
SEQ ID NO: 22: Synthetic for constructing DNA T7 promoter and pseudogene
SEQ ID NO: 23: Synthetic for constructing DNA T7 promoter and pseudogene
SEQ ID NO: 24: Synthetic for constructing DNA T7 promoter and pseudogene
SEQ ID NO: 25: Sequence between the restriction enzyme BglII site and restriction enzyme PacI site of plasmid pUT-PELT19
SEQ ID NO: 26: PCR primer for obtaining DNA of XylS-Pm promoter domain
SEQ ID NO: 27: PCR primer for obtaining DNA of XylS-Pm promoter domain
SEQ ID NO: 28: Degenerate PCR primer for cloning the terephthalic acid metabolism gene cluster of *Comamonas testeroni*
SEQ ID NO: 29: Degenerate PCR primer for cloning the terephthalic acid metabolism gene cluster of *Comamonas testeroni*
SEQ ID NO: 30: DNA coding for the terephthalic acid metabolism gene cluster of *Comamonas testeroni* 72W2 strain
SEQ ID NO: 31: PCR primer for cloning terephthalic acid transporter
SEQ ID NO: 32: PCR primer for cloning terephthalic acid transporter
SEQ ID NO: 33: PCR primer for cloning the tphA2 gene-tphA3 gene region
SEQ ID NO: 34: PCR primer for cloning the tphA1 gene region
SEQ ID NO: 35: PCR primer for cloning improved para-hydroxybenzoate hydroxylase
SEQ ID NO: 36: PCR primer for cloning improved para-hydroxybenzoate hydroxylase
SEQ ID NO: 37: PCR primer for cloning *Escherichia coli* lactaldehyde reductase SEQ ID NO: 38: PCR primer for cloning *Escherichia coli* lactaldehyde reductase SEQ ID NO: 39: PCR primer for cloning *Escherichia coli* lactaldehyde dehydrogenase SEQ ID NO: 40: PCR primer for cloning *Escherichia coli* lactaldehyde dehydrogenase SEQ ID NO: 41: Sequence between the NotI site and AscI site of plasmid pUXPEaLTEk_fucO_I7L_aldA SEQ ID NO: 42: PCR primer for cloning the expression unit containing fucO gene and aldA gene SEQ ID NO: 43: PCR primer for cloning the expression unit containing fucO gene and aldA gene While the invention has been described in detail with reference to preferred embodiments thereof, it will be apparent to one skilled in the art that various changes can be made, and equivalents employed, without departing from the scope of the invention. Each of the aforementioned documents as well as PCT/JP2012/051854 is incorporated by reference herein in its entirety.

What is claimed is:

1. A method of producing terephthalate 1,2-cis-dihydrodiol or metabolite thereof comprising reacting a microorganism or a processed product of a culture thereof with terephthalic acid in an aqueous medium containing a terephthalic acid salt to generate terephthalate 1,2-cis-dihydrodiol or metabolite thereof, wherein said terephthalic acid salt comprises terephthalic acid potassium salt and the molar amount of potassium in the terephthalic acid salt is between 0.5 times and 2 times the molar amount of the terephthalic acid contained in the terephthalic acid salt, wherein said microorganism has the ability to produce terephthalate 1,2-cis-dihydrodiol from terephthalic acid and comprises three DNAs selected from the group consisting of (a), (b), (c), (d), (e), (f), (g), (h), and (i), wherein the first DNA is any one of the DNAs set forth in (a), (b), or (c), wherein the second DNA is any one of the DNAs set forth in (d), (e), or (f), wherein the third DNA is any one of the DNAs set forth in (g), (h), or (i), and wherein the DNAs of (a) to (i) are:

(a) a DNA coding for a protein comprising the amino acid sequence set forth in SEQ ID NO: 2;

(b) a DNA coding for a protein having the activity of a terephthalate 1,2-dioxygenase oxygenase large subunit protein which is involved in the conversion of terephthalic acid into terephthalate 1,2-cis dihydrodiol, wherein said protein comprises an amino acid sequence at least 95% identical to the whole amino acid sequence set forth in SEQ ID NO: 2;

(c) a DNA comprising the nucleotide sequence set forth in SEQ ID NO: 1;

(d) a DNA coding for a protein comprising the amino acid sequence set forth in SEQ ID NO: 4;

(e) a DNA coding for a protein having the activity of a terephthalate 1,2-dioxygenase oxygenase small subunit protein which is involved in the conversion of terephthalic acid into terephthalate 1,2-cis dihydrodiol, wherein said protein comprises an amino acid sequence at least 95% identical to the whole amino acid sequence set forth in SEQ ID NO: 4;

(f) a DNA comprising the nucleotide sequence set forth in SEQ ID NO: 3;

(g) a DNA coding for a protein comprising the amino acid sequence set forth in SEQ ID NO: 6;
(h) a DNA coding for a protein having the activity of a terephthalate 1,2-dioxygenase reductase protein which is involved in the conversion of terephthalic acid into terephthalate 1,2-cis-dihydrodiol, wherein said protein comprises an amino acid sequence at least 95% identical to the whole amino acid sequence set forth in SEQ ID NO: 6; and
(i) a DNA comprising the nucleotide sequence set forth in SEQ ID NO: 5.

2. The method according to claim 1, wherein said aqueous medium containing a terephthalic acid salt is an aqueous solution containing one or more potassium terephthalates selected from the group consisting of dipotassium terephthalate, 1-potassium 4-sodium terephthalate, and 1-potassium 4-ammonium terephthalate.

3. The method according to claim 1, wherein said terephthalic acid salt to be added to the aqueous medium is in the form of an aqueous solution, a powder, or a suspension.

4. The method according to claim 1, wherein the microorganism further has an enhanced ability to intracellularly transport terephthalic acid and comprises a DNA selected from the group consisting of:
(a) a DNA coding for a protein comprising the amino acid sequence set forth in SEQ ID NO: 8;
(b) a DNA coding for a protein having the activity of a terephthalic acid transporter, wherein said protein comprises an amino acid sequence at least 95% identical to the whole amino acid sequence set forth in SEQ ID NO: 8; and
(c) a DNA comprising the nucleotide sequence set forth in SEQ ID NO: 7.

5. The method according to claim 1 further comprising steps for obtaining the terephthalic acid salt, wherein said steps are:
(A) heating a polyester waste material containing polyethylene terephthalate, polytrimethylene terephthalate, or polybutylene terephthalate as a major component and containing a foreign substance in an ethylene glycol reaction solvent containing potassium hydroxide or in an ethylene glycol reaction solvent containing both potassium hydroxide and sodium hydroxide at between 100° C. and 196° C. for 10 minutes or more to evaporate water and to depolymerize the polyethylene terephthalate, polytrimethylene terephthalate, or polybutylene terephthalate contained in the waste material;
(B) removing the solid foreign substance floating in the depolymerization reaction solution from solid foreign substances contained in the solution;
(C) collecting solids other than the floating foreign substance of step (B) by a solid-liquid separation method; and
(D) subjecting the solids collected in step (C) to heat drying treatment, drying treatment under reduced pressure, or centrifugation treatment to thereby decrease the content of ethylene glycol in the solids and obtain a depolymerization reaction solution comprising a terephthalic acid salt in solid form.

6. The method according to claim 5, wherein the method further comprises collecting the ethylene glycol of the depolymerization reaction solution obtained from the solid-liquid separation in step (C), and recycling the ethylene glycol in step (A).

7. The method according to claim 5, wherein said microorganism has been modified to increase the expression of a lactaldehyde reductase from *Escherichia coli* and a lactate dehydrogenase from *Escherichia coli* compared to the expression of the lactaldehyde reductase and lactate dehydrogenase in the corresponding unmodified microorganism, and wherein said microorganism is able to decompose the ethylene glycol contained in the terephthalic acid salt obtained in step (D).

8. The method according to claim 1 further comprising steps for obtaining the terephthalic acid salt, wherein said steps are:
(A) heating a polyester waste material containing polyethylene terephthalate, polytrimethylene terephthalate, or polybutylene terephthalate as a major component and containing a foreign substance in a 1-butanol reaction solvent containing potassium hydroxide or in a 1-butanol reaction solvent containing both potassium hydroxide and sodium hydroxide at between 100° C. and 116° C. for 10 minutes or more to evaporate water and to depolymerize the polyethylene terephthalate, polytrimethylene terephthalate, or polybutylene terephthalate contained in the waste material;
(B) removing the solid foreign substance floating in the depolymerization reaction solution from solid foreign substances contained in the solution;
(C) collecting solids other than the floating foreign substance of step (B) by a solid-liquid separation method; and
(D) subjecting the solids collected in step (C) to heat drying treatment, drying treatment under reduced pressure, or centrifugation treatment to thereby decrease the content of 1-butanol in the solids and obtain a depolymerization reaction solution comprising a terephthalic acid salt in solid form.

9. The method according to claim 8, wherein the method further comprises collecting the 1-butanol of the depolymerization reaction solution obtained from the solid-liquid separation in step (C); and recycling the 1-butanol in step (A).

10. The method according to claim 1, wherein said metabolite is protocatechuic acid and said microorganism has the ability to produce protocatechuic acid from terephthalic acid and comprises a DNA selected from the group consisting of (a), (b) and (c), wherein the DNAs of (a) to (c) are:
(a) a DNA coding for a protein comprising the amino acid sequence set forth in SEQ ID NO: 10;
(b) a DNA coding for a protein having the activity of a terephthalate 1,2-cis dihydrodiol (TPA-DHD) dehydrogenase protein which is involved in the conversion of terephthalate 1,2-cis-dihydrodiol into protocatechuic acid, wherein said protein comprises an amino acid sequence at least 95% identical to the whole amino acid sequence set forth in SEQ ID NO: 10; and
(c) a DNA comprising the nucleotide sequence set forth in SEQ ID NO: 9.

11. The method according to claim 1, wherein said metabolite is gallic acid and said microorganism has the ability to produce gallic acid from terephthalic acid and comprises two DNAs selected from the group consisting of (a), (b), (c), (d), (e) and (f), wherein the first DNA is any one of the DNAs set forth in (a), (b) or (c), wherein the second DNA is any one of the DNAs set forth in (d), (e) or (f), and wherein the DNAs of (a) to (f) are:
(a) a DNA coding for a protein comprising the amino acid sequence set forth in SEQ ID NO: 10;
(b) a DNA coding for a protein having the activity of a TPA-DHD dehydrogenase protein which is involved in the conversion of terephthalate 1,2-cis-dihydrodiol into protocatechuic acid, wherein said protein comprises an amino acid sequence at least 95% identical to the whole amino acid sequence set forth in SEQ ID NO: 10;
(c) a DNA comprising the nucleotide sequence set forth in SEQ ID NO: 9;
(d) a DNA coding for a protein comprising the amino acid sequence set forth in SEQ ID NO: 12;
(e) a DNA coding for a protein having the activity of a para-hydroxybenzoate hydroxylase protein which is involved in the conversion of protocatechuic acid into gallic acid, wherein said protein comprises an amino acid sequence at least 95% identical to the whole amino acid sequence set forth in SEQ ID NO: 12; and
(f) a DNA comprising the nucleotide sequence set forth in SEQ ID NO: 11.

12. The method according to claim 1, wherein said microorganism is *Escherichia coli*.

* * * * *